(12) United States Patent
Kuroda et al.

(10) Patent No.: US 12,349,860 B2
(45) Date of Patent: Jul. 8, 2025

(54) MEDICAL OBSERVATION SYSTEM, CONTROL DEVICE, AND CONTROL METHOD

(71) Applicant: Sony Group Corporation, Tokyo (JP)

(72) Inventors: Yohei Kuroda, Tokyo (JP); Masaru Usui, Tokyo (JP); Jun Arai, Tokyo (JP)

(73) Assignee: Sony Group Corporation, Tokyo (JP)

( * ) Notice: Subject to any disclaimer, the term of this patent is extended or adjusted under 35 U.S.C. 154(b) by 691 days.

(21) Appl. No.: 17/606,463

(22) PCT Filed: Jul. 3, 2020

(86) PCT No.: PCT/JP2020/026304
§ 371 (c)(1),
(2) Date: Oct. 26, 2021

(87) PCT Pub. No.: WO2021/006228
PCT Pub. Date: Jan. 14, 2021

(65) Prior Publication Data
US 2022/0192777 A1 Jun. 23, 2022

(30) Foreign Application Priority Data
Jul. 10, 2019 (JP) .................................. 2019-128112

(51) Int. Cl.
*A61B 34/10* (2016.01)
*A61B 1/00* (2006.01)
(Continued)

(52) U.S. Cl.
CPC .... *A61B 1/000096* (2022.02); *A61B 1/00194* (2022.02); *A61B 34/10* (2016.02);
(Continued)

(58) Field of Classification Search
CPC ... A61B 34/10; A61B 90/37; A61B 2034/102; A61B 2034/105; G06T 7/0012; G06V 10/82
See application file for complete search history.

(56) References Cited

U.S. PATENT DOCUMENTS

| | | | | |
|---|---|---|---|---|
| 2012/0249819 A1* | 10/2012 | Imai | ...................... | H04N 23/63 348/222.1 |
| 2015/0320324 A1* | 11/2015 | Jung | .................. | A61B 5/02007 600/407 |

(Continued)

FOREIGN PATENT DOCUMENTS

| | | |
|---|---|---|
| EP | 3 420 878 A1 | 1/2019 |
| WO | 2017/145475 A1 | 8/2017 |

(Continued)

OTHER PUBLICATIONS

Jiang, J., Trundle, P., & Ren, J. (2010). Medical image analysis with artificial neural networks. Computerized Medical Imaging and Graphics, 34(8), 617-631. (Year: 2010).*

(Continued)

*Primary Examiner* — Bobbak Safaipour
*Assistant Examiner* — Ashley L. Hytrek
(74) *Attorney, Agent, or Firm* — XSENSUS LLP

(57) ABSTRACT

A method and system for processing medical images including acquiring a first medical image using a medical imaging device, analyzing a state of the first medical image using image information of the first medical image which includes depth information, and automatically determining and displaying, without user intervention, a second medical image, which corresponds to the first medical image and has a smaller angle of view than the first medical image, based on the analyzing including analyzing of the depth information. Further, there is a method of training a neural network. The training includes collecting a set of training information (Continued)

which includes image quality information, camera position information, and surgical tool information, training the neural network based on the set of training information, the neural network used for changing a view based on current camera position information and current surgical tool information.

34 Claims, 28 Drawing Sheets

(51) Int. Cl.
*A61B 90/00* (2016.01)
*G06T 7/00* (2017.01)
*G06V 10/82* (2022.01)

(52) U.S. Cl.
CPC ............ *A61B 90/37* (2016.02); *G06T 7/0012* (2013.01); *G06V 10/82* (2022.01); *A61B 2034/102* (2016.02); *A61B 2034/105* (2016.02)

(56) References Cited

U.S. PATENT DOCUMENTS

| | | | |
|---|---|---|---|
| 2019/0053857 A1* | 2/2019 | Sugie | A61B 1/00 |
| 2019/0192251 A1* | 6/2019 | Kado | G02B 21/22 |
| 2019/0365499 A1* | 12/2019 | Nagao | B25J 13/00 |
| 2020/0100649 A1* | 4/2020 | Inoue | A61B 1/045 |

FOREIGN PATENT DOCUMENTS

| | | |
|---|---|---|
| WO | 2018/159328 A1 | 9/2018 |
| WO | WO-2018173681 A1 | 9/2018 |
| WO | 2018/225132 A1 | 12/2018 |
| WO | WO-2019163890 A1 | 8/2019 |
| WO | WO-2019163906 A1 | 8/2019 |
| WO | WO-2019225132 A1 | 11/2019 |

OTHER PUBLICATIONS

International Search Report and Written Opinion mailed on Sep. 30, 2020, received for PCT Application PCT/JP2020/026304, Filed on Jul. 3, 2020, 11 pages.

* cited by examiner

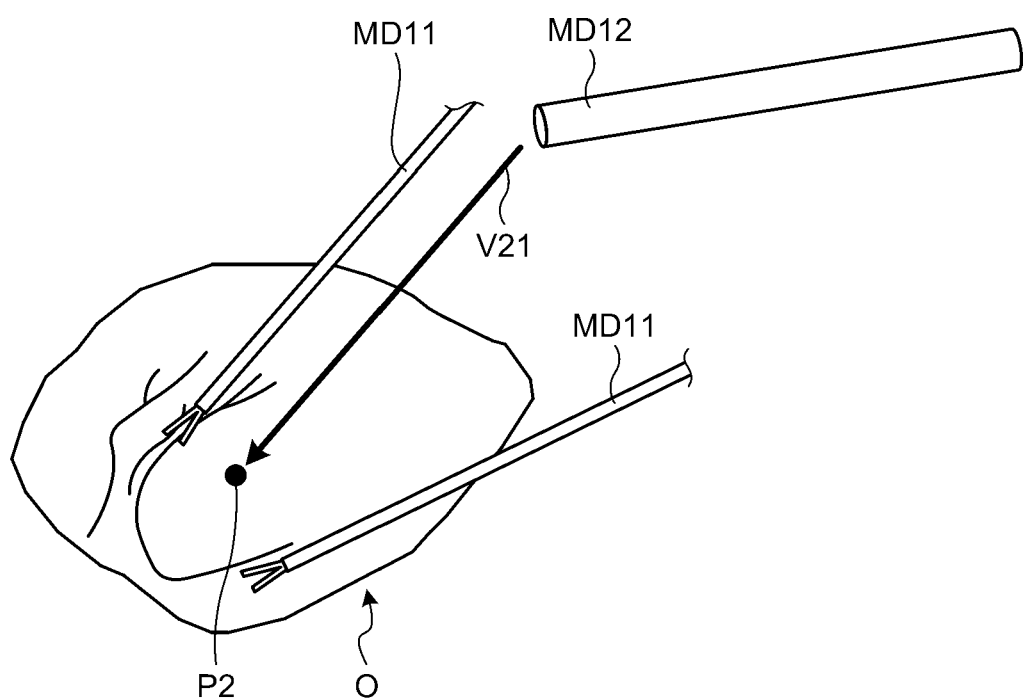

MEDICAL OBSERVATION SYSTEM, CONTROL DEVICE, AND CONTROL METHOD

CROSS-REFERENCE TO RELATED APPLICATIONS

The present application is based on PCT filing PCT/JP2020/026304, filed Jul. 3, 2020, which claims priority to JP 2019-128112, filed Jul. 10, 2019, the entire contents of each are incorporated herein by reference.

TECHNICAL FIELD

The present disclosure relates to a medical observation system, a control device, and a control method.

BACKGROUND ART

In recent years, in endoscopic surgery, an endoscope is used to take an image in the abdominal cavity of a patient, and a surgery is performed while the image taken by the endoscope is displayed on a display.

For example, Patent Literature 1 discloses a technology for enabling control of an arm supporting an endoscope and control of electronic zooming of the endoscope to cooperate.

CITATION LIST

Patent Literature

PTL 1: WO 2017/145475

SUMMARY OF INVENTION

Technical Problem

Conventional laparoscopes do not have a degree of freedom in the body and have a limit to field-of-view expansion, thus causing blind spots. An arm device having a function for recognizing a tool by image recognition and following a camera has been proposed. However, the field of view of the current endoscope is as narrow as about 80 degrees, and only a part of a tool appears in an enlarged view. Thus, recognition accuracy of the tool may reduce at a screen end. When the recognition accuracy is reduced, the controllability of the arm may deteriorate.

Therefore, the present disclosure proposes a medical observation system, a control device, and a control method capable of improving recognition accuracy of images and appropriately controlling the motion of an arm device based on images.

Solution to Problem

According to one aspect of the present disclosure, there is a method of processing medical images which includes acquiring a first medical image using a medical imaging device; analyzing a state of the first medical image using image information of the first medical image which includes depth information; automatically determining, without user intervention, a second medical image, which corresponds to the first medical image and has a smaller angle of view than the first medical image, based on the analyzing including analyzing of the depth information; and displaying the second medical image.

According to another aspect of the present disclosure, there is a medical system which includes a medical imaging device; circuitry configured to control the medical imaging device to acquire a first medical image; circuitry configured to perform analyzing of a state of the first medical image using image information of the first medical image which includes depth information; and circuitry configured to automatically determine without user intervention a second medical image, which corresponds to the first medical image and has a smaller angle of view than the first medical image, based on the analyzing including analyzing of the depth information, and cause a display to display the second medical image.

Still further, yet another aspect of the present disclosure includes a computer-implemented method of training a neural network which includes collecting a set of training information which includes image quality information, camera position information, and surgical tool information; training the neural network based on the set of training information, the neural network used for changing a view based on current camera position information and current surgical tool information.

BRIEF DESCRIPTION OF DRAWINGS

FIG. 14B is a diagram for describing a determination result of the learning unit according to the embodiment of the present disclosure.

DESCRIPTION OF EMBODIMENTS

Embodiments of the present disclosure are described in detail below with reference to the drawings. In the following embodiments, the same portions are denoted by the same reference symbols to omit overlapping descriptions.

Figure 1:
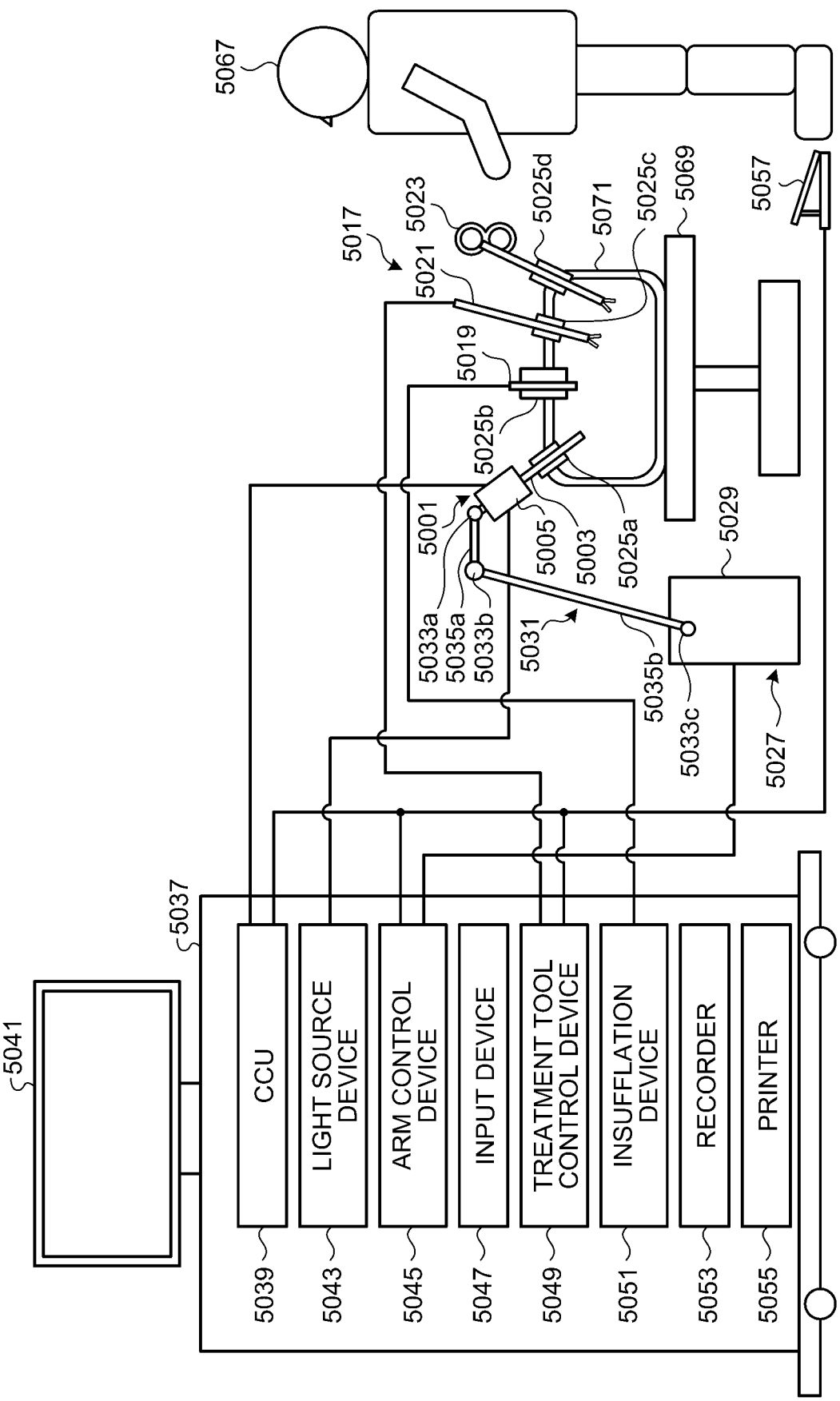
FIG. 1 is a diagram illustrating an example of a schematic configuration of an endoscopic surgical system to which the technology according to the present disclosure may be applied.

The present disclosure is described in the order of items described below:

1. Configuration example of endoscope system
2. Specific configuration example of support arm device
3. Basic configuration of forward-oblique viewing endoscope
4. Medical observation system
5. Control of arm supporting forward-oblique viewing endoscope
6. Setting of virtual links; and
7. Hardware configuration 1. Configuration Example of Endoscope System FIG. 1 is a diagram illustrating an example of a schematic configuration of an endoscopic surgical system 5000 to which the technology according to the present disclosure may be applied. FIG. 1 illustrates a situation in which an operator (doctor) 5067 uses the endoscopic surgical system 5000 to perform a surgery on a patient 5071 on a patient bed 5069. As illustrated in FIG. 1, the endoscopic surgical system 5000 includes an endoscope 5001, other surgical tools 5017, a support arm device 5027 that supports the endoscope 5001, and a cart 5037 in which various kinds of devices for endoscopic surgery are mounted.

In endoscopic surgery, a plurality of cylindrical incision tools called trocars 5025a to 5025d are needled into the abdominal wall instead of cutting the abdominal wall for laparotomy. Through the trocars 5025a to 5025d, a lens barrel 5003 in the endoscope 5001 and other surgical tools 5017 are inserted to the body cavity of the patient 5071. In the illustrated example, as the other surgical tools 5017, an insufflation tube 5019, an energy treatment tool 5021, and forceps 5023 are inserted to the body cavity of the patient 5071. The energy treatment tool 5021 is a treatment tool for cutting and releasing of tissues or sealing of blood vessels by high-frequency current or ultrasonic vibration. The illustrated surgical tools 5017 are merely an example, and as the surgical tools 5017, for example, various kinds of surgical tools used in general endoscopic surgery, such as tweezers and retractors, may be used.

An image of a surgical part in the body cavity of the patient 5071 taken by the endoscope 5001 is displayed on a display device 5041. While viewing the image of the surgical part displayed on the display device 5041 in real time, the operator 5067 uses the energy treatment tool 5021 and the forceps 5023 to perform treatments, such as cutting an affected part. Although not shown, the insufflation tube 5019, the energy treatment tool 5021, and the forceps 5023 are supported by the operator 5067 or an assistant during a surgery.

Support Arm Device

The support arm device 5027 includes an arm portion 5031 extending from a base portion 5029. In the illustrated example, the arm portion 5031 includes joint portions 5033a, 5033b, and 5033c and links 5035a and 5035b, and is driven by control from an arm control device 5045. The endoscope 5001 is supported by the arm portion 5031, and the position and posture of the endoscope 5001 are controlled. In this manner, the position of the endoscope 5001 may be stably fixed.

Endoscope

The endoscope 5001 includes the lens barrel 5003 to be inserted to the body cavity of the patient 5071 with a region having a predetermined length from the distal end, and a camera head 5005 connected to the base end of the lens barrel 5003. FIG. 1 illustrates an example of the endoscope 5001 having a hard lens barrel 5003, that is, a hard mirror, but the endoscope 5001 may be configured as what is called flexible mirror having a flexible lens barrel 5003.

At a distal end of the lens barrel 5003, an opening through which an objective lens is fitted is provided. A light source device 5043 is connected to the endoscope 5001. Light generated by the light source device 5043 is guided to the distal end of the lens barrel through a light guide extended to the inside of the lens barrel 5003, and is applied toward an observation target in the body cavity of the patient 5071 through the objective lens which may be implemented as a wide-angle lens which is part of the endoscope 5001 and/or the lens barrel 5003. The endoscope 5001 may be a forward-viewing endoscope, a forward-oblique viewing endoscope, or a lateral-viewing endoscope.

An optical system and an imaging element are provided inside the camera head 5005, and reflected light (observation light) from the observation target is condensed to the imaging element by the optical system. The observation light is photoelectrically converted by the imaging element to generate an electric signal corresponding to the observation light, that is, an image signal corresponding to an observation image. The image signal is transmitted to a camera control unit (CCU) 5039 as RAW data. The camera head 5005 has a function for appropriately driving the optical system to adjust the magnification and the focal length.

The camera head 5005 may be provided with a plurality of imaging elements in order to support stereoscopic viewing (3D display), for example. In this case, a plurality of systems of replay optical systems are provided inside the lens barrel 5003 in order to guide observation light to the imaging elements.

Various kinds of devices are mounted in the cart 5037. The CCU 5039 is configured by a central processing unit (CPU) or a graphics processing unit (GPU), and comprehensively controls the operations of the endoscope 5001 and the display device 5041. Specifically, the CCU 5039 performs various kinds of image processing on an image signal received from the camera head 5005 for displaying an image based on the image signal, such as development processing (demosaicing). The CCU 5039 provides the image signal subjected to the image processing to the display device 5041. The CCU 5039 transmits a control signal to the camera head 5005 to control the driving thereof. The control signal may include information on imaging conditions, such as the magnification and the focal length.

Under control of the CCU 5039, the display device 5041 displays an image based on the image signal subjected to image processing by the CCU 5039. For example, when the endoscope 5001 supports high-resolution photographing such as 4K (number of horizontal pixels 3,840×number of vertical pixels 2,160) and 8K (number of horizontal pixels 7,680×number of vertical pixels 4,320) and/or 3D display, a display device capable of high-resolution display and/or 3D display correspondingly may be used as the display device 5041. When the display device 5041 supports high-resolution photographing such as 4K and 8K, if the display device 5041 has a size of 55 inches or more, a higher sense of immersion can be obtained. Depending on the usage, a plurality of display devices 5041 having different resolutions and sizes may be provided.

The light source device 5043 is configured by a light source such as a light emitting diode (LED), and supplies irradiation light for photographing a surgical part to the endoscope 5001.

The arm control device 5045 is configured by a processor such as a CPU. The arm control device 5045 operates in accordance with a predetermined computer program, and controls the driving of the arm portion 5031 in the support arm device 5027 in accordance with a predetermined control method.

An input device 5047 is an input interface for the endoscopic surgical system 5000. A user can input various kinds of information and instructions to the endoscopic surgical system 5000 through the input device 5047. For example, the user inputs various kinds of information on surgery, such as body information on a patient and information on operative procedure of the surgery through the input device 5047. For example, the user inputs, through the input device 5047, an instruction to drive the arm portion 5031, an instruction to change imaging conditions (such as type of irradiation light, magnification, and focal length) by the endoscope 5001, and an instruction to drive the energy treatment tool 5021.

The type of the input device 5047 is not limited, and the input device 5047 may be various kinds of publicly known input devices. As the input device 5047, for example, a mouse, a keyboard, a touch panel, a switch, a foot switch 5057 and/or a lever may be applied. When a touch panel is used as the input device 5047, the touch panel may be provided on a display surface of the display device 5041.

Alternatively, for example, the input device 5047 is a device mounted to a user, such as a glass-type wearable device and a head mounted display (HMD), and various kinds of inputs are made in accordance with the gesture or visual line of the user detected by the device. The input device 5047 includes a camera capable of detecting the motion of the user, and various kinds of inputs are made in accordance with the gesture or visual line of the user detected from video taken by the camera. Furthermore, the input device 5047 includes a microphone capable of collecting voice of the user, and various kinds of inputs are made by voice through the microphone. In this manner, the input device 5047 is configured to input various kinds of information in a contactless manner, and hence particularly a user belonging to a clean area (for example, operator 5067) can operate a device belonging to an unclean area in a contactless manner. The user can operate a device without releasing his/her hand from a holding surgical tool, and hence the convenience for the user is improved.

A treatment tool control device 5049 controls the driving of the energy treatment tool 5021 for cauterizing and incision of tissues or sealing of blood vessels. An insufflation device 5051 sends gas into the body cavity of the patient 5071 through the insufflation tube 5019 in order to expand the body cavity for the purpose of securing the visual field of the endoscope 5001 and securing operating space for the operator. A recorder 5053 is a device capable of recording various kinds of information on surgeries. A printer 5055 is a device capable of printing various kinds of information on surgeries in various kinds of formats, such as text, images, and graphs.

Particularly characteristic configurations of the endoscopic surgical system 5000 are described in more detail below.

Support Arm Device

The support arm device 5027 includes the base portion 5029 as a base, and the arm portion 5031 extending from the base portion 5029. In the illustrated example, the arm portion 5031 includes a plurality of joint portions 5033*a*, 5033*b*, and 5033*c* and a plurality of links 5035*a* and 5035*b* coupled by the joint portion 5033*b*. In FIG. 1, the illustration of the configuration of the arm portion 5031 is simplified for simplicity. In practice, the shapes, numbers, and arrangement of the joint portions 5033*a* to 5033*c* and the links 5035a and 5035b and the directions of rotation axes of the joint portions 5033a to 5033c may be appropriately set such that the arm portion 5031 has a desired degree of freedom. For example, the arm portion 5031 may be preferably configured so as to have six or more degrees of freedom. In this manner, the endoscope 5001 can be freely moved within the movable range of the arm portion 5031, and hence the lens barrel 5003 in the endoscope 5001 can be inserted into the body cavity of the patient 5071 from a desired direction.

The joint portions 5033a to 5033c are provided with actuators, and the joint portions 5033a to 5033c are driven by the actuators to be rotatable about predetermined rotation axes. When the driving of the actuators is controlled by the arm control device 5045, the rotation angles of the joint portions 5033a to 5033c are controlled to control the driving of the arm portion 5031. In this manner, the position and posture of the endoscope 5001 may be controlled. In this case, the arm control device 5045 can control the driving of the arm portion 5031 by various kinds of publicly known control methods, such as force control and position control.

For example, when the operator 5067 appropriately inputs an operation through the input device 5047 (including foot switch 5057), the driving of the arm portion 5031 may be appropriately controlled by the arm control device 5045 in accordance with the operation input such that the position and posture of the endoscope 5001 are controlled. This control enables the endoscope 5001 at the distal end of the arm portion 5031 to move from a desired position to another desired position and to be fixedly supported at the position after the movement. The arm portion 5031 may be operated by what is called "master-slave method". In this case, the arm portion 5031 (slave) may be remotely operated by a user through the input device 5047 (master console) installed at a location away from an operating room or in the operating room.

In the case where force control is applied, the arm control device 5045 may perform what is called "power assist control", in which external force is received from a user and the actuators for the joint portions 5033a to 5033c are driven such that the arm portion 5031 smoothly moves in response to the external force. In this manner, when the user moves the arm portion 5031 while directly touching the arm portion 5031, the user can move the arm portion 5031 with relatively small force. Consequently, the user can move the endoscope 5001 by a more intuitively and simpler operation, and the convenience for the user can be improved.

In general, in endoscopic surgery, the endoscope 5001 is supported and/or operated by a doctor or other medical personnel called a "scopist". On the other hand, the use of the support arm device 5027 enables the position of the endoscope 5001 to be more reliably fixed without manpower, thus stably obtaining images of surgical parts to perform smooth surgeries.

The arm control device 5045 is not necessarily required to be provided on the cart 5037. The arm control device 5045 is not necessarily required to be a single device. For example, the arm control device 5045 may be provided to each of the joint portions 5033a to 5033c in the arm portion 5031 in the support arm device 5027, and the plurality of arm control devices 5045 may cooperate to implement the driving control of the arm portion 5031.

Light Source Device

The light source device 5043 supplies irradiation light for photographing a surgical part to the endoscope 5001. For example, the light source device 5043 is configured by a white light source formed from an LED, a laser light source, or a combination thereof. When a white light source is configured by a combination of RGB laser light sources, the output intensity and output timing of each color (each wavelength) can be controlled with high accuracy, and hence white balance of taken images can be adjusted by the light source device 5043. In this case, by applying laser light beams from the RGB laser light sources to an observation target in a time-division manner and controlling the driving of the imaging element in the camera head 5005 in synchronization with the application timings, images corresponding to RGB can be taken in a time-division manner. This method can obtain a color image without providing a color filter to the imaging element.

The driving of the light source device 5043 may be controlled such that the intensity of output light is changed for every predetermined time. By controlling the driving of the imaging element in the camera head 5005 in synchronization with the timing of changing the intensity of light to acquire images in a time-division manner and combining the images, a high dynamic range image without what is called "crushed shadows" or "blown-out highlights" can be generated.

The light source device 5043 may be configured to supply light in a predetermined wavelength band corresponding to special light observation. In special light observation, for example, what is called "narrow band imaging" is performed, in which the wavelength dependency of absorption of light in body tissues is used, and light in a narrower bandwidth than irradiation light (that is, white light) during normal observation is applied to photograph predetermined tissue such as blood vessels in a mucous membrane surface with high contrast. Alternatively, in special light observation, fluorescent observation for obtaining images by fluorescence generated by application of excitation light may be performed. In fluorescent observation, excitation light can be applied to body tissue and fluorescence from the body tissue can be observed (auto-fluorescence observation) or a reagent such as indocyanine green (ICG) can be locally injected in body tissue and excitation light corresponding to the fluorescent wavelength of the reagent can be applied to the body tissue to obtain a fluorescent image. The light source device 5043 may be capable of supplying narrow band light and/or excitation light that supports such special light observation.

Camera Head and CCU

Figure 2:
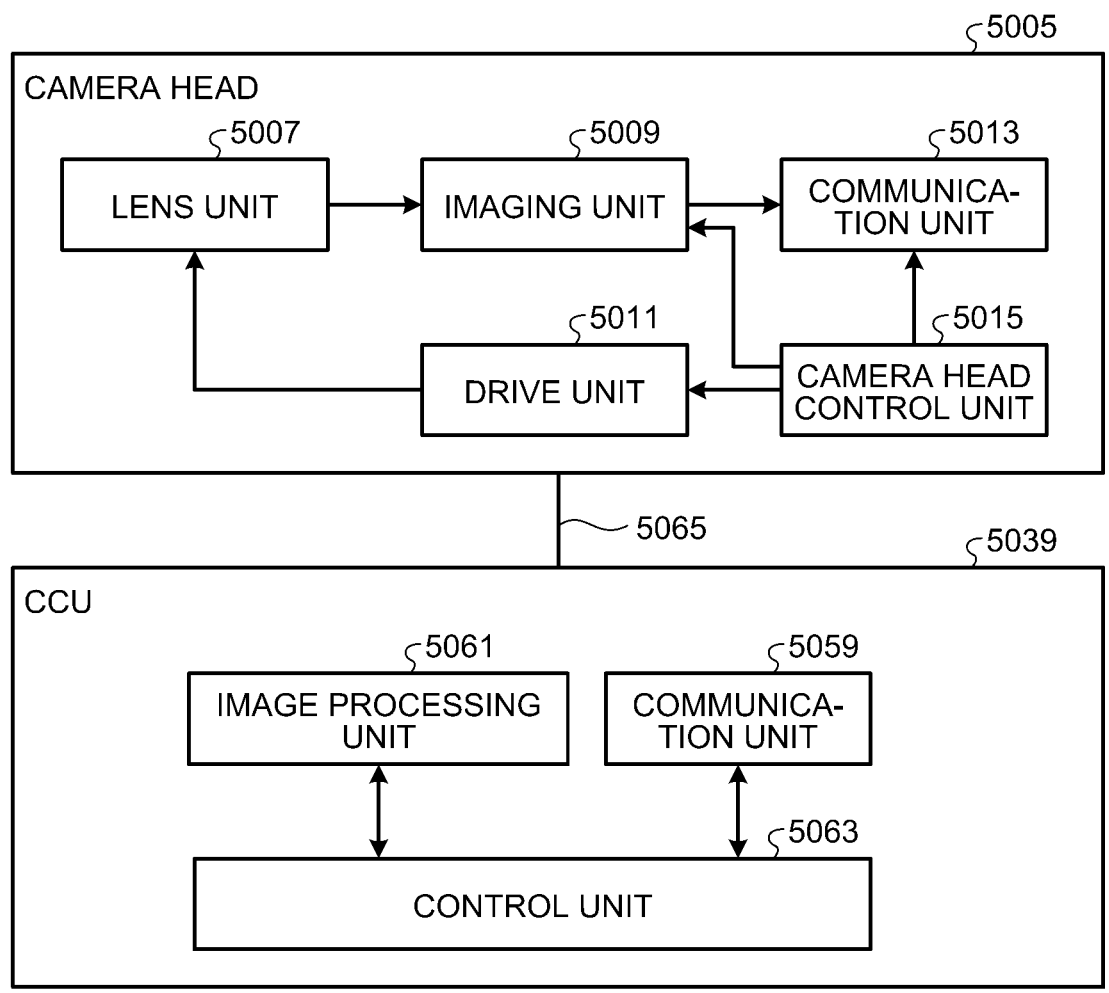
FIG. 2 is a block diagram illustrating an example of functional configurations of a camera head and a camera control unit (CCU) illustrated in FIG. 1.

Referring to FIG. 2, the functions of the camera head 5005 in the endoscope 5001 and the CCU 5039 are described in more detail. FIG. 2 is a block diagram illustrating an example of the functional configurations of the camera head 5005 and the CCU 5039 illustrated in FIG. 1.

Referring to FIG. 2, the camera head 5005 includes, as its functions, a lens unit 5007, an imaging unit 5009, a drive unit 5011, a communication unit 5013, and a camera head control unit 5015. The CCU 5039 includes, as its functions, a communication unit 5059, an image processing unit 5061, and a control unit 5063. The camera head 5005 and the CCU 5039 are connected by a transmission cable 5065 so as to be bidirectionally communicable.

First, the functional configuration of the camera head 5005 is described. The lens unit 5007 is an optical system provided at a connection portion to the lens barrel 5003. Observation light taken from the distal end of the lens barrel 5003 is guided to the camera head 5005, and enters the lens unit 5007. The lens unit 5007 is configured by a combination of a plurality of lenses including a zoom lens and a focus lens. Optical characteristics of the lens unit 5007 are adjusted such that observation light is condensed on a light receiving surface of an imaging element in the imaging unit

5009. The zoom lens and the focus lens are configured such that the positions thereof on an optical axis can move in order to adjust the magnification and the focal point of taken images.

The imaging unit 5009 is configured by an imaging element, and is disposed behind the lens unit 5007. Observation light that has passed through the lens unit 5007 is condensed on a light receiving surface of the imaging element, and subjected to photoelectric conversion such that an image signal corresponding to an observation image is generated. The image signal generated by the imaging unit 5009 is provided to the communication unit 5013.

Examples of the imaging element constituting the imaging unit 5009 include an image sensor of a complementary metal oxide semiconductor (CMOS) type, and an imaging element having Bayer arrangement capable of color photographing is used. As the imaging element, for example, an imaging element that supports photographing with high resolution of 4 K or more may be used. When an image of a surgical part can be obtained with high resolution, the operator 5067 can grasp the situation of the surgical part in more detail and advance a surgery more smoothly.

The imaging element constituting the imaging unit 5009 has a pair of imaging elements for acquiring image signals for right eye and left eye corresponding to 3D display. The 3D display enables the operator 5067 to more accurately grasp the depth of biological tissue in a surgical part. When the imaging unit 5009 is configured by a multiple-type imaging unit, a plurality of systems of lens units 5007 are provided correspondingly to imaging elements.

The imaging unit 5009 is not necessarily provided to the camera head 5005. For example, the imaging unit 5009 may be provided inside the lens barrel 5003 immediately behind the objective lens.

The drive unit 5011 is configured by an actuator. Under control of the camera head control unit 5015, the drive unit 5011 moves the zoom lens and the focus lens in the lens unit 5007 along an optical axis by a predetermined distance. In this manner, the magnification and the focal point of an image taken by the imaging unit 5009 may be adjusted as appropriate.

The communication unit 5013 is configured by a communication device for transmitting and receiving various kinds of information to and from the CCU 5039. The communication unit 5013 transmits an image signal obtained from the imaging unit 5009 to the CCU 5039 through the transmission cable 5065 as RAW data. In this case, it is preferred that the image signal be transmitted by optical communication in order to display the taken image of the surgical part with low latency. The reason is that, in a surgery, the operator 5067 performs a surgery while observing the state of an affected part through a taken image and hence a moving image of the surgical part is required to be displayed in real time as much as possible for a safer and more reliable surgery. When optical communication is performed, the communication unit 5013 is provided with a photoelectric conversion module for converting an electric signal into an optical signal. After an image signal is converted into an optical signal by the photoelectric conversion module, the image signal is transmitted to the CCU 5039 through the transmission cable 5065.

The communication unit 5013 receives, from the CCU 5039, a control signal for controlling the driving of the camera head 5005. For example, the control signal includes information on imaging conditions, such as information for designating a frame rate of a taken image, information for designating an exposure value during imaging, and/or information for designating the magnification and the focal point of a taken image. The communication unit 5013 provides the received control signal to the camera head control unit 5015. The control signal from the CCU 5039 may also be transmitted by optical communication. In this case, the communication unit 5013 is provided with a photoelectric conversion module for converting an optical signal into an electric signal. The control signal is converted into an electric signal by the photoelectric conversion module, and then provided to the camera head control unit 5015.

The above-mentioned imaging conditions, such as the frame rate, the exposure value, the magnification, and the focal point, are automatically set by the control unit 5063 in the CCU 5039 based on an acquired image signal. In other words, what is called "auto exposure (AE) function", "auto focus (AF) function", and "auto white balance (AWB) function" are installed in the endoscope 5001.

The camera head control unit 5015 controls the driving of the camera head 5005 based on a control signal from the CCU 5039 received through the communication unit 5013. For example, the camera head control unit 5015 controls the driving of the imaging element in the imaging unit 5009 based on information for designating the frame rate of a taken image and/or information for designating the exposure during imaging. For example, the camera head control unit 5015 appropriately moves the zoom lens and the focus lens in the lens unit 5007 through the drive unit 5011 based on information for designating the magnification and the focal point of the taken image. The camera head control unit 5015 may further have a function for storing therein information for identifying the lens barrel 5003 and the camera head 5005.

By disposing the configurations such as the lens unit 5007 and the imaging unit 5009 in an airtight structure having high airtightness and waterproof property, the camera head 5005 can be provided with tolerance to autoclave sterilization.

Next, the functional configuration of the CCU 5039 is described. The communication unit 5059 includes a communication device for transmitting and receiving various kinds of information to and from the camera head 5005. The communication unit 5059 receives, from the camera head 5005, an image signal transmitted through the transmission cable 5065. In this case, as described above, the image signal may be preferably transmitted by optical communication. In this case, the communication unit 5059 is provided with a photoelectric conversion module for converting an optical signal into an electric signal so as to support optical communication. The communication unit 5059 provides an image signal converted into an electric signal to the image processing unit 5061.

The communication unit 5059 transmits a control signal for controlling the driving of the camera head 5005 to the camera head 5005. The control signal may be transmitted by optical communication.

The image processing unit 5061 performs various kinds of image processing on an image signal as RAW data transmitted from the camera head 5005. Examples of the image processing include various kinds of publicly known signal processing, such as development processing, image quality improving processing (boosting, super-resolution processing, noise reduction (NR) processing, and/or image stabilization processing), and/or enlarging processing (electronic zooming). The image processing unit 5061 performs detection processing on image signals for AE, AF, and AWB.

The image processing unit 5061 is configured by a processor such as a CPU and a GPU. When the processor operates in accordance with a predetermined computer program, the above-mentioned image processing and detection processing may be performed. In the case where the image processing unit 5061 is configured by a plurality of GPUs, the image processing unit 5061 appropriately divides information on an image signal, and performs image processing by the GPUs in parallel.

The control unit 5063 performs various kinds of control on the imaging of a surgical part by the endoscope 5001 and the displaying of a taken image thereof. For example, the control unit 5063 generates a control signal for controlling the driving of the camera head 5005. In this case, when imaging conditions are input by a user, the control unit 5063 generates a control signal based on the input by the user. Alternatively, when the endoscope 5001 is equipped with the AE function, the AF function, and the AWB function, the control unit 5063 generates a control signal by appropriately calculating the optimal exposure value, focal length, and white balance in accordance with the result of detection processing by the image processing unit 5061.

The control unit 5063 displays an image of the surgical part on the display device 5041 based on an image signal subjected to image processing by the image processing unit 5061. In this case, the control unit 5063 recognizes various kinds of objects in the surgical part image by using various kinds of image recognition technology. For example, the control unit 5063 can recognize surgical tools such as forceps, particular biological sites, bleeding, and mist during the use of the energy treatment tool 5021 by detecting the shape and color of edges of objects included in the surgical part image. When displaying the image of the surgical part on the display device 5041, the control unit 5063 uses the recognition result to display various kinds of surgery assist information on the image of the surgical part in a superimposed manner. The superimposed display of the surgery assist information presented to the operator 5067 enables the operator 5067 to advance a surgery more safely and reliably.

The transmission cable 5065 that connects the camera head 5005 and the CCU 5039 is an electric signal cable supporting communication of electric signals, an optical fiber supporting optical communication, or a composite cable thereof.

In the illustrated example, wired communication using the transmission cable 5065 is performed, but the communication between the camera head 5005 and the CCU 5039 may be performed in a wireless manner. When the communication between the camera head 5005 and the CCU 5039 is performed in a wireless manner, the transmission cable 5065 is not required to be laid in a surgery room, and hence a situation in which the movement of medical staff in the surgery room is hindered by the transmission cable 5065 may be eliminated.

An example of the endoscopic surgical system 5000 to which the technology according to the present disclosure may be applied has been described above. While the endoscopic surgical system 5000 has been described as an example, the system to which the technology according to the present disclosure may be applied is not limited to the example. For example, the technology according to the present disclosure may be applied to an examination flexible endoscope system or a microscopic surgery system.

2. Specific Configuration Example of Support Arm Device

Next, a specific configuration example of the support arm device according to the embodiment of the present disclosure is described in detail. The support arm device described below is an example of a support arm device that supports an endoscope at a distal end of an arm portion, but the present embodiment is not limited to the example. In the case where the support arm device according to the embodiment of the present disclosure is applied to the medical field, the support arm device according to the embodiment of the present disclosure may function as a medical support arm device.

2-1. Outer Appearance of Support Arm Device

Figure 3:
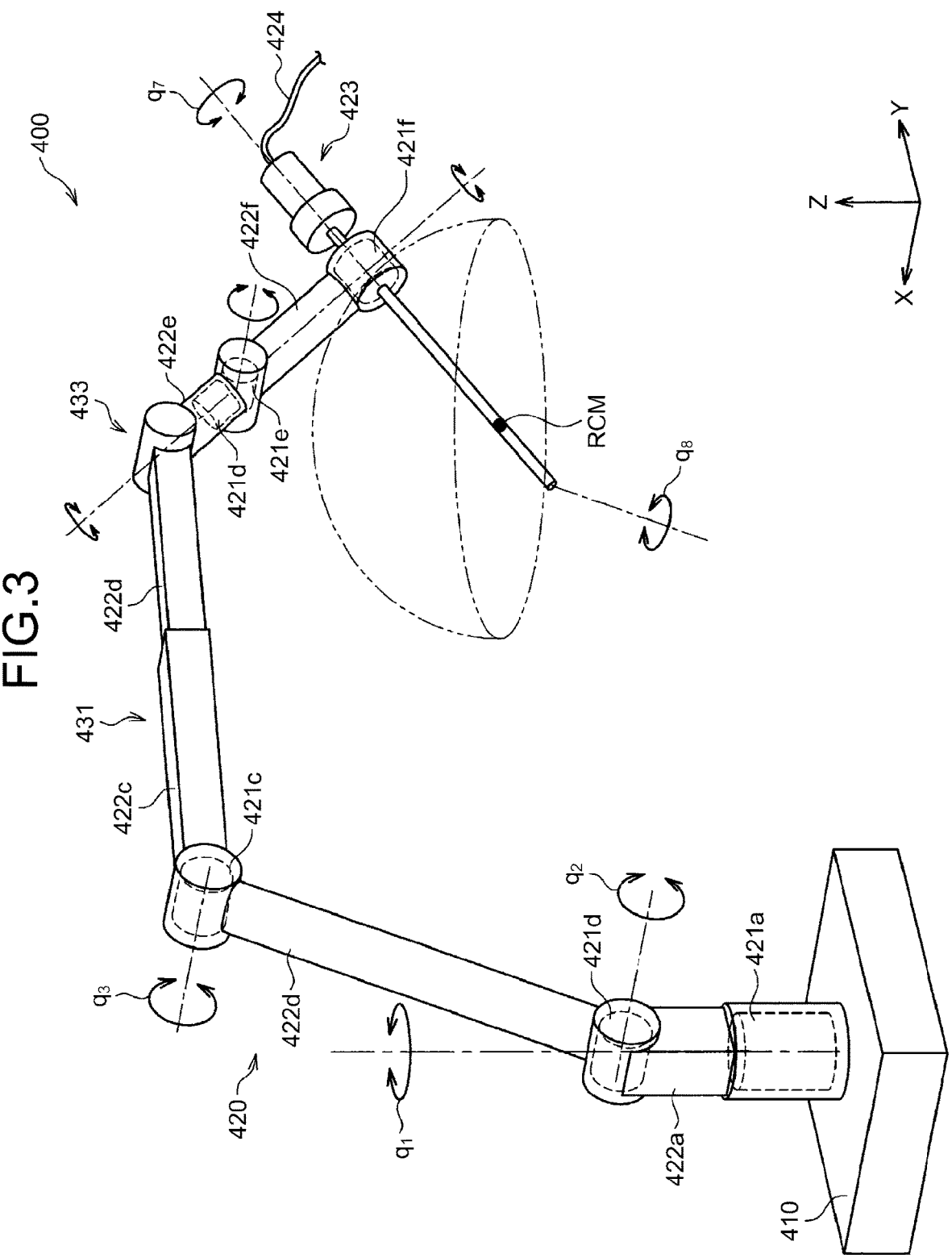
FIG. 3 is a schematic diagram illustrating the outer appearance of a support arm device according to an embodiment of the present disclosure.

First, the schematic configuration of a support arm device 400 according to the present embodiment is described with reference to FIG. 3. FIG. 3 is a schematic diagram illustrating the outer appearance of the support arm device 400 according to the present embodiment.

The support arm device 400 according to the present embodiment includes a base portion 410 and an arm portion 420. The base portion 410 is a base of the support arm device 400, and the arm portion 420 is extended from the base portion 410. Although not illustrated in FIG. 3, a control unit for comprehensively controlling the support arm device 400 may be provided in the base portion 410, and the driving of the arm portion 420 may be controlled by the control unit. The control unit is configured by various kinds of signal processing circuits, such as a CPU and a DSP.

The arm portion 420 includes a plurality of active joint portions 421*a* to 421*f*, a plurality of links 422*a* to 422*f*, and an endoscope device 423 as a distal end unit provided at a distal end of the arm portion 420.

The links 422*a* to 422*f* are substantially rod-like members. One end of the link 422*a* is coupled to the base portion 410 through the active joint portion 421*a*, the other end of the link 422*a* is coupled to one end of the link 422*b* through the active joint portion 421*b*, and the other end of the link 422*b* is coupled to one end of the link 422*c* through the active joint portion 421*c*. The other end of the link 422*c* is coupled to the link 422*d* through a passive slide mechanism 100, and the other end of the link 422*d* is coupled to one end of the link 422*e* through a passive joint portion 433. The other end of the link 422*e* is coupled to one end of the link 422*f* through the active joint portions 421*d* and 421*e*. The endoscope device 423 is coupled to the distal end of the arm portion 420, that is, the other end of the link 422*f* through the active joint portion 421*f*. In this manner, the ends of the links 422*a* to 422*f* are coupled to one another by the active joint portions 421*a* to 421*f*, the passive slide mechanism 100, and the passive joint portion 433 with the base portion 410 as a fulcrum, thereby forming the arm shape extended from the base portion 410.

By controlling the driving of actuators provided to the active joint portions 421*a* to 421*f* in the arm portion 420, the position and posture of the endoscope device 423 are controlled. In the present embodiment, the distal end of the endoscope device 423 enters the body cavity of a patient, which is a surgical site, to photograph a part of the surgical site. The distal end unit provided at the distal end of the arm portion 420 is not limited to the endoscope device 423, and various kinds of medical tools may be connected to the distal end of the arm portion 420 as distal end units. In this manner, the support arm device 400 according to the present embodiment is configured as a medical support arm device provided with a medical tool.

In the following, the support arm device 400 is described by defining the coordinate axes as illustrated in FIG. 3. Corresponding to the coordinate axes, the up-down direction, the front-back direction, and the left-right direction are defined. Specifically, the up-down direction with respect to the base portion 410 installed on the floor surface is defined as the z-axis direction and the up-down direction. A direction which is orthogonal to the z axis and in which the arm portion 420 is extended from the base portion 410 (that is, direction in which endoscope device 423 is located with respect to base portion 410) is defined as the y-axis direction and the front-back direction. Furthermore, a direction orthogonal to the y axis and the z axis is defined as the x-axis direction and the left-right direction.

The active joint portions 421a to 421f couple the links so as to be turnable. The active joint portions 421a to 421f have actuators, and each have a rotation mechanism to be rotationally driven about a predetermined rotation axis when the actuator is driven. By controlling the rotational driving of the active joint portions 421a to 421f, the driving of the arm portion 420, such as extending of the arm portion 420 and shrinking (folding) of the arm portion 420, can be controlled. The driving of the active joint portions 421a to 421f may be controlled by, for example, publicly known whole-body cooperative control and ideal joint control. As described above, the active joint portions 421a to 421f have the rotation mechanisms, and hence in the following description, the driving control of the active joint portions 421a to 421f specifically means the control of the rotation angle and/or generation torque (torque generated by active joint portions 421a to 421f) of the active joint portions 421a to 421f.

The passive slide mechanism 100 is one form of a passive form change mechanism, and couples the link 422c and the link 422d to each other so as to be reciprocatable along a predetermined direction. For example, the passive slide mechanism 100 may couple the link 422c and the link 422d to each other so as to be linearly movable. The reciprocating motion of the link 422c and the link 422d is not limited to the linear motion, and may be the reciprocating motion in a direction to form an arc shape. For example, the reciprocating operation of the passive slide mechanism 100 is performed by a user to vary the distance between the active joint portion 421c on one end side of the link 422c and the passive joint portion 433. In this manner, the entire form of the arm portion 420 may be changed.

The passive joint portion 433 is one form of a passive form change mechanism, and couples the link 422d and the link 422e to each other so as to be turnable. For example, the turning operation of the passive joint portion 433 is performed by a user to vary an angle formed between the link 422d and the link 422e. In this manner, the entire form of the arm portion 420 may be changed.

Herein, "posture of arm portion" refers to the state of the arm portion that may change by the driving control of the actuators provided to the active joint portions 421a to 421f performed by the control unit in the state in which the distance between active joint portions adjacent across one or a plurality of links is constant. In the present disclosure, "posture of arm portion" is not limited to the state of the arm portion that may change by the driving control of the actuators. For example, "posture of arm portion" may be the state of the arm portion that has changed when the joint portions cooperatively operated. In the present disclosure, the arm portion is not necessarily required to have a joint portion. In this case, "posture of arm portion" is the position with respect to a subject or a relative angle with respect to a subject. "Form of arm portion" refers to the state of the arm portion that may change when the distance between active joint portions adjacent across a link or the angle formed by links connecting adjacent active joint portions changes due to the operation of the passive form change mechanism. In the present disclosure, "form of arm portion" is not limited to the state of the arm portion that may change when the distance between active joint portions adjacent across a link or the angle formed by links connecting adjacent active joint portions changes. For example, "form of arm portion" may be the state of the arm portion that may change when the positional relation or angle between joint portions changes due to cooperative operations of joint portions. In the case where the arm portion is not provided with a joint portion, "form of arm portion" may be the state of the arm portion that may change when the position with respect to a target or the relative angle with respect to the target changes.

The support arm device 400 according to the present embodiment have six active joint portions 421a to 421f, and six degrees of freedom are implemented for the driving of the arm portion 420. In other words, the driving control of the support arm device 400 is implemented by the driving control of six active joint portions 421a to 421f by the control unit, but the passive slide mechanism 100 and the passive joint portion 433 are not subjected to the driving control by the control unit.

Specifically, as illustrated in FIG. 3, the active joint portions 421a, 421d, and 421f are provided such that the long-axis direction of the connected links 422a and 422e and the photographing direction of the connected endoscope device 423 match a rotation-axis direction. The active joint portions 421b, 421c, and 421e are provided such that the x-axis direction, which is a direction in which the coupling angle of connected links 422a to 422c, 422e, and 422f and the endoscope device 423 is changed within the y-z plane (plane defined by y axis and z axis), matches the rotation axis direction. In this manner, in the present embodiment, the active joint portions 421a, 421d, and 421f have what is called "yawing" function, and the active joint portions 421b, 421c, and 421e have what is called "pitching" function.

Owing to the above-mentioned configuration of the arm portion 420, in the support arm device 400 according to the present embodiment, six degrees of freedom are implemented for the driving of the arm portion 420, and hence the endoscope device 423 can be freely moved in the movable range of the arm portion 420. In FIG. 3, a hemisphere is illustrated as an example of the movable range of the endoscope device 423. Assuming that the center point RCM (remote center of motion) of the hemisphere is a photographing center of a surgical site photographed by the endoscope device 423, by moving the endoscope device 423 on the spherical surface of the hemisphere while the photographing center of the endoscope device 423 is fixed at the center point of the hemisphere, the surgical site can be photographed from various angles.

The schematic configuration of the support arm device 400 according to the present embodiment has been described above. Next, whole-body cooperative control and ideal joint control for controlling the driving of the arm portion 420 in the support arm device 400, that is, the driving of the active joint portions 421a to 421f, according to the present embodiment are described.

The arm portion 220 in the support arm device 200, which has a plurality of joint portions and six degrees of freedom, has been described, but the present disclosure is not limited thereto. Specifically, the arm portion 220 only needs to have a structure in which the endoscope device 223 or an exoscope is provided at its distal end. For example, the arm portion 220 may have only one degree of freedom such that the endoscope device 223 is driven to move in a direction to enter the body cavity of a patient and a direction to retreat.

3. Basic Configuration of Forward-Oblique Viewing Endoscope

Subsequently, the basic configuration of a forward-oblique viewing endoscope as an example of an endoscope is described.

Figure 4:
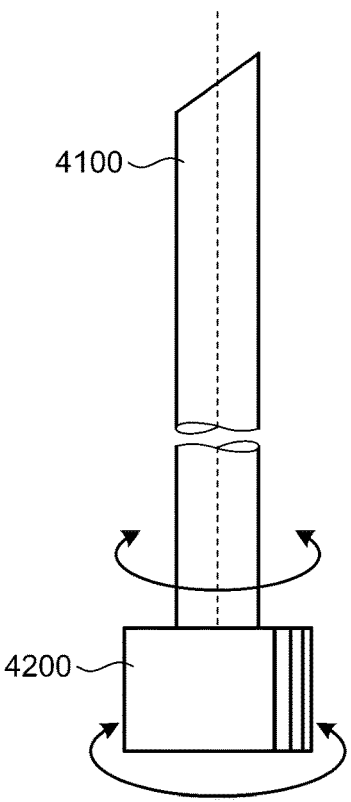
FIG. 4 is a schematic diagram illustrating a configuration of a forward-oblique viewing endoscope according to the embodiment of the present disclosure.

FIG. 4 is a schematic diagram illustrating the configuration of a forward-oblique viewing endoscope 4100 according to one embodiment of the present disclosure. As illustrated in FIG. 4, the forward-oblique viewing endoscope 4100 is mounted to the distal end of a camera head 4200. The forward-oblique viewing endoscope 4100 corresponds to the lens barrel 5003 described above with reference to FIG. 1 and FIG. 2, and the camera head 4200 corresponds to the camera head 5005 described above with reference to FIG. 1 and FIG. 2. The forward-oblique viewing endoscope 4100 and the camera head 4200 are turnable independently from each other. An actuator is provided between the forward-oblique viewing endoscope 4100 and the camera head 4200 similarly to the joint portions 5033a, 5033b, and 5033c, and the forward-oblique viewing endoscope 4100 rotates with respect to the camera head 4200 in response to the driving of the actuator. In this manner, a rotation angle θZ described later is controlled.

The forward-oblique viewing endoscope 4100 is supported by a support arm device 5027. The support arm device 5027 has a function for holding the forward-oblique viewing endoscope 4100 instead of a scopist and moving the forward-oblique viewing endoscope 4100 in response to operation by an operator or an assistant in order to observe a desired site.

Figure 5:
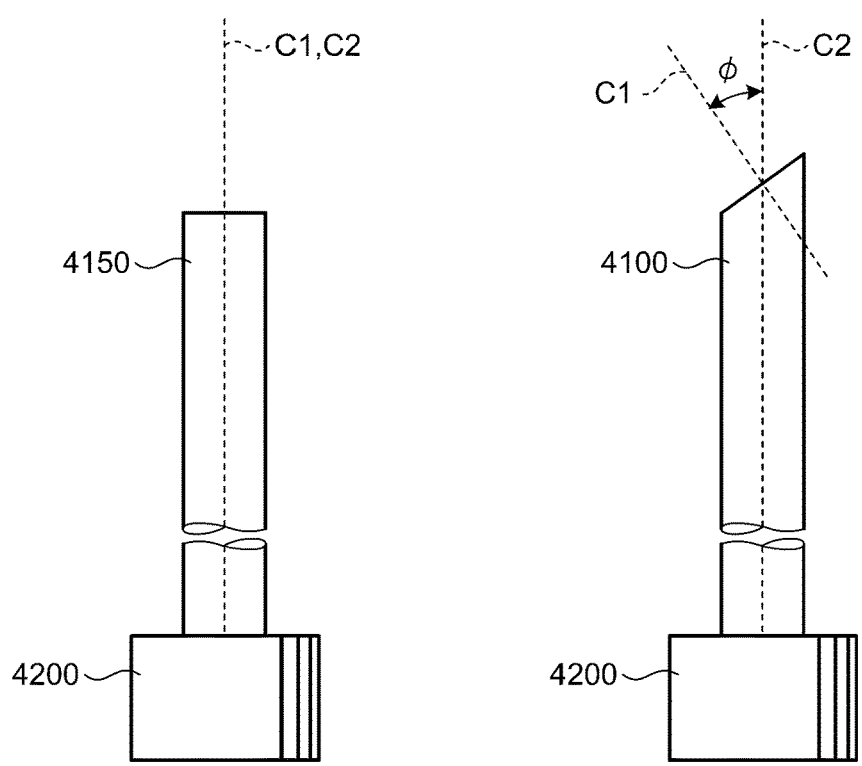
FIG. 5 is a schematic diagram illustrating the forward-oblique viewing endoscope and a forward-viewing endoscope according to the embodiment of the present disclosure for comparison.

FIG. 5 is a schematic diagram illustrating the forward-oblique viewing endoscope 4100 and a forward-viewing endoscope 4150 for comparison. In the forward-viewing endoscope 4150, the direction (C1) of the objective lens to a subject matches the longitudinal direction (C2) of the forward-viewing endoscope 4150. In the forward-oblique viewing endoscope 4100, on the other hand, the direction (C1) of the objective lens to a subject has a predetermined angle φ with respect to the longitudinal direction (C2) of the forward-oblique viewing endoscope 4100. When the angle φ is 90 degrees, the endoscope is called "lateral-viewing endoscope".

4. Medical Observation System

Figure 6:
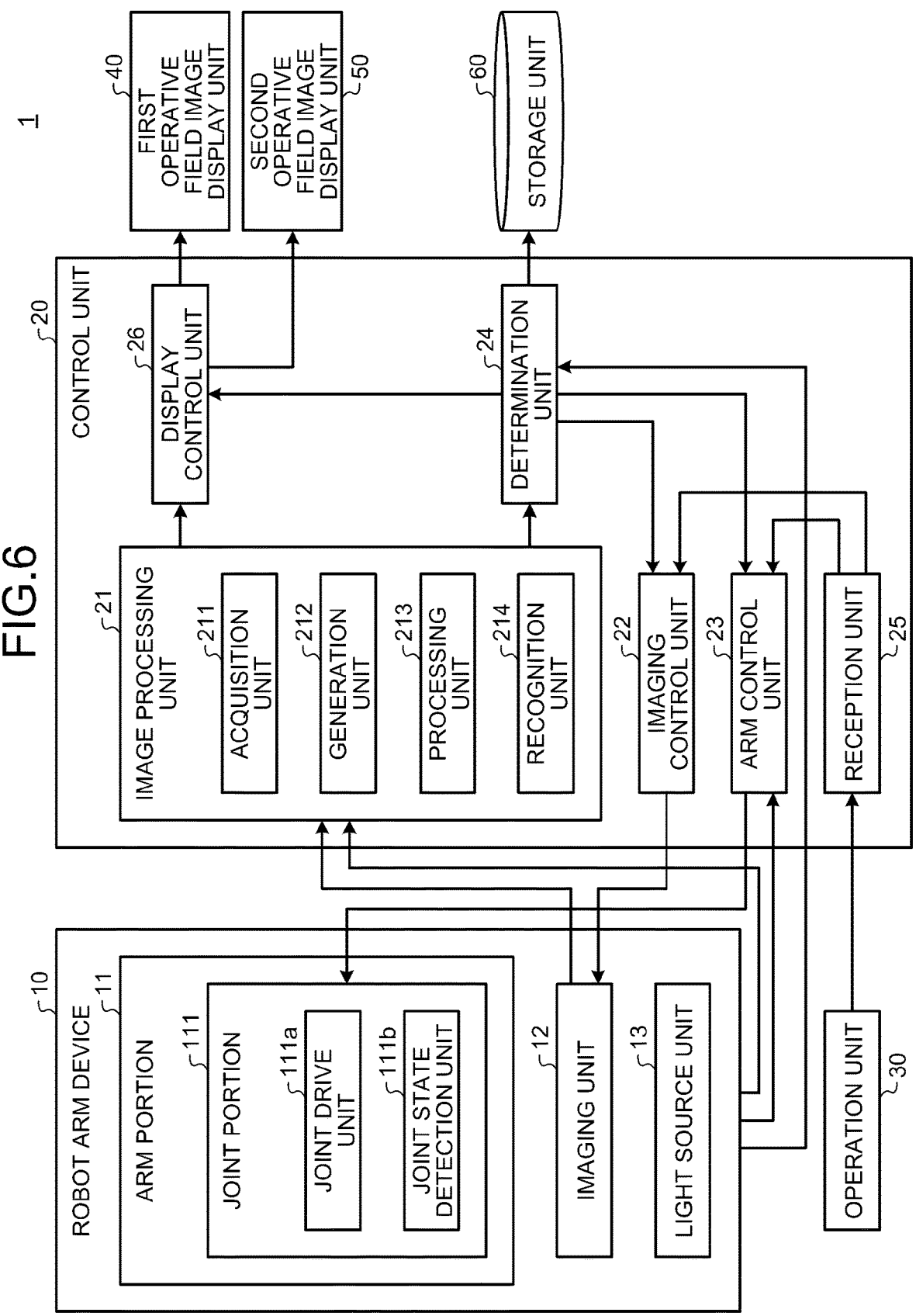
FIG. 6 is a block diagram illustrating an example of a configuration of a medical observation system according to the embodiment of the present disclosure.

Referring to FIG. 6, the configuration of a medical observation system according to the embodiment of the present disclosure is described. FIG. 6 is a block diagram illustrating an example of the configuration of the medical observation system according to the embodiment of the present disclosure.

As illustrated in FIG. 6, the medical observation system 1 includes a robot arm device 10, a control unit 20, an operation unit 30, a first operative field image display unit 40, a second operative field image display unit 50, and a storage unit 60.

Prior to describing the details of the configuration of the medical observation system 1, the outline of processing by the medical observation system 1 is described. In the medical observation system 1, first, an image of the inside of the abdominal cavity of a patient is taken to recognize environments in the abdominal cavity. The medical observation system 1 drives the robot arm device 10 based on the result of recognizing the environments in the abdominal cavity. When the robot arm device 10 is driven, the imaging range in the abdominal cavity changes. When the imaging range in the abdominal cavity has changed, the medical observation system 1 recognizes the changed environments, and drives the robot arm device 10 based on the recognition result. The medical observation system 1 repeats the recognition of the image of the environments in the abdominal cavity and the driving of the robot arm device 10. In other words, the medical observation system 1 executes processing in which the image recognition processing and the processing for controlling the position and posture of the robot arm device 10 are integrated.

The robot arm device 10 has an arm portion 11 (multi-joint arm) as a multi-link structure formed from a plurality of joint portions and a plurality of links, and drives the arm portion within a movable range to control the position and posture of a distal end unit provided to a distal end of the arm portion. The robot arm device 10 corresponds to the support arm device 400 illustrated in FIG. 3.

Figure 7:
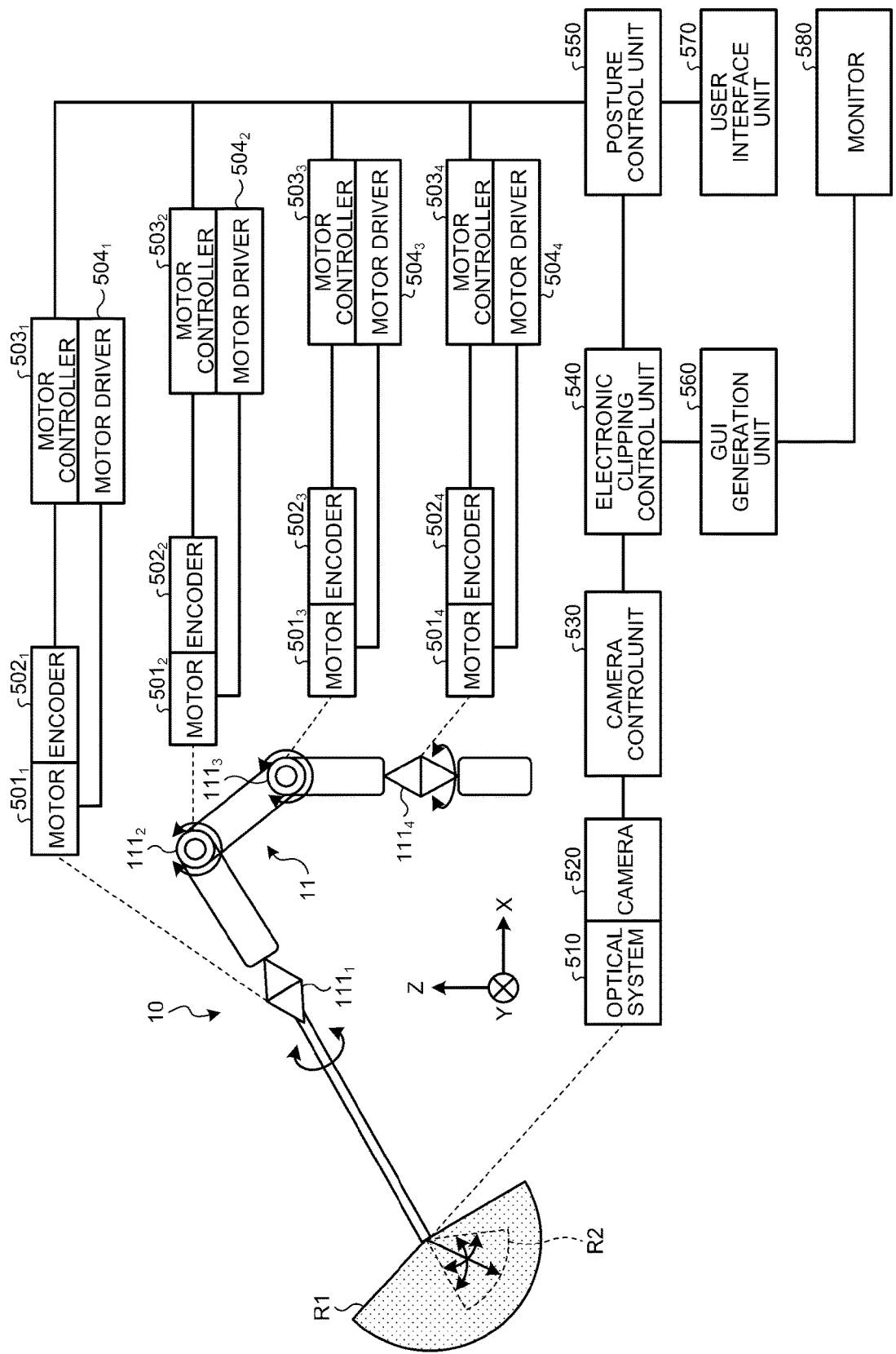
FIG. 7 is a diagram for describing the outline of a configuration of a robot arm device according to the embodiment of the present disclosure.

Referring to FIG. 7, the outline of the configuration of the robot arm device according to the embodiment of the present disclosure is described.

As illustrated in FIG. 7, the arm portion 11 in the robot arm device 10 includes a first joint portion $111_1$, a second joint portion $111_2$, a third joint portion $111_3$, and a fourth joint portion $111_4$. The robot arm device 10 is connected to a camera control unit 530, an electronic clipping control unit 540, a posture control unit 550, a GUI generation unit 560, a user interface unit 570, and a monitor 580.

The first joint portion $111_1$ includes a motor $501_1$, an encoder $502_1$, a motor controller $503_1$, and a motor driver $504_1$. The second joint portion $111_2$ to the fourth joint portion $111_4$ have the same configuration as that of the first joint portion $111_1$, and hence the first joint portion $111_1$ is described below as an example.

The motor $501_1$ is driven under control of the motor driver $504_1$, and drives the first joint portion $111_1$. For example, the motor $501_1$ drives the first joint portion $111_1$ in a direction with arrows attached to the first joint portion $111_1$. The motor $501_1$ drives the first joint portion $111_1$ to control the position and posture of the arm portion 11 and the positions and postures of a lens barrel (optical system 510) and a camera 520 (corresponding to camera head 5005). In the present embodiment, the camera 520 (in this case, for example, corresponding to lens unit 5007 and imaging unit 5009) may be provided at the distal end of the lens barrel as one form of the endoscope.

The encoder $502_1$ detects information on a rotation angle of the first joint portion $111_1$ under control of the motor controller $503_1$. In other words, the encoder $502_1$ acquires information on the posture of the first joint portion $111_1$.

For example, the optical system 510 is a wide-angle optical system including a wide lens. For example, the camera 520 takes an image of an object to be photographed, such as an organ of a patient and a medical tool used for treatment. As described later, in the present disclosure, for example, a display target region R2 desired by a user is clipped from a wide-angle visual field R1 to generate a second operative field image.

The camera control unit 530 corresponds to the CCU 5039 illustrated in FIG. 2. In other words, the camera control unit 530 comprehensively controls the operations of imaging processing by the camera 520 and video processing displayed on the monitor 580.

The electronic clipping control unit 540 clips a predetermined region from video in which an object to be photographed is taken, which has been received from the camera control unit 530, and outputs the clipped data to the GUI generation unit 560. The processing for clipping a predetermined region from video in which an object to be photographed is taken is described later.

The GUI generation unit 560 generates video data obtained by performing various kinds of processing on the video clipped by the electronic clipping control unit 540, and outputs the video data to the monitor 580. In this manner, the monitor 580 displays various kinds of video generated by the GUI generation unit 560. A part or both of the electronic clipping control unit 540 and the GUI generation unit 560 may be provided in the camera control unit 530.

The posture control unit 550 controls the position and posture of the arm portion 11. Specifically, the posture control unit 550 controls the motor controllers $503_1$ to $503_4$ and the motor drivers $504_1$ to $504_4$ to control the first joint portion $111_1$ to the fourth joint portion $111_4$. In this manner, the posture control unit 550 controls the position and posture of the arm portion 11. The posture control unit 550 may be included in the camera control unit 530.

The user interface unit 570 receives various kinds of operations from a user. For example, the user interface unit 570 receives an operation for controlling the position and posture of the arm portion 11. The user interface unit 570 outputs an operation signal corresponding to the received operation to the posture control unit 550. In this case, the posture control unit 550 controls the first joint portion $111_1$ to the fourth joint portion $111_4$ to control the position and posture of the arm portion 11 in accordance with the operation received from the user interface unit 570.

In the robot arm device 10, the electronic degree of freedom for changing the visual line by clipping a camera image taken by the camera 520 and the degrees of freedom by the actuators in the arm portion 11 are all treated as the degrees of freedom of the robot. In this manner, motion control in which the electronic degree of freedom for changing the visual line and the degrees of freedom by the actuators cooperate can be implemented.

Figure 8:
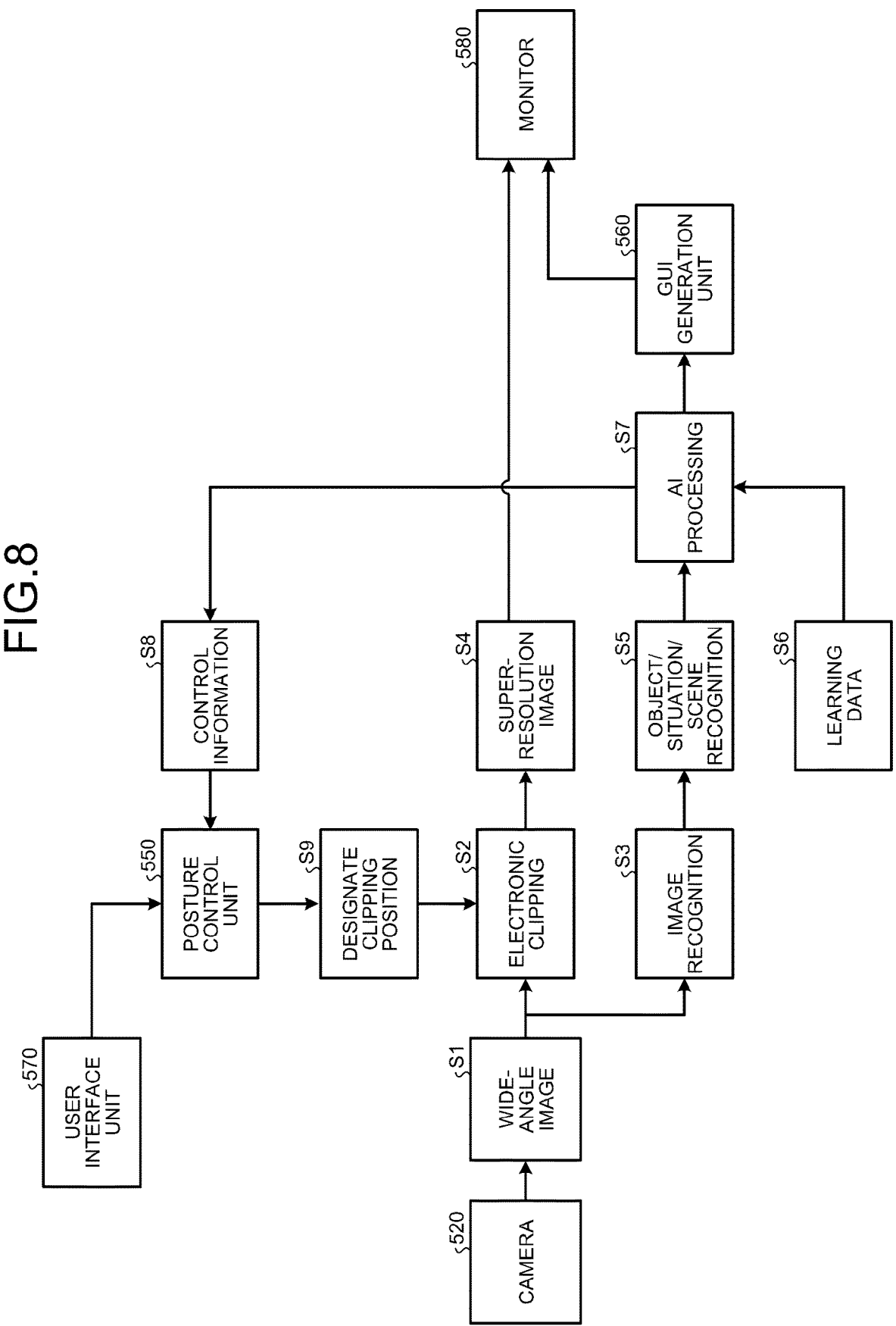
FIG. 8 is a diagram for describing the outline of the flow of processing by a medical observation system 1 according to the embodiment of the present disclosure.

Referring to FIG. 8, the outline of the flow of processing by the medical observation system 1 according to the embodiment of the present disclosure is described.

As described above, the medical observation system 1 executes processing in which image recognition processing and processing for controlling the position and posture of the robot arm device 10 are integrated.

First, in the medical observation system 1, a wide-angle image of an object to be photographed is taken by the camera 520 (Step S1). Based on the wide-angle image taken by the camera 520, electronic clipping processing (Step S2) for clipping video to be visually recognized by a doctor and image recognition processing (Step S3) for recognizing an operative field are executed. The processing at Step S2 and the processing at Step S3 may be executed in parallel.

Super-resolution processing may be executed on the video electronically clipped at Step S2 in order to make it easier for the doctor to visually recognize the video so as to generate a super-resolution image (Step S4). The generated image is displayed on the monitor 580.

After the image recognition processing is executed at Step S3, recognition results of various kinds of objects, scenes, and situations included in the image are output (Step S5). Information on the recognition results is used when artificial intelligence (AI) processing is executed.

To autonomously control the position and posture of the camera 520, data on a surgery being implemented is input to a learned model (AI) in which data on various kinds of surgeries as learning data has been learned in advance (Step S6). Examples of the data on various kinds of surgeries include information on endoscope images, steering data on endoscopes by doctors, operating information on the robot arm device 10, and information on the positions and postures of the arm portion 11. Details of the learned model are described later.

Based on the information on various kinds of recognition results recognized at Step S5 and the data on a surgery input at Step S6, AI processing for autonomously controlling the position and posture of the camera 520 is executed (Step S7). As a result of the AI processing, control information for autonomously controlling the position of the camera 520 is output (Step S8). The wide-angle image used in the image recognition processing at Step S3 is input to the GUI generation unit 560. In this manner, the GUI generation unit 560 displays a wide-angle image of the operative field.

The control information output at Step S8 is input to the posture control unit 550. The posture control unit 550 controls the position and posture of the camera 520. The position and posture of the camera 520 may be designated by the user interface unit 570.

Based on the position and posture controlled by the posture control unit 550, a clipping position in the wide-angle image is determined. The clipping position is designated by the determined clipping position (Step S9). In this manner, the wide-angle image taken by the camera 520 is clipped again.

In the present disclosure, the processing illustrated in FIG. 8 is repeated to execute the processing in which the image recognition processing and the processing for controlling the position and posture of the robot arm device 10 are integrated.

Referring to FIG. 6 again, the arm portion 11 is a multi-link structure formed from joint portions and links, and the driving thereof is controlled under control of an arm control unit 23. The arm portion 11 corresponds to the arm portion 420 illustrated in FIG. 3. In FIG. 6, the configuration of one joint portion 111 is illustrated as a representative of the joint portions.

An imaging unit 12 is provided at the distal end of the arm portion 11, and takes images of various kinds of objects to be imaged. For example, the imaging unit 12 takes an operative field image including various kinds of medical tools and organs in the abdominal cavity of a patient. The operative field image taken by the imaging unit 12 is also called "first operative field image". Specifically, the imaging unit 12 is a camera capable of photographing a photographing target in the form of moving image or still image. More specifically, the imaging unit 12 is a wide-angle camera configured by a wide-angle optical system. In other words, the first operative field image is an operative field image taken by a wide-angle camera. For example, the angle of field of a normal endoscope is about 80°, and the angle of field of the imaging unit 12 according to the present embodiment may be 140°. The angle of field of the imaging unit 12 may be smaller than 1400 or 1400 or more as long as being more than 80°. The imaging unit 12 transmits an electric signal (image signal) corresponding to a taken image to the control unit 20. In FIG. 6, the imaging unit 12 is not necessarily required to be included in the robot arm device, and the form thereof is not limited as long as the imaging unit 12 is supported by the arm portion 11.

Figure 9:
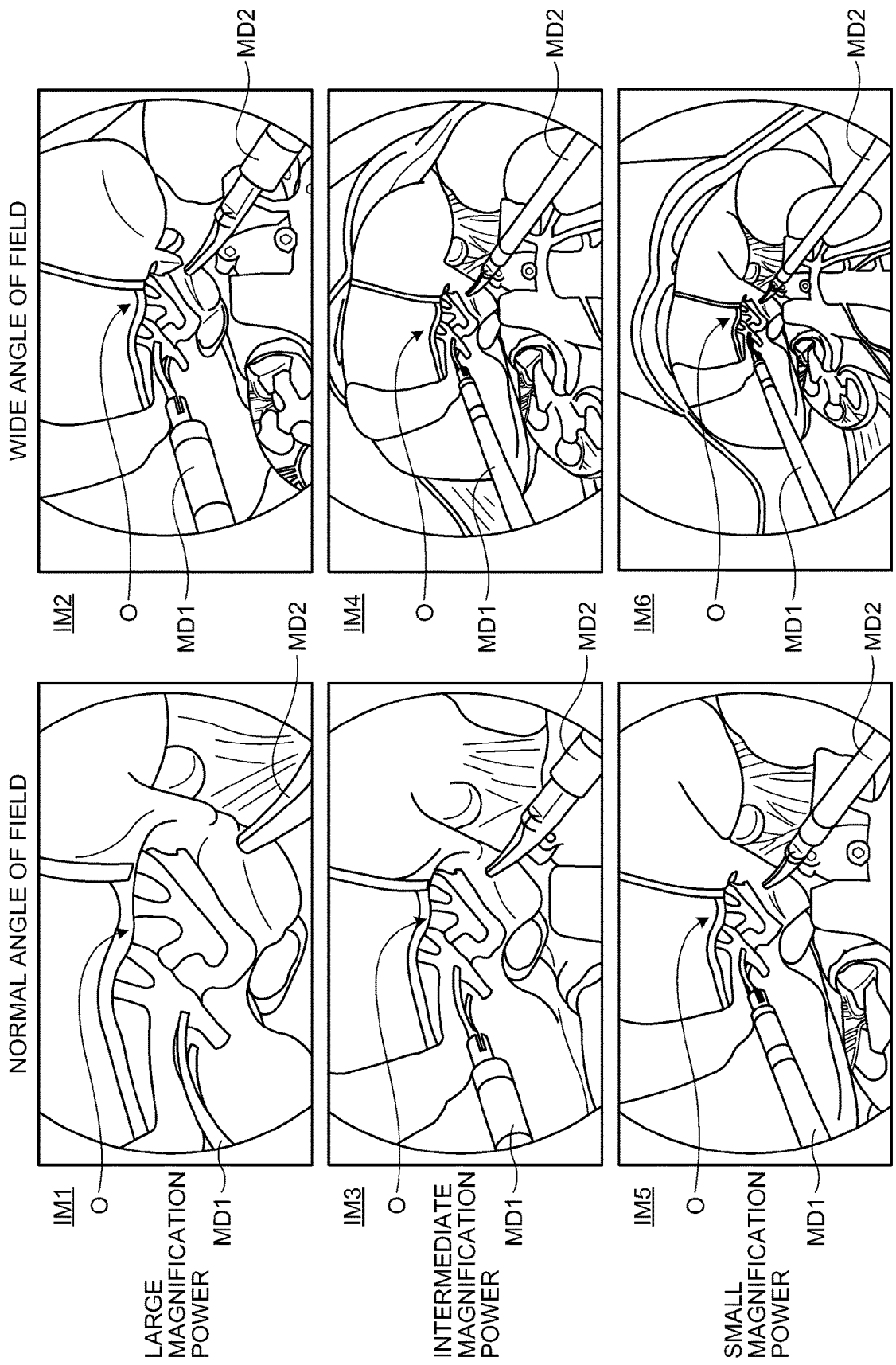
FIG. 9 is a diagram for describing an operative field image taken by an imaging unit according to the embodiment of the present disclosure.

Referring to FIG. 9, an example of an operative field image taken by the imaging unit 12 is described. FIG. 9 is a diagram for describing operative field images taken by the imaging unit 12.

FIG. 9 illustrates an operative field image IM1, an operative field image IM3, and an operative field image IM5 taken by the imaging unit 12 having a normal angle of field. FIG. 9 also illustrates an operative field image IM2, an operative field image IM4, and an operative field image IM6 taken by the imaging unit 12 having a wide angle of field. The operative field image IM1 to the operative field image IM6 are images obtained by photographing the same operative field in which an organ O is treated by a medical tool MD1 and a medical tool MD2. The operative field image IM1 and the operative field image IM2 are operative field images with a large magnification power. The operative field image IM3 and the operative field image IM4 are operative field images with an intermediate magnification power. The operative field image IM5 and the operative field image IM6 are operative field images with a small magnification power.

The operative field image IM1 and the operative field image IM2 with a large magnification power are compared. End effectors of the medical tool MD1 and the medical tool MD2 partly appear in the operative field image IM1, but the entire end effectors of the medical tool MD1 and the medical tool MD2 appear in the operative field image IM2. Thus, even when the operative field is most enlarged, a doctor can grasp the whole of the end effectors of the medical tool MD1 and the medical tool MD2 by referring to the operative field image IM2. Because the entire end effectors of the medical tool MD1 and the medical tool MD2 do not appear in the operative field image IM1 with a large magnification power, the recognition accuracy at the ends of the screen tends to reduce when image recognition processing is executed to recognize the type of the medical tool. On the other hand, the entire medical tool MD1 and the entire medical tool MD2 appear in the operative field image IM2, and hence the recognition accuracy of the type of the medical tool for the medical tool MD1 and the medical tool MD2 improves when the image recognition processing is executed.

The entire operative field appears in the operative field image IM6 with a small magnification power. Thus, the doctor can grasp the whole of environments of the operative field by referring to the operative field image IM6.

In other words, in the present disclosure, a wide field of view can be obtained by using a wide-angle lens. When the zooming function of a conventional endoscope is used to approach an object, the entire of a recognition target located at a screen end cannot be visually recognized in its angle of field, and hence the recognition rate may decrease, which may affect the controllability of the arm portion 11. On the other hand, in the present disclosure, the use of the wide-angle lens can reduce an area that cannot be visually recognized at a screen end and improve the recognition rate. Consequently, the present disclosure can improve the controllability of the arm portion 11 as a result of the improved recognition rate.

A light source unit 13 applies light to an object to be imaged the imaging unit 12. For example, the light source unit 13 can be implemented by a light emitting diode (LED) for a wide-angle lens. For example, the light source unit 13 may be configured by a combination of a normal LED and a lens to diffuse light. The light source unit 13 may be configured such that light transmitted through an optical fiber is diffused by a lens (for wider angle). The light source unit 13 may be configured such that the optical fiber itself is directed in a plurality of directions to increase the irradiation range. In FIG. 6, the light source unit 13 is not necessarily required to be included in the robot arm device 10, and the form of the light source unit 13 is not limited as long as irradiation light can be guided to the imaging unit 12 supported by the arm portion 11.

The joint portion 111 couples the links in the arm portion 11 so as to be turnable, and the rotational driving of the joint portion 111 is controlled to drive the arm portion 11 under control of the arm control unit 23. The joint portion 111 corresponds to the active joint portions 421a to 421f illustrated in FIG. 3. The joint portion 111 has an actuator.

The joint portion 111 has a joint drive unit 111a and a joint state detection unit 111b.

The joint drive unit 111a is a drive mechanism for the actuator in the joint portion 111. When the joint drive unit 111a is driven, the joint portion 111 is rotationally driven. The joint drive unit 111a corresponds to the motor $501_1$ illustrated in FIG. 7. The driving of the joint drive unit 111a is controlled by the arm control unit 23. For example, the joint drive unit 111a has a configuration corresponding to a motor and a motor driver, and the driving of the joint drive unit 111a corresponds to the driving of the motor by the motor driver with a current amount corresponding to an instruction from the arm control unit 23.

The joint state detection unit 111b detects the state of the joint portion 111. The state of the joint portion 111 may mean the state of motion of the joint portion 111. Examples of the state of the joint portion 111 include information on the rotation angle, rotation angular velocity, rotation angular acceleration, and generation torque of the joint portion 111. The joint state detection unit 111b corresponds to the encoder $502_1$ illustrated in FIG. 7. In the present embodiment, the joint state detection unit 111b has a rotation angle detection unit for detecting the rotation angle of the joint portion 111 and a torque detection unit for detecting generation torque and external torque of the joint portion 111. The rotation angle detection unit and the torque detection unit correspond to an encoder and a torque sensor for the actuator, respectively. The joint state detection unit 111b transmits the detected state of the joint portion 111 to the control unit 20.

For example, the control unit 20 is implemented when a central processing unit (CPU) or a micro processing unit (MPU) executes a computer program stored in a storage unit (not shown) (for example, computer program according to the present invention) by using a random access memory (RAM) as a workspace. The control unit 20 is a controller, and may be implemented by an integrated circuit such as an application specific integrated circuit (ASIC) or a field programmable gate array (FPGA). The control unit 20 includes an image processing unit 21, an imaging control unit 22, the arm control unit 23, a determination unit 24, a reception unit 25, and a display control unit 26.

The image processing unit 21 executes various kinds of processing on an imaging target imaged by the imaging unit 12. The image processing unit 21 includes an acquisition unit 211, a generation unit 212, a processing unit 213, a recognition unit 214, and an evaluation unit 215.

The acquisition unit 211 acquires various kinds of images. For example, the acquisition unit 211 acquires an image of an imaging target imaged by the imaging unit 12. For example, the acquisition unit 211 acquires a first operative field image in the abdominal cavity of a patient imaged by the imaging unit 12.

The generation unit 212 generates various kinds of images based on the first operative field image taken by the imaging unit 12. For example, the generation unit 212 generates an image about a display target region in the first operative field image, which is a region of interest (ROI) for a doctor. For example, the display target region may be determined by recognition results of the recognition unit 214. For example, the display target region may be determined by the determination unit 24. For example, the display target region may be designated by a doctor by using the operation unit 30. For example, the generation unit 212 generates an image about the display target region by clipping the display target region from the first operative field image. Specifically, the generation unit 212 generates an image by clipping and enlarging the display target region from the first operative field image. In this case, the generation unit 212 may change the clipping position in accordance with the position and posture of the arm portion 11. Specifically, for example, the generation unit 212 changes the clipping position such that an image displayed on a display screen does not change when the position and posture of the arm portion 11 change. The image generated by the generation unit 212 is referred to as "second operative field image".

Figure 10:
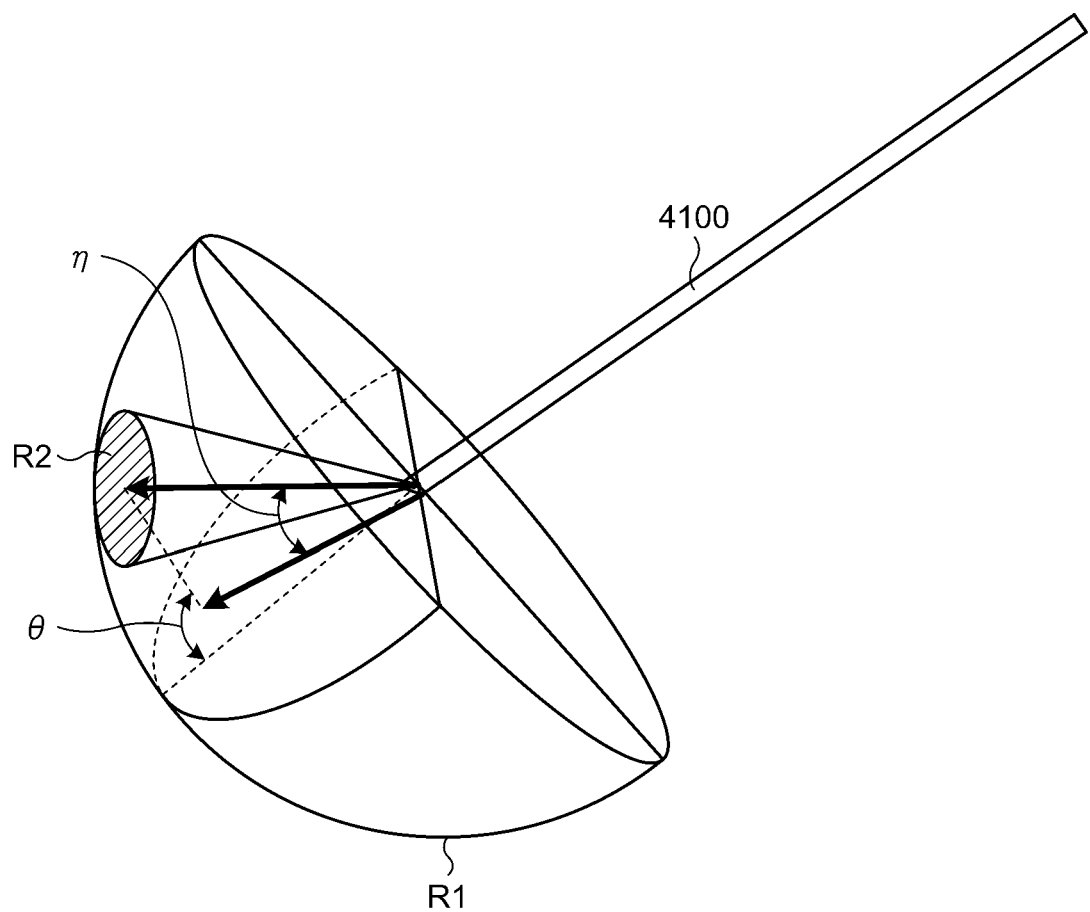
FIG. 10 is a diagram for describing a first operative field image and a second operative field image according to the embodiment of the present disclosure.

Referring to FIG. 10, the first operative field image and the second operative field image are described.

As illustrated in FIG. 10, the imaging unit 12 is provided at a distal end portion of the forward-oblique viewing endoscope 4100. The imaging unit 12 images a wide-angle visual field R1 of a hemisphere (2a steradians). The generation unit 212 clips a display target region R2 desired by a user from the wide-angle visual field R1 to generate a second operative field image. Specifically, the generation unit 212 generates the second operative field image by freely setting the pitch angle θ, the roll angle 11, and the angle of field. The generation unit 212 generates the second operative field image by zooming in or out the display target region R2.

Conventionally, the motion of three degrees of freedom of pitch, roll, and zoom in a forward-viewing endoscope and the motion of four degrees of freedom of pitch, roll, zoom, and yaw in a forward-oblique viewing endoscope are implemented by changing the position and posture of the forward-viewing endoscope or the forward-oblique viewing endoscope by using the mechanical degree of freedom outside the body of a patient. In the present disclosure, on the other hand, the configuration as illustrated in FIG. 10 is provided, and hence the same motion as conventionally required can be implemented by a system having three electronic degrees of freedom of pitch, roll, and zoom without using the mechanical motion outside the body. The look-around operation with a constant distance to a target, which has a limitation by a conventional endoscope, can be implemented. For example, conventionally, when look-around operation is implemented while tracking a point of an observation target, the observation axis of the forward-oblique viewing endoscope 4100 needs to be moved in a conical pattern while being directed to the point. In the present disclosure, on the other hand, the posture in the look-around operation with a constant distance to an object can be freely taken in the wide-angle visual field R1 without moving the forward-oblique viewing endoscope 4100 in a conical pattern. In such motion that the look-around direction is changed while zooming the forward-oblique viewing endoscope 4100 in the observation axis direction, the object can be looked around while keeping the magnification power of the object constant by adding electronic zoom operation. In the present disclosure, the pitch and roll operation of the forward-oblique viewing endoscope 4100 can be electronically executed, and hence the interference between the pitch and roll operation of the forward-oblique viewing endoscope 4100 and the operation by a doctor can be prevented. In this manner, the operability of the doctor is improved. By electronically executing the pitch and roll operation of the forward-oblique viewing endoscope 4100, the operation of manually operating the forward-oblique viewing endoscope 4100 by the doctor can be eliminated. In this manner, the operability of the doctor can be improved.

Figure 11A:
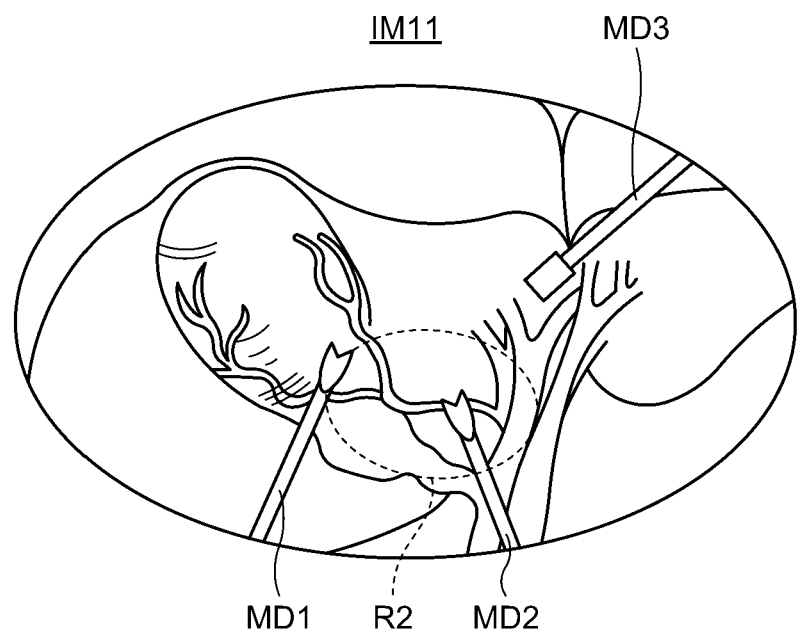
FIG. 11A is a diagram illustrating the first operative field image according to the embodiment of the present disclosure.
Figure 11B:
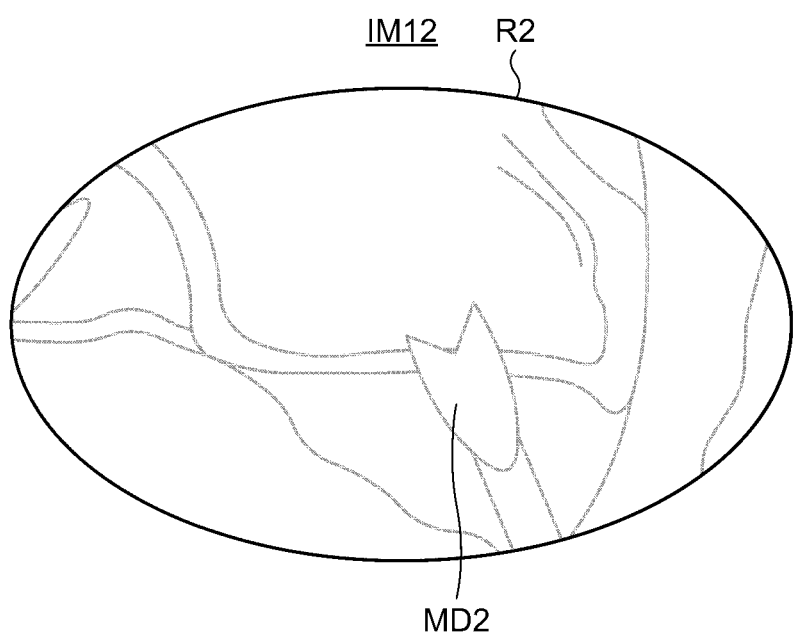
FIG. 11B is a diagram illustrating the second operative field image according to the embodiment of the present disclosure.

Referring to FIG. 11A and FIG. 11B, processing for generating a second operative field image based on a first operative field image is described. FIG. 11A is a diagram illustrating the first operative field image. FIG. 11B is a diagram illustrating the second operative field image.

FIG. 11A illustrates a first operative field image IM11. The first operative field image IM11 is an image that captures how an organ of a patient is treated, and includes a medical tool MD1, a medical tool MD2, and a medical tool MD3. In the first operative field image IM11, a location where the organ is treated by the medical tool MD2 is a display target region R2.

The generation unit 212 clips the display target region R2 from the first operative field image IM2. As illustrated in FIG. 11B, the generation unit 212 enlarges the clipped display target region R2 to generate a second operative field image IM12.

Referring to FIG. 6 again, the processing unit 213 performs various kinds of processing on the first operative field image and the second operative field image. For example, the processing unit 213 may perform image quality improving processing on the second operative field image. For example, the processing unit 213 may perform super-resolution processing as image quality improving processing on the second operative field image. The processing unit 213 may perform boosting, noise reduction (NR) processing, image stabilization, and luminance correction processing as image quality improving processing on the second operative field image. For example, the processing unit 213 may perform the same image processing as that for the second operative field image on the first operative field image. In the present disclosure, the image quality improving processing is not limited to the above, and may include other various kinds of processing.

Figure 12:
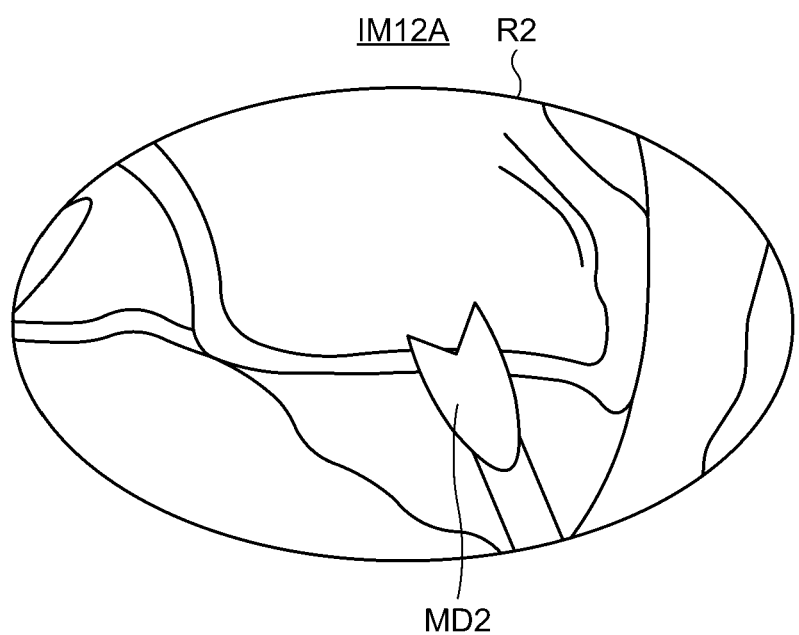
FIG. 12 is a diagram for describing processing performed on the second operative field image according to the embodiment of the present disclosure.

Referring to FIG. 12, the processing performed on the second operative field image is described. FIG. 12 is a diagram for describing the processing performed on the second operative field image.

A second operative field image IM12A illustrated in FIG. 12 is an image obtained after the processing unit 213 performs image quality improving processing on the second operative field image IM12 illustrated in FIG. 11B. After the processing unit 213 performs the image quality improving processing, high image quality video of the display target region can be provided to the doctor. Consequently, the doctor can easily grasp the operative field by referring to the second operative field image IM12A. As described above, the processing unit 213 may perform boosting, NR processing, or image stabilization processing. By performing boosting, an image in which color in a particular bandwidth is emphasized can be provided to the doctor. Consequently, the doctor can easily recognize the difference in color in the operative field. By performing NR processing, random noise included in the image can be removed. Consequently, the doctor can easily grasp the operative field. By performing image stabilization, blur included in the image can be corrected. Consequently, the doctor can easily grasp the operative field.

Referring to FIG. 6 again, the processing unit 213 may generate a third operative field image by performing resolution decreasing processing on the first operative field image. For example, the processing unit 213 may generate the third operative field image by deteriorating the image quality of the first operative field image. The processing unit 213 can reduce the volume of the operative field image by generating the third operative field image. For example, the processing unit 213 may generate a third operative field image having a visual field different from the second operative field image. The processing unit 213 may also perform image quality decreasing processing on the second operative field image. Consequently, the volume of the operative field image can be further reduced.

The processing unit 213 may process a wide-angle first operative field image. For example, the processing unit 213 may correct the first operative field image. For example, the processing unit 213 may correct distortion at an end of the first operative field image. Consequently, the recognition accuracy of the first operative field image by the recognition unit 214 can be improved. By processing the first operative field image by the processing unit 213, the generation unit 212 generates a second operative field image based on the corrected first operative field image. Consequently, the image quality of the second operative field image can be improved.

When the generation unit 212 generates a second operative field image, the processing unit 213 may change the type of correction on the second operative field image depending on the clipping position of the second operative field image in the first operative field image. In other words, the processing unit 213 may change the correction contents each time the clipping position is changed. For example, the processing unit 213 may change the strength of the distortion correction depending on the clipping position. Specifically, the processing unit 213 may perform correction by increasing the strength more at the center region as approaching the end of the second operative field image. The processing unit 213 may or may not perform correction by decreasing the strength at the center region of the second operative field image. In this manner, the processing unit 213 can perform the optimal correction on the second operative field image depending on the clipping position. As a result, the recognition accuracy of the second operative field image by the recognition unit 214 can be improved. In general, the distortion becomes larger as approaching the end of the wide-angle image, and hence by changing the strength of correction depending on the clipping position, the second operative field image that makes it easier for the doctor to grasp the situation of the operative field without any feeling of discomfort can be generated.

The processing unit 213 may change the type of correction on the second operative field image depending on the position and posture of the arm portion 11. In other words, the processing unit 213 may change the correction contents each time the position and posture of the arm portion 11 are changed. In this manner, the processing unit 213 can perform the optimal correction on the second operative field image depending on the position and posture of the arm portion 11. As a result, the recognition accuracy of the second operative field image by the recognition unit 214 can be improved.

The processing unit 213 may change processing performed on the second operative field image based on information input to the control unit 20. Specifically, for example, the processing unit 213 may change image processing performed on the second operative field image based on at least one of information on the motion of the joint portion 111 in the arm portion 11, the recognition result of operative field environments based on the first operative field image, and an object and a treatment status included in the first operative field image. The processing unit 213 changes the image processing depending on various situations, and hence the doctor can easily recognize the second operative field image.

The recognition unit 214 recognizes various kinds of information based on the first operative field image. For example, the recognition unit 214 recognizes various kinds of information on medical tools included in the first operative field image. For example, the recognition unit 214 recognizes various kinds of information on an organ included in the first operative field image.

Referring to FIG. 13A, FIG. 13B, FIG. 13C, FIG. 13D, and FIG. 13E, information recognized by the recognition unit 214 is described. FIG. 13A to FIG. 13E are diagrams for describing information recognized by the recognition unit 214.

Figure 13A:
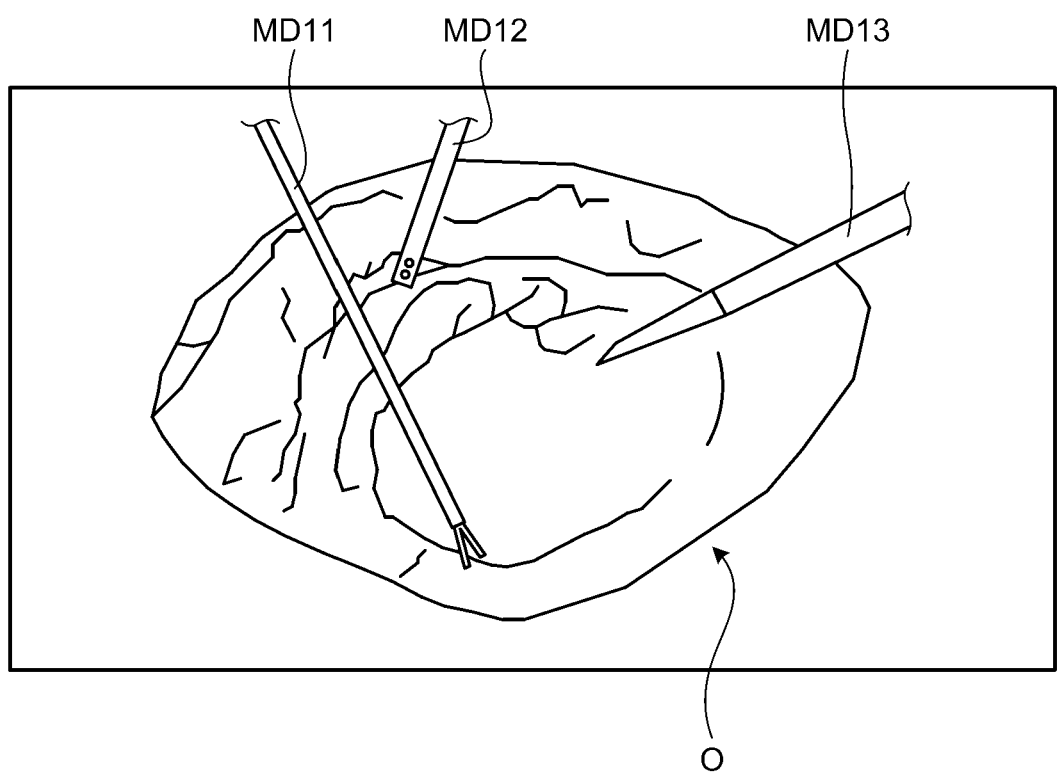
FIG. 13A is a diagram for describing information recognized by a recognition unit according to the embodiment of the present disclosure.

A first operative field image IM21 illustrated in FIG. 13A is an image in which an organ O is treated by using a medical tool MD11, a medical tool MD12, and a medical tool MD13. For example, the first operative field image IM21 is image data taken by a stereo sensor. For example, the recognition unit 214 recognizes the types of the medical tool MD11, the medical tool MD12, and the medical tool MD13 included in the first operative field image IM11. Examples of the types of medical tools recognized by the recognition unit 214 include, but not limited to, forceps, a scalpel, a retractor, and an endoscope.

Figure 13B:
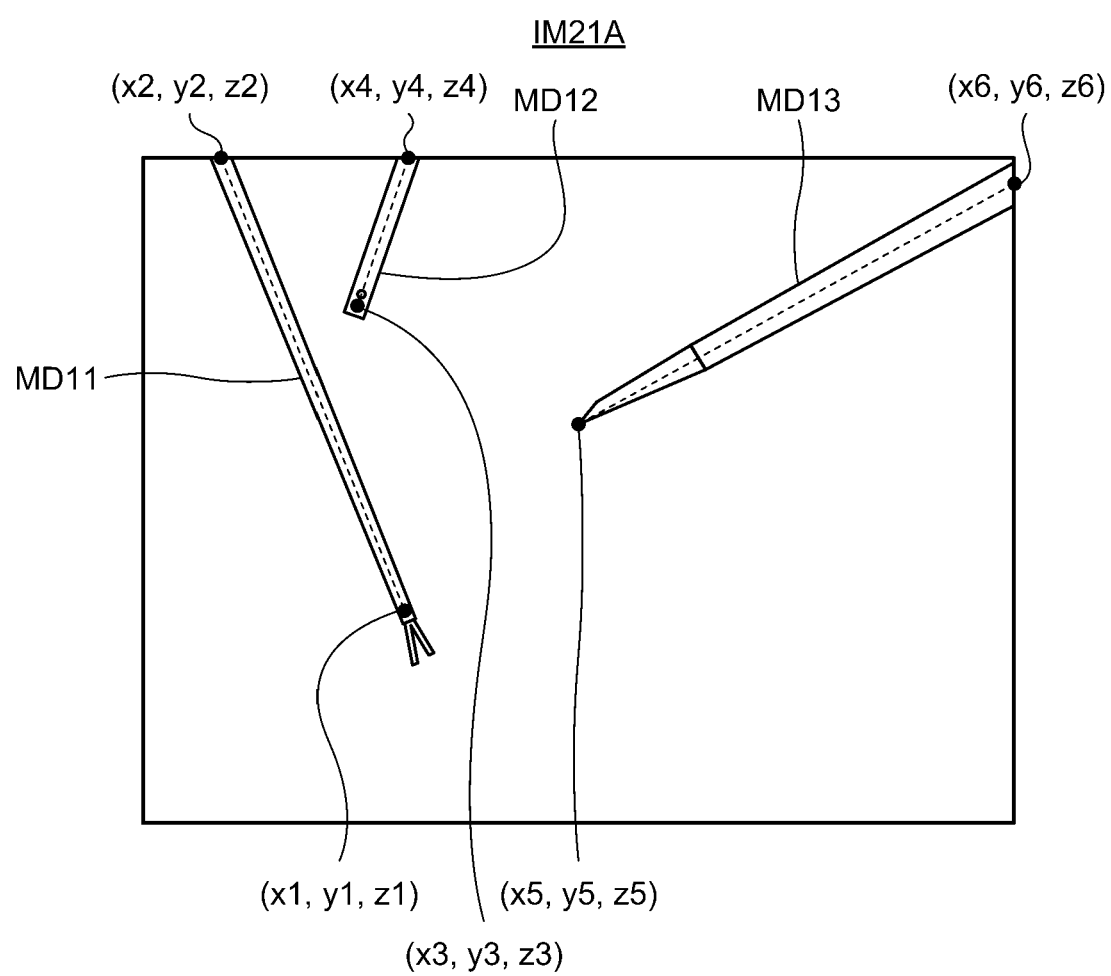
FIG. 13B is a diagram for describing information recognized by the recognition unit according to the embodiment of the present disclosure.

In a first operative field image IM21A illustrated in FIG. 13B, coordinates of the medical tools are recognized. As illustrated in FIG. 13B, the recognition unit 214 recognizes the coordinates of the medical tool MD11, the medical tool MD12, and the medical tool MD13 in a three-dimensional rectangular coordinate system in the abdominal cavity. For example, the recognition unit 214 recognizes coordinates $(x1,y1,z1)$ of one end portion and coordinates $(x2,y2,z2)$ of the other end portion of the medical tool MD11. For example, the recognition unit 214 recognizes coordinates $(x3,y3,z3)$ of one end portion and coordinates $(x4,y4,z4)$ of the other end portion of the medical tool MD12. For example, the recognition unit 214 recognizes coordinates $(x5,y5,z5)$ of one end portion and coordinates $(x6,y6,z6)$ of the other end portion of the medical tool MD13.

Figure 13C:
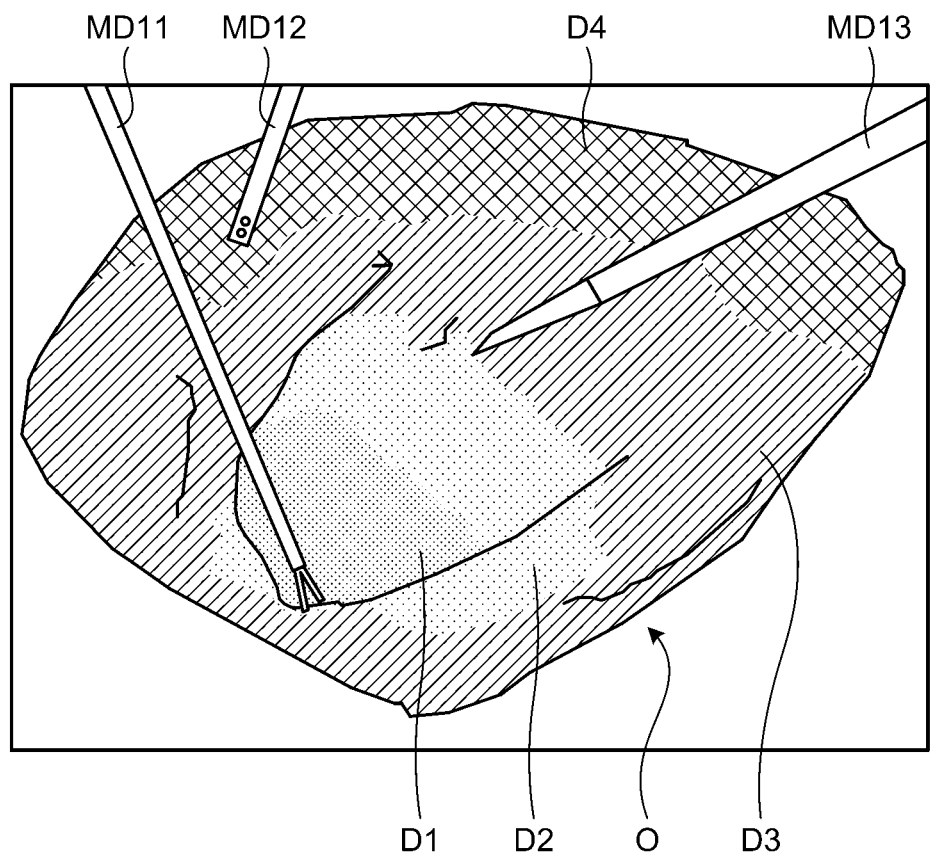
FIG. 13C is a diagram for describing information recognized by the recognition unit according to the embodiment of the present disclosure.

In a first operative field image IM21B illustrated in FIG. 13C, the depth of the organ is recognized. For example, the first operative field image IM21B is image data measured by a depth sensor. As illustrated in FIG. 13C, the recognition unit 214 recognizes the shape of the organ O. The recognition unit 214 recognizes the depth at each location in the organ O. Specifically, the recognition unit 214 recognizes a depth D1, a depth D2, a depth D3, and a depth D4. In the example illustrated in FIG. 13C, the depths become smaller in the order of the depth D1, the depth D2, the depth D3, and the depth D4. The recognition unit 214 recognizes the depth of each part of the organ O to three-dimensionally recognize the shape of the organ O.

Figure 13D:
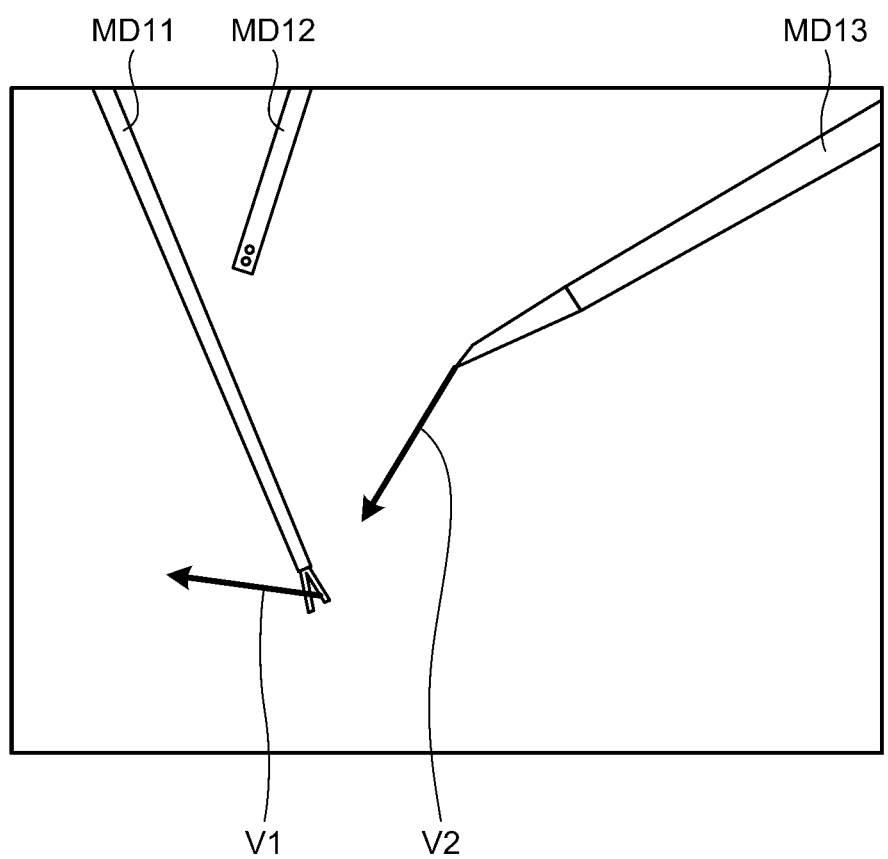
FIG. 13D is a diagram for describing information recognized by the recognition unit according to the embodiment of the present disclosure.

In a first operative field image IM21C illustrated in FIG. 13D, the motion of each medical tool is recognized. As illustrated in FIG. 13D, the recognition unit 214 recognizes the motion of the medical tool MD11, the medical tool MD12, and the medical tool MD13. For example, the recognition unit 214 recognizes the motion of the medical tool MD11 by recognizing a motion vector V1 of the medical tool MD11. For example, the recognition unit 214 recognizes the motion of the medical tool MD13 by recognizing a motion vector V2 of the medical tool MD13. In FIG. 13D, for example, the motion vector V1 and the motion vector V2 can be acquired by a motion sensor.

Figure 13E:
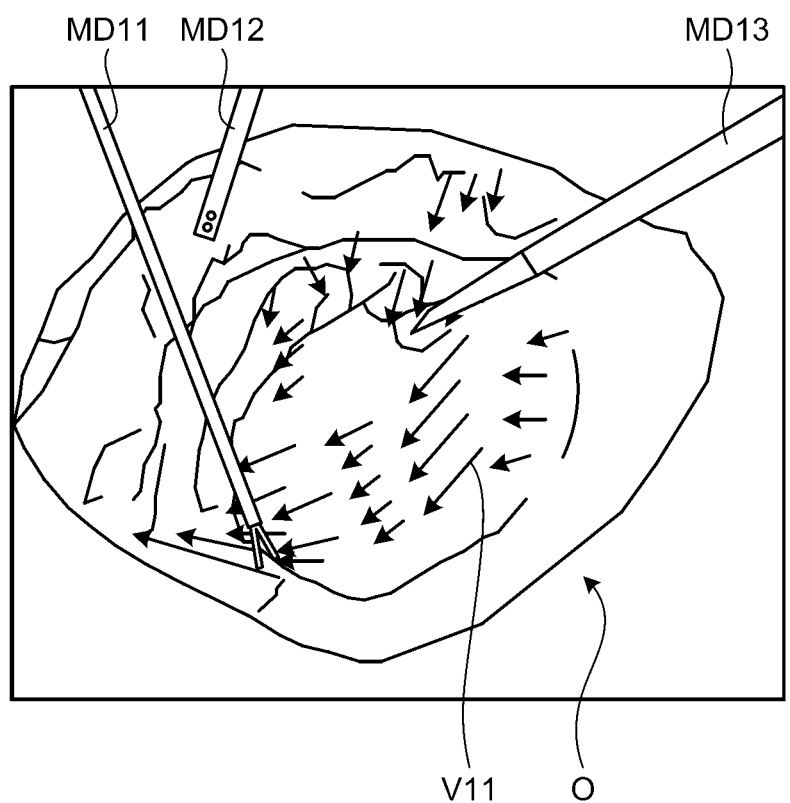
FIG. 13E is a diagram for describing information recognized by the recognition unit according to the embodiment of the present disclosure.

In a first operative field image IM21D illustrated in FIG. 13E, the motion of the organ is recognized. As illustrated in FIG. 13E, the recognition unit 214 recognizes the motion of the organ O. For example, the recognition unit 214 recognizes the motion of the organ O by recognizing a motion vector V11 at each location in the organ O. In FIG. 13E, for example, the motion vector V11 can be acquired by a motion sensor. Based on the first operative field image IM21D, the motion vector V11 may be recognized by an algorithm related to image processing such as optical flow. Based on the recognized motion vector V11, processing for canceling the motion of the imaging unit 12 may be executed.

Specifically, the recognition unit 214 recognizes at least one of an object such as a medical tool and an organ and a treatment status including the motion of a medical tool. In other words, in the present disclosure, the recognition unit 214 can recognize various kinds of situations in regions around the second operative field, which cannot be visually recognized in the second operative field visually recognized by a doctor. In other words, the recognition unit 214 can monitor the regions around the second operative field.

Referring to FIG. 6 again, the evaluation unit 215 evaluates a region of interest for the doctor as a display target region where a second operative field image is generated from a first operative field image. For example, the evaluation unit 215 determines a region of interest for the doctor based on recognition results of an operative field by the recognition unit 214.

The imaging control unit 22 controls the imaging unit 12. For example, the imaging control unit 22 controls the imaging unit 12 to image an operative field. For example, the imaging control unit 22 controls the magnification power of the imaging unit 12.

For example, the imaging control unit 22 controls the magnification power of the imaging unit 12 based on determination results received from the determination unit 24. For example, the imaging control unit 22 controls the magnification power of the imaging unit 12 based on operation information from the operation unit 30 received from the reception unit 25.

The imaging control unit 22 controls the light source unit 13. For example, the imaging control unit 22 controls the brightness of the light source unit 13 when the imaging unit 12 images the operative field.

For example, the imaging control unit 22 controls the brightness of the light source unit 13 based on determination results received from the determination unit 24. For example, the imaging control unit 22 controls the brightness of the light source unit 13 based on the positional relation of the imaging unit 12 with respect to the region of interest. For example, the imaging control unit 22 controls the brightness of the light source unit 13 based on operation information from the operation unit 30 received from the reception unit 25.

The arm control unit 23 comprehensively controls the robot arm device 10, and controls the driving of the arm portion 11. Specifically, the arm control unit 23 controls the driving of the arm portion 11 by controlling the driving of a joint portion 130. More specifically, the arm control unit 23 controls the amount of current supplied to a motor for an actuator in the joint portion 130 to control the number of rotations of the motor, and controls the rotation angle and generation torque in the joint portion 130.

For example, the arm control unit 23 controls the position and posture of the arm portion 11 based on the results of determination on the recognition results of the recognition unit 214 received from the determination unit 24. The arm control unit 23 controls the position and posture of the arm portion 11 based on a learned model. For example, the arm control unit 23 controls the position and posture of the arm portion based on operation information from the operation unit 30 received from the reception unit 25. For example, the arm control unit 23 controls the clipping position of the second operative field image based on determination results received from the determination unit 24. For example, the arm control unit 23 controls the size of the second operative field image based on the determination results received from the determination unit 24.

For example, the arm control unit 23 controls the position and posture of the arm portion 11 so as to improve the image quality of the region of interest in the first operative field image determined by the evaluation unit 215. For example, the arm control unit 23 controls the position and posture of the arm portion 11 so as to avoid specular reflection from the region of interest. In this manner, the arm control unit 23 changes the relative positional relation of the imaging unit 12 and the light source unit 13 with respect to the region of interest. Specifically, the arm control unit 23 controls the position and posture of the imaging unit 12 so as to suppress distortion in the circumference of the region of interest.

In this case, for example, the arm control unit 23 may control the position and posture of the arm portion 11 by driving the joint portion 111 in the arm portion 11 so as to avoid medical tools that block the visual field of the user. For example, the arm control unit 23 may control the position and posture of the arm portion 11 by controlling the position and posture of the arm portion 11 such that the region of interest is shifted from the center of the first operative field image.

The arm control unit 23 may control the position and posture of the arm portion 11 such that the region of interest is located at substantially the center of the first operative field image. In this manner, the doctor can easily visually recognize the region of interest.

The determination unit 24 outputs various kinds of determination results based on a model learned in advance. The learned model may be stored in the determination unit 24 or in the storage unit 60. For example, the determination unit 24 outputs various kinds of determination results based on a learned model generated by learning a treatment status including information on treatment by an operator and endoscope operation data on camera operation by a scopist. For example, the determination unit 24 determines the region of interest for the doctor in the operative field based on the learned model.

According to one implementation, for example, where labeling is not utilized, the following may occur. Given that the center area of the image captured by the endoscope in the learning phase corresponds to the region of interest for the surgeon, movement of the endoscope may be generated based on the trained model so that it replicates the learned movement. The trained model may output the estimated position of the endoscope (spatial position and attitude) at a future time, and the position and distance to the subject of the endoscope may be moved to a future predicted or calculated position based on the training artificial intelligence model. Alternatively, where there is no labeling performed, the pixels on which the surgeon or other observer focus or has an interest may be utilized as the training data for the artificial intelligence model being used.

In the present disclosure, learning data used to generate the learned model is not limited to the treatment status and the endoscope operation data. For example, the learned model may be generated based on other kinds of data on a surgery. For example, the data on a surgery may include information on medical tools used for a surgery. For example, the information on medical tools may include image data generated by medical tools and information on the medical tools. In the present disclosure, the determination accuracy can be improved by using a learned model generated based on image data taken by various kinds of medical tools and information on operation of various kinds of medical tools.

Specifically, for example, the learning data may include measurement results of at least one of a stereo sensor, a depth sensor, and a motion sensor. More specifically, the learning data may include information on operative field environments including at least one of the position, posture, type, and motion of a medical tool and an organ obtained from at least one of a stereo sensor, a depth sensor, and a motion sensor. By using a learned model based on measurement results of at least one of a stereo sensor, a depth sensor, and a motion sensor, the measurement results of the stereo sensor, the depth sensor, and the motion sensor measured during a surgery can be used to determine the region of interest for the doctor.

Data on a surgery used to generate a learned model may include information on the arm portion 11. For example, the information on the arm portion 11 may include information on the state of the joint portion 111 in the arm portion 11. For example, the information on the state of the joint portion 111 in the arm portion 11 may include various kinds of information on the position, posture, and motion of the joint portion in the arm portion 11. In the present disclosure, the determination accuracy can be improved by using a learned model generated based on various kinds of information on the arm portion 11.

The information on the arm portion 11 may include information on a medical tool gripped by the arm portion 11. For example, the information on a medical tool may include at least one of the type of the medical tool and position information and posture information on the medical tool. In the present disclosure, the determination accuracy can be improved by using a learned model generated based on various kinds of information on a medical tool gripped by the arm portion 11.

For example, the determination unit 24 determines, based on a learned model generated in advance, an eye vector (corresponding to the line of sight) including a region of interest to be visually recognized by a doctor, the intended position and posture of the imaging unit 12, and distance information from the distal end of the endoscope to a target. The arm control unit 23 calculates, based on the determination result of the determination unit 24, the position and posture of the arm portion 11 and the clipping position of the second operative field image, and is driven based on the calculation results.

During the training or learning phase, the surgeon will move the position of the endoscope and the position of the desired image or clipping of the image to the correction position. The center area of the image where the quality has a label of "Good" may be considered the region of interest, or the surgeon may add onto the image, a point of interest and/or a subject to observe. A vector from the endoscope to the area of interest can be calculated by using, for example, a distal end position and attitude of the endoscope (from the arm configuration), a clipped position, a position of the area of interest, and depth information of the area of interest.

In the present disclosure, the control unit 20 may have a function for generating a learned model. In this case, the control unit 20 holds a model for learning, and stores a generated learned model in the storage unit 60.

The learned model used in the present disclosure is generated by performing learning of a learned model in which processing corresponding to classification and sorting results of input information is performed based on features having various kinds of input information. The learned model may be implemented by a multilayer neural network having a plurality of nodes including an input layer, an intermediate layer (hidden layer), and an output layer. For example, the determination unit 24 performs learning with a deep neural network (DNN) having a plurality of hidden layers as a learned model. An example in which the determination unit 24 executes DNN is described below, but the present disclosure is not limited thereto.

Various kinds of input information are input to a learned model through an input layer. When various kinds of input information are input to the learned model through the input layer, processing for extracting features of the input information is performed at a plurality of intermediate layers. More specifically, the model has intermediate layers connected in series, and the intermediate layers sequentially perform various kinds of processing on the input information. The model outputs, through the output layer, various kinds of processing results such as classification results based on information output from the intermediate layers as output information corresponding to the input information. Such a model learns features having input information by correcting a connection coefficient between nodes such that desired output information is output when predetermined input information is input. Such learning can be implemented by a method such as backpropagation.

The training data used to train the model such as a neural network or any other artificial intelligence model may include: (1) a sample ID which may be provided or corresponds to each data measured at each measurement time; (2) a time; (3) an indication of the image quality/condition of the image captured by a camera (an endoscope or a microscope attached to an arm, for example), (4) camera information, and (5) surgical tool information of one tool, two tools or three or more tools. While 5 type of training data have been listed above, any number of types of training data can be used, including for example on three of the five types of training data. The plurality of type of training data may be considered a set of training information.

The indication of the image quality/condition/orientation can be of the form: Good, Neutral, or Poor. Alternatively, the image quality/condition/orientation can be a number between 0 and 1. For example, "Good" could be 0.6 to 1, "Neutral" could be 0.4 to 0.6, and "Poor" could be less than 0.4. The training data will preferably have this quality/condition indicated by a human (a doctor, for example) who subjectively indicates his/her preferences and/or observation of the scene with emphasis on what is visible/obstructed.

The camera information could indicate a position of the camera by using the coordinates X, Y, and Z. Further, the training data will include, if desired, Quaternion information such as, for example, Q0, Q1, Q2, and Q3.

In addition to the item, organ, or tissue being viewed, there may be one or more tools that could obstruct the image. For example, for each training data sample, there could be a right tool and a left tool. Each of the tools may have an indication of a type of the tool, position X, Y, and Z of the tool, such as the distal end or tip of the tool, and Quaternion Q0, Q1, Q2, and Q3.

In addition to and/or alternative to the above information, a depth map or disparity map may be utilized as part of the training, for each training sample. A depth map or disparity map may have the screen or image divided up into a grid. For example, a 10 across by an 8 vertical grid, a 190 by 100 grid, or any desired size grid may be utilized which indicates a depth from a specific point or plane to an object at the corresponding grid position in the image.

In addition or alternative to the information used for training explained above, the endoscopic image itself may be used for training.

Geometric data, also referred to as input information, used as training data described above may include position information, and Quaternion information of the camera and tools, is provided to the training model from a processor used for image recognition that receives the captured endoscopic image and calculates the geometric data. Therefore, the captured image may be not directly provided to the training model from the endoscope system. The motion data of the camera may alternatively be provided by a camera that captures the surgical scene and calculates the spatial positions of markers attached on the camera and/or tools, such as surgical tools.

A function for labeling is not essential but may be implemented for calculating the quality of the field of view of the endoscope in a time series manner. For example, a distance between the center of the captured image and the position of the right instrument (or the left instrument) in the image could be one of the indicators of the quality of the field of view.

The control unit 20 may generate a learned model for various kinds of surgeries or may hold a predetermined model. For example, the control unit 20 generates a learned model from learning data including a treatment status including information on treatment by an operator and endoscope operation data on camera operation by a scopist. For example, the control unit 20 generates a learned model by using a medical tool measured by a tracking device the position and posture of the endoscope as learning data. For example, the control unit 20 generates a learned model by using an endoscope image including the depth and motion of each target and the type of the medical tool taken by a stereo endoscope as learning data.

The control unit 20 may generate a learned model by using data on various kinds of surgical robots as learning data. For example, the control unit 20 generates a learned model by using various kinds of operation information on surgical robots by doctors and scopists as learning data. For example, the control unit 20 may generate a learned model by using treatment using the support arm device 400 illustrated in FIG. 3 as learning data.

By using the above information to train an artificial intelligence model or system such as a neural network, the result will be an improved ability to predict what view the surgeon, endoscope operator, or viewer of the image will desire to see. Thus, the image presented to the viewer can automatically without user intervention and autonomously change to a better or more preferred view using the trained artificial intelligence model or neural network. According to one embodiment, there is no need for a user or scopist to trigger the generation of a second medical image or clipped medical image, but the system will automatically determine, without user intervention, that a second medical image is to be displayed. Additionally or alternatively, the second medical image can be automatically determined without user intervention.

The present disclosure may utilize conventional artificial intelligence techniques including neural networks which have been improved and/or trained to use one or multiple instruments with varying degrees of obstruction in order to present to the viewer an improved image by having the endoscope or other medical camera automatically and autonomously change its position. The training samples may be considered as "ground truth" samples. Newly captured images are compared to the trained model and/or actual or ground truth examples/samples that are characterized as appropriate, accurate, and/or desirable, so that the system can automatically shift or change the image being displayed to be a better image which includes more pertinent information.

The determination unit 24 executes deep learning using the learned model. For example, the determination unit 24 receives various kinds of recognition results by the recognition unit 214 described above with reference to FIG. 13A to FIG. 13E. For example, the determination unit 24 determines the clipping position of an operative field in a wide-angle image desired by a doctor and the position and posture of the arm portion 11 based on the recognition results.

Figure 14A:
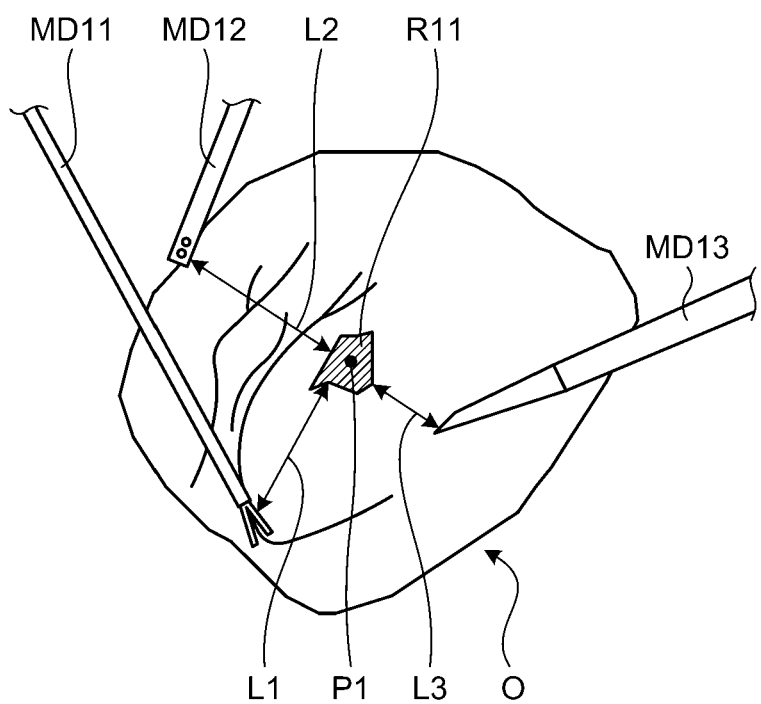
FIG. 14A is a diagram for describing a determination result of a learning unit according to the embodiment of the present disclosure.
Figure 14C:
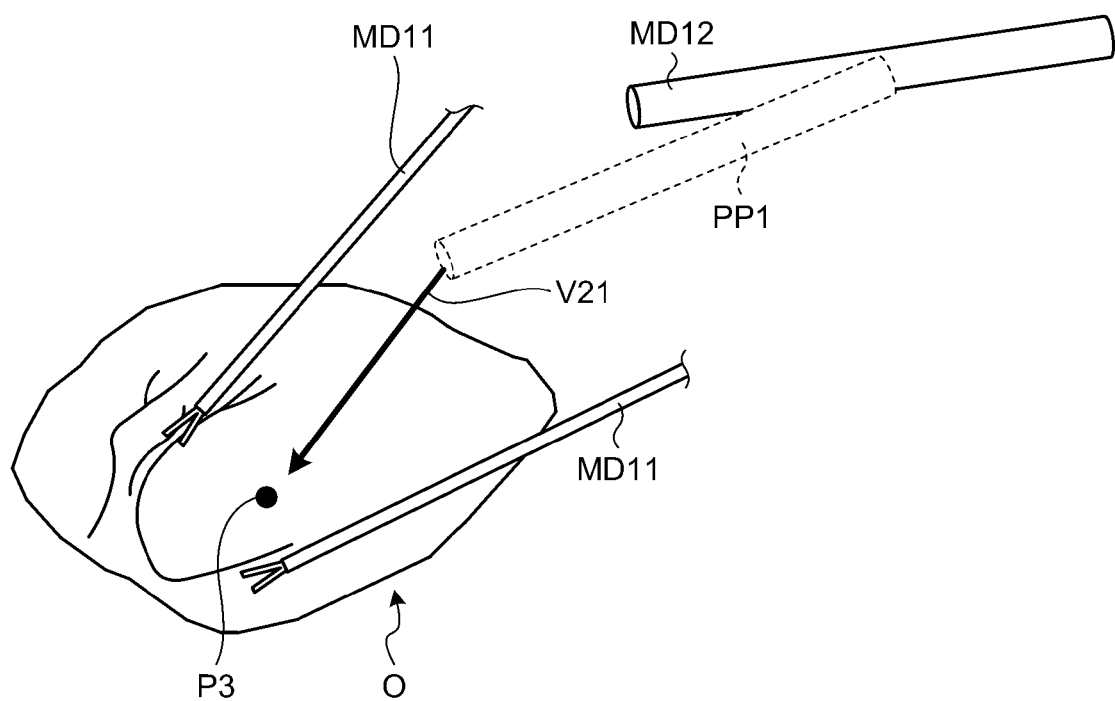
FIG. 14C is a diagram for describing a determination result of the learning unit according to the embodiment of the present disclosure.

Referring to FIG. 14A, FIG. 14B, and FIG. 14C, determination results by the determination unit 24 are described. FIG. 14A to FIG. 14C are diagrams for describing the determination results by the determination unit 24.

As illustrated in FIG. 14A, for example, the determination unit 24 determines a point of regard P1 to which the medical tool MD12 (endoscope) should be directed based on various kinds of recognition results by the recognition unit 214. For example, the determination unit 24 determines a distance L1 between the medical tool MD11 and a target region R11 in the organ O. For example, the determination unit 24 determines a distance L2 between the medical tool MD12 and the target region R11. For example, the determination unit 24 determines a distance L3 between the medical tool MD13 and the target region R11.

As illustrated in FIG. 14B, for example, the determination unit 24 determines an eye vector V21 connecting a distal end of the medical tool MD12 (endoscope) and a point of regard P2 to which the endoscope should be directed based on various kinds of recognition results by the recognition unit 214. Alternatively, the determination unit 24 determines a trajectory plan for directing the medical tool MD12 (endoscope) to the point of regard P2.

As illustrated in FIG. 14C, for example, the determination unit 24 determines an eye vector V21 connecting the distal end of the medical tool MD12 (endoscope) and a point of regard P3 to which the endoscope should be directed based on various kinds of recognition results by the recognition unit 214. For example, the determination unit 24 determines the position and posture PP1 of the medical tool MD12 (endoscope) such that an eye vector connecting the distal end of the medical tool MD12 (endoscope) and the point of regard P2 to which the endoscope should be directed becomes the eye vector V21.

The determination unit 24 outputs various kinds of determination results illustrated in FIG. 14A to FIG. 14C to the imaging control unit 22 and the arm control unit 23. For example, the imaging control unit 22 controls the magnification power of the imaging unit 12 based on the determination results received from the determination unit 24. For example, the arm control unit 23 controls the position and posture of the arm portion 11 based on the determination results received from the determination unit 24.

Specifically, the determination unit 24 determines the position and posture of the arm portion 11 based on at least one of objects (for example, medical tools and organ) included in the first operative field image and the treatment status. The determination unit 24 determines the position and posture of the arm portion 11 based on at least one the type and shape of the organ and the position, posture, and shape of the medical tool.

The determination unit 24 updates the weighting of the learned model based on whether the result of controlling the position and posture of the arm portion based on the determination result is control desired by the doctor. Specifically, for example, when the result of controlling the position and posture of the arm portion based on the determination result is an erroneous determination result, the determination unit 24 updates the weighting of the learned model. The determination unit 24 stores the learned model with the updated weighting in the storage unit 60. For example, the determination unit 24 stores the learned model in the storage unit 60 each time the weighting of the learned model is updated.

The reception unit 25 receives various kinds of operation information input to the operation unit 30. The operation information may be input by voice and may be input by a physical mechanism. Examples of the operation information from the operation unit 30 include instruction information for changing the magnification power of the imaging unit 12 and the position and posture of the arm portion 11. For example, the reception unit 25 outputs the instruction information to the imaging control unit 22 and the arm control unit 23. For example, the imaging control unit 22 controls the magnification power of the imaging unit 12 based on the instruction information received from the reception unit 25. For example, the arm control unit 23 controls the position and posture of the arm portion 11 based on the instruction information received from the reception unit.

The display control unit 26 displays various kinds of video on the first operative field image display unit 40 and the second operative field image display unit 50. For example, the display control unit 26 displays a first operative field image acquired by the acquisition unit 211 from the imaging unit 12 on the first operative field image display unit 40. For example, the display control unit 26 displays a second operative field image generated by the generation unit 212 on the second operative field image display unit 50.

The operation unit 30 receives various kinds of operation information from a user. For example, the operation unit 30 is configured by a microphone for detecting voice, a visual line sensor for detecting the visual line, and a switch and a touch panel for receiving physical operation. The operation unit 30 may be configured by other physical mechanisms.

The first operative field image display unit 40 and the second operative field image display unit 50 display various kinds of images. For example, the first operative field image display unit 40 displays a first operative field image taken by the imaging unit 12. For example, the second operative field image display unit 50 displays a second operative field image generated by the generation unit 212. Examples of the first operative field image display unit 40 and the second operative field image display unit 50 include a liquid crystal display (LCD) and an organic electro-luminescence (EL) display.

For example, the medical observation system 1 in the present disclosure may include a third operative field image display unit (not shown) for displaying the above-mentioned third operative field image. For example, the third operative field image display unit is a display unit visually recognized by an assistant for an operator. In the present disclosure, by providing the third operative field image display unit for an assistant, the operability can be improved.

The storage unit 60 stores various kinds of information therein. For example, the storage unit 60 stores therein a learned model generated by the determination unit 24. For example, the storage unit 60 is implemented by a semiconductor memory element such as a random access memory (RAM) and a flash memory or a storage device such as a hard disk and an optical disc.

As described above, in the present disclosure, a fine image obtained by performing super-resolution processing on a second operative field image corresponding to a conventional endoscope can be provided to a doctor. By executing recognition processing on the first operative field image taken by the imaging unit 12, a situation that occurs in a blind spot that cannot be visually recognized by a doctor can be detected.

As described above, the position and posture of the arm portion 11 can be autonomously controlled based on the determination result of the first operative field image by the determination unit 24 in addition to the operation information to the operation unit 30 received from a user. The operation by the determination unit 24 and the operation by the operation unit 30 may be switched or may be used simultaneously. For example, when the operation unit 30 is configured by a visual line detection sensor, the user may detect a point of regard on the second operative field image display unit 50, and determine the enlargement amount of the point of regard by the determination unit 24 in combination.

In the case where the visual line of the endoscope is controlled by six degrees of freedom in the body's internal environments of a patient, the control is difficult in the conventional case as long as an input device having multiple degrees of freedom such as a master-slave device is used. In the present disclosure, the arm portion 11 is autonomously controlled based on wide-angle video of an operative field, thereby controlling the visual line in the body's internal environments of a patient. Consequently, the visual line can be freely changed in the body's internal environments without using any user's operation and any special input device.

Figure 15:
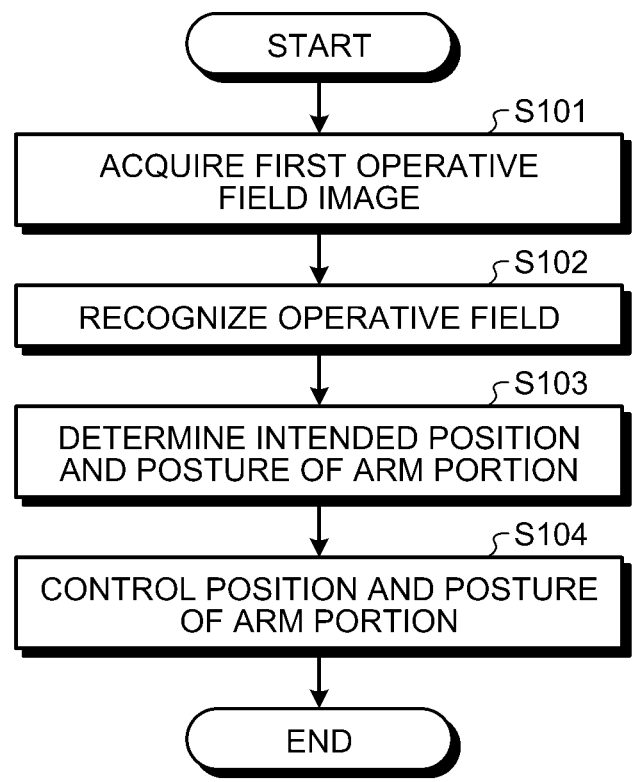
FIG. 15 is a flowchart illustrating an example of the flow of processing for controlling the position and posture of an arm portion by a control unit according to the embodiment of the present invention.

Referring to FIG. 15, processing in which the control unit 20 according to the embodiment of the present invention controls the position and posture of the arm portion is described. FIG. 15 is a flowchart illustrating an example of the flow of processing in which the control unit 20 according to the embodiment of the present invention controls the position and posture of the arm portion.

First, the control unit 20 acquires a first operative field image (Step S101). Specifically, the acquisition unit 211 acquires a first operative field image from the imaging unit 12. The flow proceeds to Step S102.

Next, the control unit 20 recognizes an operative field based on the first operative field image (Step S102). Specifically, the recognition unit 214 recognizes the type of a medical tool included in the first operative field image and the states of the medical tool and an organ. The flow proceeds to Step S103.

Next, the control unit 20 determines the intended position and posture of the arm portion 11 (Step S103). Specifically, the determination unit 24 determines the intended position and posture (ideal position and posture in environments of recognized operative field) of the arm portion 11 based on the recognition results by the recognition unit 214 at Step S102. The flow proceeds to Step S104.

Next, the control unit 20 controls the position and posture of the arm portion 11 (Step S104). Specifically, the arm control unit 23 controls the position and posture of the arm portion 11 based on the determination results by the determination unit 24 at Step S103. The processing in FIG. 15 is finished.

Figure 16:
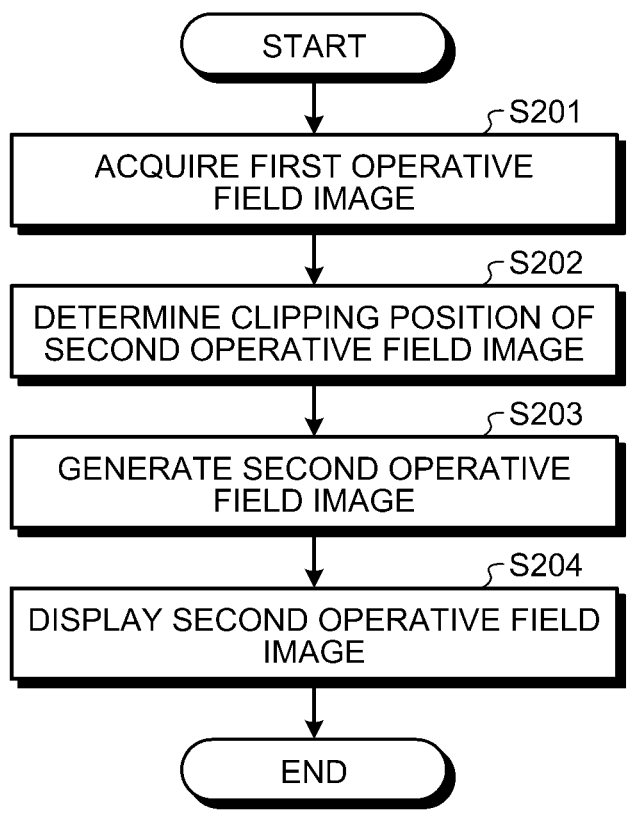
FIG. 16 is a flowchart for describing an example of the flow of processing for generating a second operative field image for a doctor from a first operative field image by the control unit according to the embodiment of the present invention.

Referring to FIG. 16, processing in which the control unit 20 according to the embodiment of the present invention generates a second operative field image for a doctor from a first operative field image is described. FIG. 16 is a flowchart for describing an example of the flow of processing in which the control unit 20 according to the embodiment of the present invention generates a second operative field image for a doctor from a first operative field image.

In the present disclosure, the processing for controlling the position and posture of the arm portion 11 illustrated in FIG. 15 and the processing for generating a second operative field image from a first operative field image illustrated in FIG. 16 are executed in parallel.

Figure 22A:
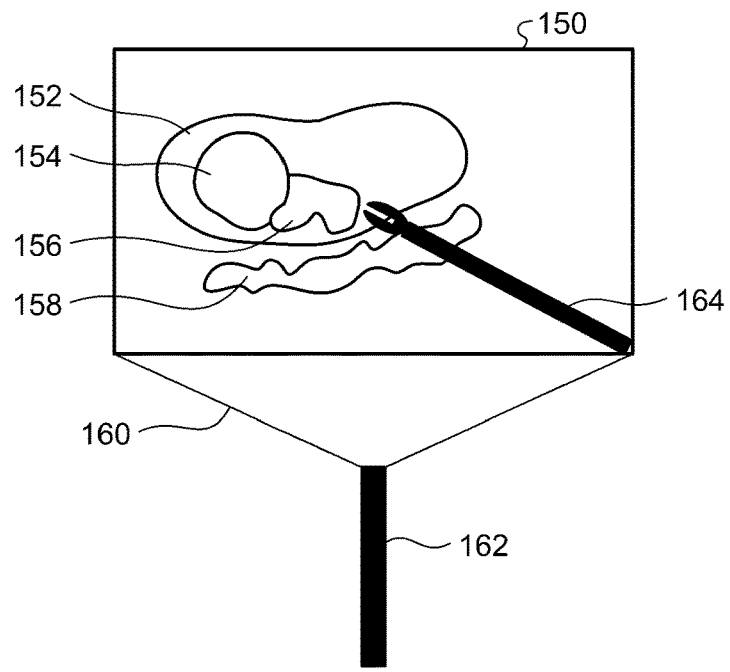
FIG. 22A illustrates a process corresponding to the flowchart of FIG. 16.

First, the control unit 20 acquires a first operative field image (Step S201). Specifically, the acquisition unit 211 acquires a first operative field image from the imaging unit 12. The first operative field, also referred to as a first medical image, is illustrated as image 150 illustrated in FIG. 22A. In FIG. 22A, the image 150 includes a liver 152, a gallbladder 154, a tumor 156, and a pancreas 158. An endoscope, camera, or microscope, also referred to as a medical imaging device 162 captures an image, usually but not necessarily, inside of a body such as the body of a human or an animal. The first medical image 150 is preferably broad and may be, if desired, captured by the medical imaging device 162 through a wide angle lens. An example angle 160 of capture of the medical imaging device 162 may be, for example, 140 degrees, greater than 100 degrees, greater than 120 degrees, greater than or equal to 140 degrees, or greater than 160 degrees. Also illustrated in the image 150 is a scissors 164. The organs and surgical tools may be defined by, for example, RGB (Red, Green Blue) and depth, also referred to RGBD) from a position, such as depth or distance from the medical imaging device 162 (or distal end of the medical imaging device 162) or if desired a point or virtual point, to be described below. When a state of the first medical image is analyzed to determine a second medical image, image information of the first medical image including depth information is analyzed.

However, a learning phase should be performed in order to train the system what the various elements in an image are. The labels of position and size of the area of interest in the first operative field image (or first medical image), and the types of the organ and the surgical tool are provided to the first operative filed image such as captured RGB+Depth image which is a wide-angle image, a 140 degree angle of viewing, for example. The captured wide-angle image and the position and the size of the area of interest relative to positions of the organ and the tool are learned by the training model. The flow proceeds to Step S202.

Figure 22B:
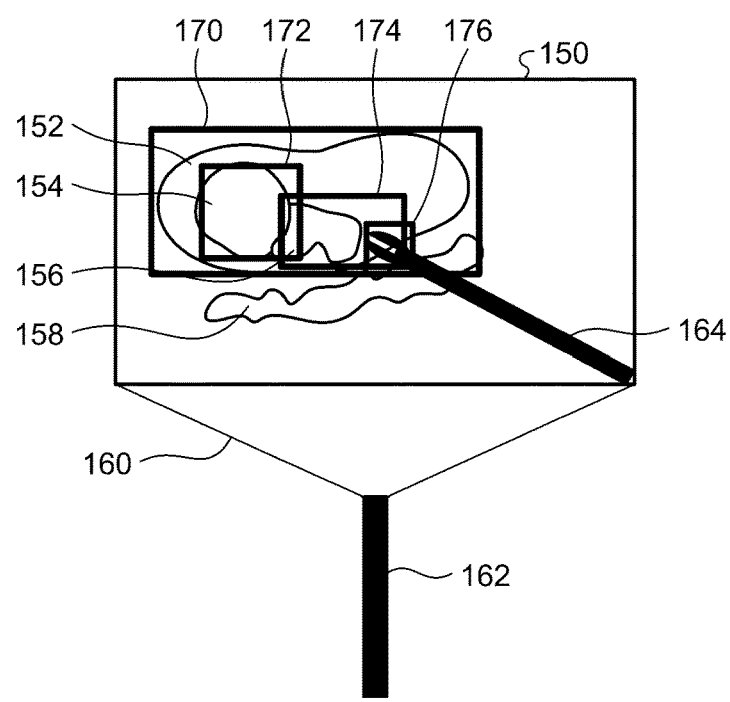
FIG. 22B illustrates a process corresponding to the flowchart of FIG. 16.

Next, the control unit 20 determines a clipping position of a second operative field image (Step S202). This may be considered an inference phase. Specifically, the recognition unit 214 determines the clipping position based on a medical tool such as the scissors 164 and one or more organs and/or tumor 156 included in the first operative field image or first medical image 150. FIG. 22B illustrates the first medical image 150 with rectangular boxes around four of the elements. A rectangular box around an element generally indicates that the object with the box is recognized by an image processing function such as image recognition performed on the captured image 150. In FIG. 22B, there is illustrated a box 170 around the liver 152, a box 172 around the gallbladder 153, and a box 176 around the scissors 176.

There is also a rectangular box 174 having therein the tumor 156 and the end of the scissors 164. This box 174 is an area of interest, and not necessarily just a single recognized object, and is described more below. The image within the box 174 will become the second medical image. The positional relationship between the tool and the organ, a treatment task (e.g. ablation, resection, or extirpation) estimated based on the type of the tool, and the position of the area of interest and the position of the endoscope relative to the treatment position, are learned by the training model. The position and the size of the area of interest designated by the box 174 is output based on the captured RGB+D image (first operative field image) and the positions of the recognized organ and tool. Image information of the first medical image include the above-described features including the organs and/or tools and/or tumors, and anything else described herein.

Figure 22C:
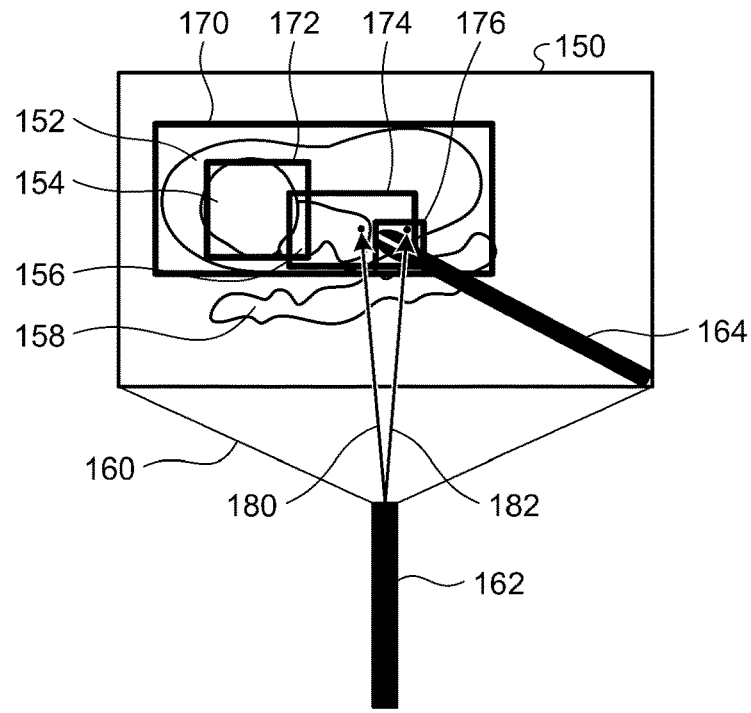
FIG. 22C illustrates a process corresponding to the flowchart of FIG. 16.
Figure 22D:
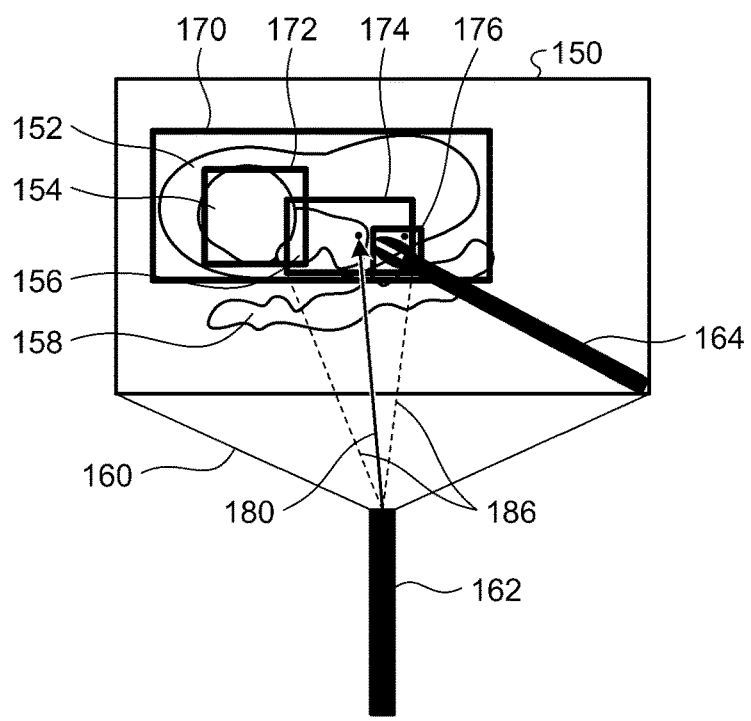
FIG. 22D illustrates a process corresponding to the flowchart of FIG. 16.

FIG. 22C is similar to FIG. 22B but includes a vector 180 which may extend, for example, from a distal tip of the medical imaging device 162 to a center point of the box or area of interest 174. This vector 180 is a vector of the line of site of the endoscope and can be calculated by using the depth from the distal end of the medical imaging device 162 to the center point of the area of interest 174, and the output position of the area of interest. The vector 180 of the line of site connecting the distal end of the medical imaging device 162 and the area of interest 174 is calculated based on the pixel position of the center of the area of interest 174 and the depth or distance to this center. There is also illustrated in FIG. 22C a vector 182 from the end of the medical imaging device 182 to the distal end of the scissors 164. This vector may be utilized to determine the depth form the medical imaging device 182 to the distal end of the scissors. FIG. 22D illustrate a narrower field of view which is between lines 186. The clipping area (position and size) of the first operative field image 150 is determined or calculated based on the output position and size of the area of interest and a predetermined angle of view (that corresponds to a usual angle of view of an endoscope, such as 70 degrees, for example, and is used to clip the image as an enlarged image on a display), so that the area of interest is covered in the predetermined angle of view. Of course, other values than 70 degrees may be utilized, such as 60 degrees, or less than 60 degrees, or 80 degrees or more than 80 degrees may be utilized for the area of interest which is the clipping area, or area of interest, also referred to as a second medical image.

The labels identifying the area of interest, organs and type of the surgical tool are given to the image captured by the endoscope. The training model may learn (a) the positional relationship between the tool and the organ, (b) a treatment task (e.g. ablation) estimated based on the type of the tool, and (c) the position of the area of interest and the position of the endoscope relative to the treatment position. The vector of the line of sight is calculated based on the position of the endoscope and the position of the area of interest. Then the position of the endoscope and the position of the image clipping can be calculated. The flow proceeds to Step S203.

In step S203, the control unit 20 generates a second operative field image or second medical image (Step S203). Specifically, the generation unit 212 clips and generates the second operative field image from the first operative field image based on the determination result of Step S202. The flow proceeds to Step S204.

Next, the control unit 20 displays the second operative field image on the second operative field image display unit 50 (Step S204). Specifically, the display control unit 26 displays the second operative field image generated at Step S203 on the second operative field image display unit 50. The processing in FIG. 16 is finished.

Figure 17:
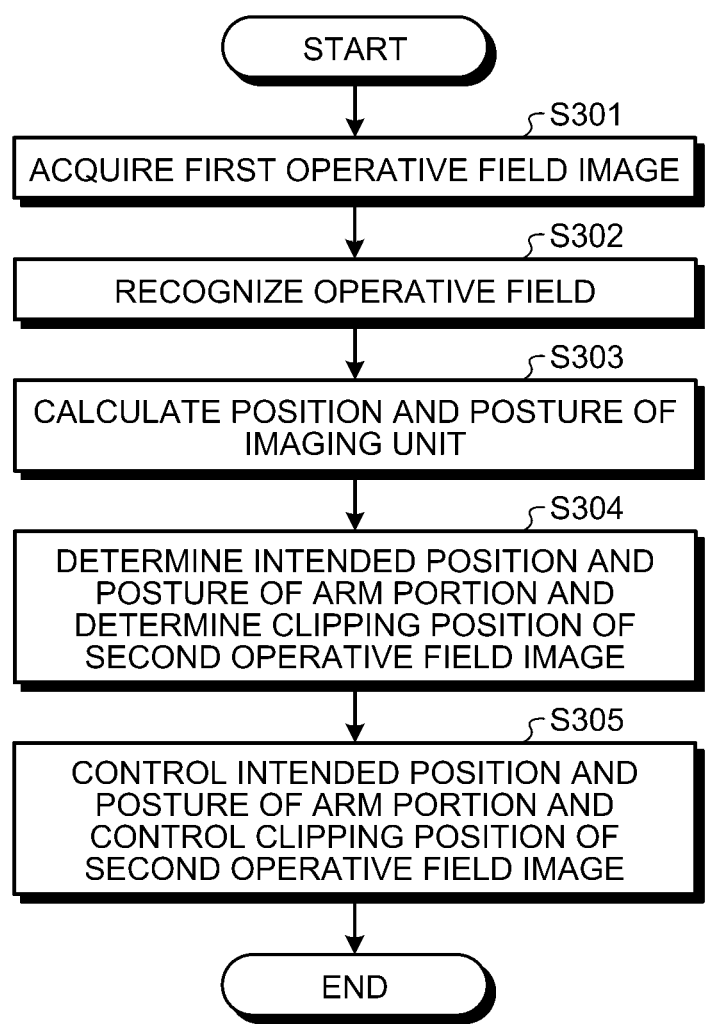
FIG. 17 is a flowchart illustrating an example of the flow of processing for controlling a clipping position of the second operative field image based on a recognition result of the first operative field image.

Referring to FIG. 17, the flow of processing in which the control unit 20 according to the embodiment of the present invention controls a clipping position of a second operative field image based on a recognition result of a first operative field image is described. FIG. 17 is a flowchart illustrating an example of the flow of processing in which the control unit 20 according to the embodiment of the present invention controls a clipping position of a second operative field image based on a recognition result of a first operative field image.

First, the control unit 20 acquires a first operative field image (Step S301). Specifically, the acquisition unit 211 acquires a first operative field image from the imaging unit 12. The flow proceeds to Step S302.

Next, the control unit 20 recognizes an operative field based on the first operative field image (Step S302). Specifically, the recognition unit 214 recognizes the type of medical tools included in the first operative field image and the states of the medical tools and an organ state. The flow proceeds to Step S303.

Next, the control unit 20 calculates the intended position and posture of the imaging unit 12 based on the recognition result of the first operative field image (Step S303). Specifically, the determination unit 24 calculates the intended position and posture (optimal position and posture) of the imaging unit 12 based on the recognition result at Step S302 and a learned model. The flow proceeds to Step S304.

Next, the control unit 20 determines the intended position and posture of the arm portion 11 and the clipping position of the second operative field image (Step S304). Specifically, the arm control unit 23 determines the intended position and posture of the arm portion 11 and the clipping position of the second operative field image based on the calculation results at Step S303. The flow proceeds to Step S305.

Next, the control unit 20 controls the intended position and posture of the arm portion 11 and the clipping position of the second operative field image (Step S305). Specifically, the arm control unit 23 controls the intended position and posture of the arm portion 11 and the clipping position of the second operative field image based on the determination results at Step S304.

Figure 22E:
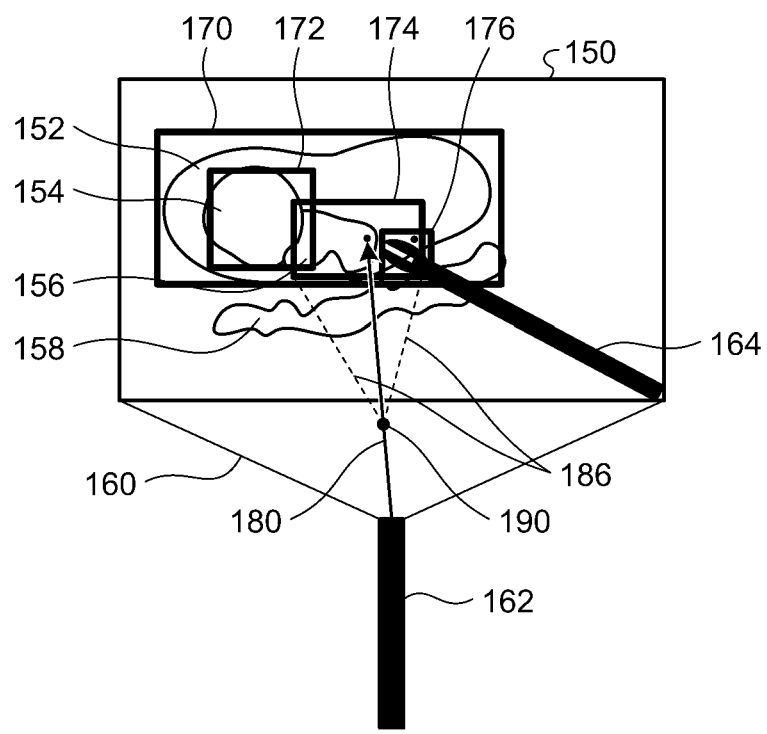
FIG. 22E illustrates an optional processing corresponding to step S305 of FIG. 17.

In the process described in steps S202 and/or S203 of FIG. 16, the clipping area is determined. As a further step, a distance between the center of the area of interest and a position (virtual view point) such as point 190 of FIG. 22E which may be away from the distal end of the medical imaging device 162 from which the area of interest can be captured is determined. The virtual view point on the calculated vector (the vector 180 of FIGS. 22C and 22D) and a posture of the medical imaging device 162 is determined based on the calculated vector 180 and the distance (depth) that satisfies the predetermined angle of view. The determined view point and the posture of the endoscope may be used to control an articulated arm holding the medical imaging device 162. As the second operative field image is electrically clipped and the mechanical control of the arm when clipping is not required. Thus, this determination and/or use of the virtual point 180 illustrated in FIG. 22E is optional. The processing in FIG. 17 is finished.

5. Control of Arm Supporting Forward-Oblique Viewing Endoscope

In the present embodiment, a technology for implementing an endoscope holder arm that maintains hand-eye coordination is mainly described. The hand-eye coordination may mean that the hand feeling and the visual feeling (sense of vision) are cooperative (hand feeling and visual feeling (sense of vision) match). One feature of such a technology resides in that "(1) forward-oblique viewing endoscope unit is modeled as a plurality of interlocking links". Another feature of such a technology resides in "(2) whole-body cooperative control of arm is extended to perform control by using relation between relative motion space and interlocking links".

Figure 18:
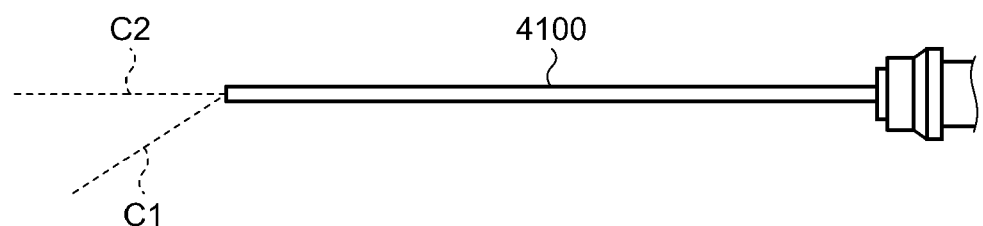
FIG. 18 is a diagram for describing an optical axis of a forward-oblique viewing endoscope.

Referring to FIG. 18, the usage and operation of a forward-oblique viewing endoscope as an example of a hard mirror are described. FIG. 18 is a diagram for describing an optical axis of the forward-oblique viewing endoscope. Referring to FIG. 18, a hard mirror axis C2 and a forward-oblique viewing endoscope optical axis C1 in a forward-oblique viewing endoscope 4100 are illustrated.

During a surgery, a scopist rotates a camera head CH to adjust a monitor screen in order to maintain the hand-eye coordination of the operator when the forward-oblique viewing endoscope is rotationally operated. When the scopist rotates the camera head CH, the arm dynamic characteristics change around the hard mirror axis C2. The display screen on the monitor rotates about the forward-oblique viewing endoscope optical axis C1.

In the present disclosure, the electronic degree of freedom of the rotational operation of the endoscope performed by the scopist is changed as described above to maintain the hand-eye coordination.

Subsequently, the above-mentioned "(1) modeling of forward-oblique viewing endoscope unit as interlocking links" is described. In the present embodiment, the characteristics of operation about the hard mirror axis C2 and operation about the forward-oblique viewing endoscope optical axis C1 described above are modeled to perform control. First, the forward-oblique viewing endoscope is modeled by an actual rotation link and a virtual rotation link. Herein, the description is mainly given by using the actual rotation link as an example of an actual link and using the virtual rotation link as an example of a virtual link. However, another actual link (such as parallel actual link) may be used instead of the actual rotation link, and another virtual link (such as parallel virtual link) may be used instead of the virtual rotation link. The axis of the actual rotation link may be the hard mirror axis C2 (=rotation axis of imager), and the axis of the virtual rotation link may be the forward-oblique viewing endoscope optical axis C1. The virtual rotation link is a link that does not exist actually, and operates in cooperation with the actual rotation link.

Figure 19:
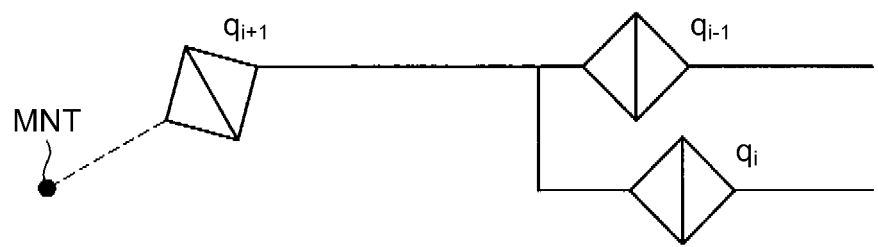
FIG. 19 is a diagram for describing model creation and control.

FIG. 19 is a diagram for describing modeling and control. Referring to FIG. 19, the rotation angle at each link is illustrated. Referring to FIG. 19, a monitor coordinate system MNT is illustrated. Specifically, control is performed such that relative motion space C expressed by the following (1) becomes 0.

[Math.1]

$$C(=\alpha_{i+1} * q_{i+1} + \alpha_i * q_i) = q_{i+1} - q_i \tag{1}$$

Subsequently, the above-mentioned "(2) whole-body cooperative control of arm is extended to perform control by using relation between relative motion space and interlocking links" is described. In the present embodiment, the whole-body cooperative control is performed in a unified manner by extension using interlocking links and relative motion space. In a joint space, an actual rotation axis and a virtual rotation axis are taken into consideration. The actual rotation axis and the virtual rotation axis are independent from the arm configuration. In motion purpose, the relative motion space in addition to Cartesian space is taken into consideration. By changing the motion purpose of Cartesian space, various operations can be performed.

Figure 20:
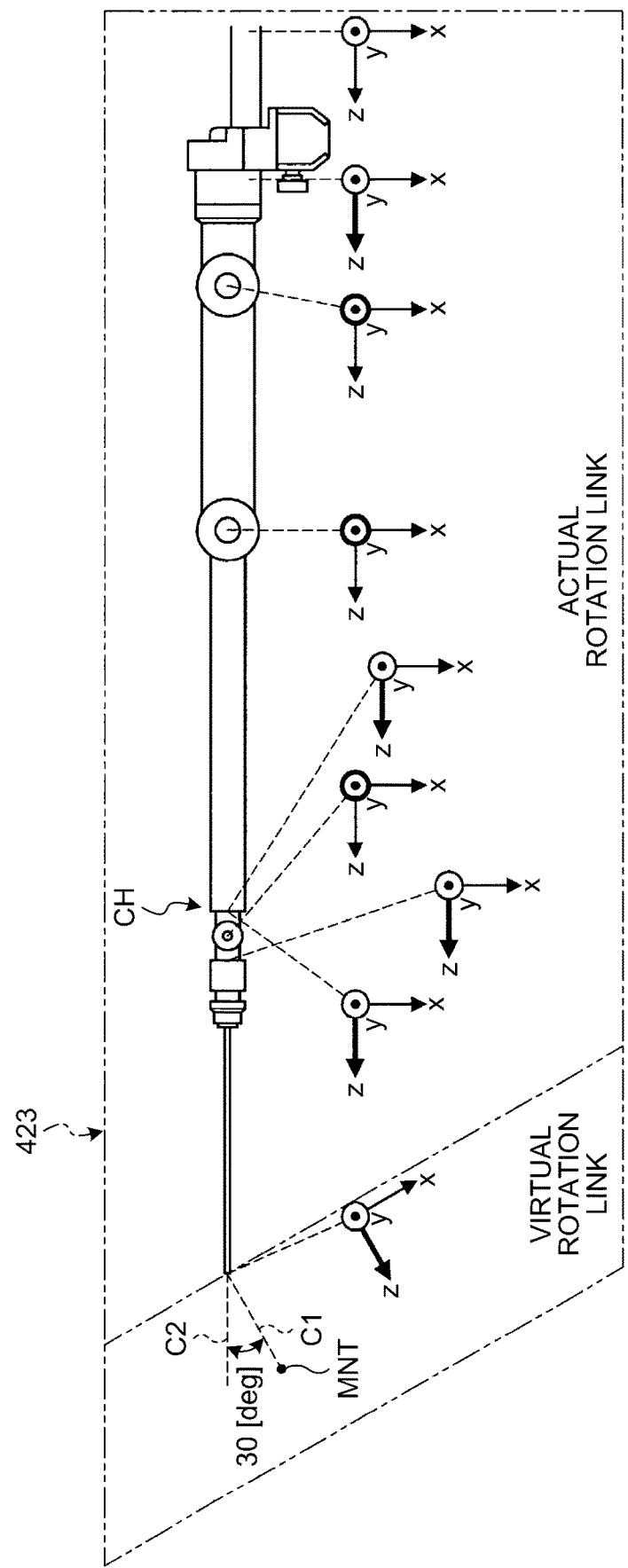
FIG. 20 is a diagram illustrating an example of each link configuration when the extension of whole-body cooperative control is applied to a 6-axis arm and a forward-oblique viewing endoscope unit.

For example, it is assumed that the extension of the whole-body cooperative control is applied to a six-axis arm and a forward-oblique viewing endoscope unit. FIG. 3 illustrates the rotation angles at the links as q1 to q8. q7 corresponds to a rotation angle about the axis of the actual rotation link (=rotation axis of imager), and q8 corresponds to a rotation angle about the axis of the virtual rotation link. FIG. 20 is a diagram illustrating an example of each link configuration when the extension of the whole-body cooperative control is applied to a six-axis arm and a forward-oblique viewing endoscope unit. In this case, the controlling expression is expressed by the following (2).

[Math. 2]

$$\begin{bmatrix} \dot{q}_1 \\ \vdots \\ \dot{q}_7 \\ \dot{q}_8 \end{bmatrix} = J^{\#} \begin{bmatrix} \dot{x} \\ \dot{c} \end{bmatrix} \quad (2)$$

In the above-mentioned (2), the temporal derivative value of q8 and the temporal derivative value of the relative motion space c correspond to the extended part of the whole-body cooperative control.

"(2) The whole-body cooperative control of arm is extended to perform control by using relation between relative motion space and interlocking links" has been describe above.

6. Setting of Virtual Link

Subsequently, the setting of a virtual link is described. Prior to describing a method for setting a virtual link in the present disclosure, a method for controlling the mechanism of an arm to set a virtual link is first described.

A calculation condition setting unit for setting conditions of a virtual link may function as a virtual link setting unit for setting a virtual rotation link as an example of the virtual link. For example, the calculation condition setting unit sets a virtual link by setting at least one of the distance and direction of the virtual link. FIG. 20 illustrates an example of "virtual rotation link" and "actual rotation link". As illustrated in FIG. 20, the actual rotation link is a link corresponding to a lens barrel axis of the scope. The virtual rotation link is a link corresponding to a forward-oblique viewing endoscope optical axis C1 of the scope.

The calculation condition setting unit forms a model of the virtual rotation link based on a coordinate system defined with reference to an actual rotation link distal end of the arm, freely selected points existing on the forward-oblique viewing endoscope optical axis C1, and a line connecting the points, and uses whole-body cooperative control. In this manner, independently from the hardware configuration of the arm, the posture can be fixed in the virtual rotation link coordinate system, and in a surgery, the motion purpose such as fixing the point of view in any point direction at the virtual rotation link distal end while maintaining position of a trocar point serving as a scope insertion position can be implemented. The actual rotation link distal end may mean a point through which the optical axis C1 passes on the arm.

The calculation condition setting unit can set a virtual rotation link based on the specifications of a connected scope and freely selected points on a space. According to the setting of the virtual rotation link based on the specifications of the scope, the conditions for setting the virtual rotation link are not required to be limited to the case where a particular scope is used, and hence the operation for motion purpose can be implemented only by dynamically updating the model through the setting of the virtual rotation link when the scope is changed.

The scope specifications may include at least one of the structural specifications of the scope and the functional specifications of the scope. In this case, the structural specifications of the scope may include at least one of the angle of squint of the scope and the dimensions of the scope. The specifications of the scope may include the position of the axis of the scope (information on axis of scope may be used for setting of actual rotation link). The functional specifications of the scope may include a focus distance of the scope.

For example, in the case of setting of the virtual rotation link based on the specifications of the scope, the direction of the virtual rotation link, which is a connection link from the actual rotation link distal end, can be determined from the squint angle information. The distance to a virtual rotation link connected to the actual rotation link distal end can be determined from the scope dimension information. The length of a virtual rotation link for fixing the focus point for motion purpose can be determined from the focus distance information. In this manner, the operation for motion purpose corresponding to various kinds of scope changes can be implemented by using the same control algorithm and simply by the setting change of the virtual rotation link.

Furthermore, when the scope is changed, the above-mentioned virtual rotation link may be dynamically changed as a virtual link independent from the hardware configuration of the arm. For example, when a forward-oblique viewing endoscope having a squint angle of 30 degrees is changed to a forward-oblique viewing endoscope having a squint angle of 45 degrees, a new virtual rotation link can be set again based on the specifications of the changed scope. In this manner, the motion purpose can be switched correspondingly to the scope change.

The setting of the virtual rotation link based on the scope specifications is updated when information on the scope specifications is set to the arm system, but means for inputting the information to the arm system is not limited. For example, the calculation condition setting unit may recognize a scope ID corresponding to a scope when the scope is connected, and acquire the specifications of the scope corresponding to the recognized scope ID.

In this case, if the scope ID has been written in a memory in the scope, the calculation condition setting unit may recognize a scope ID read from the memory. In such a case, the virtual rotation link is updated even when the specifications of the changed scope are not input from a user, and hence a surgery can be smoothly continued. Alternatively, when a scope ID is indicated on the surface of the scope, a user seeing the scope ID may input the scope ID through the input unit 210 as input information, and the calculation condition setting unit may recognize the scope ID based on the input information.

The scope specifications corresponding to the scope ID may be acquired from any place. For example, when the scope specifications are accumulated in a memory in the arm system, the scope specifications may be acquired from the memory in the arm system. Alternatively, when the scope specifications are accumulated in an external device connected to a network, the scope specifications may be acquired through the network. The virtual rotation link may be automatically set based on the thus acquired scope specifications.

Regarding the virtual rotation link, any point on an observation target existing at any distance from a connected scope distal end may be set as a virtual rotation link distal end. The calculation condition setting unit may set or change the virtual rotation link based on the distance or direction from the scope distal end to an observation target obtained from a sensor. Even in the case where the position of an observation target dynamically changes, the calculation condition setting unit may acquire direction and distance information to the scope distal end based on sensor information for specifying the spatial position of the observation target, and set or update the virtual rotation link based on the information. In this manner, gazing operation can be implemented while switching the observation target in a surgery in response to an operation request to continue to gaze the observation target.

Conventionally, the distance or direction from the scope distal end to an observation target is acquired, and the virtual rotation link is set or changed based on the acquired information.

On the other hand, in the present disclosure, as described above with reference to FIG. 10, the three electronic degrees of freedom of pitch, roll, and zoom are provided. The look-around operation with a constant distance to a target, which has a limitation by a conventional endoscope, can be implemented. For example, in the present disclosure, the posture in the look-around operation with a constant distance to a target can be freely taken. In the present disclosure, the target can be looked around while keeping the magnification power of the target constant by adding electronic zoom operation. In other words, the present disclosure can implement the motion of the virtual link by the motion of the electronic degree of freedom without the need of mechanical motion.

7. Hardware Configuration

Figure 21:
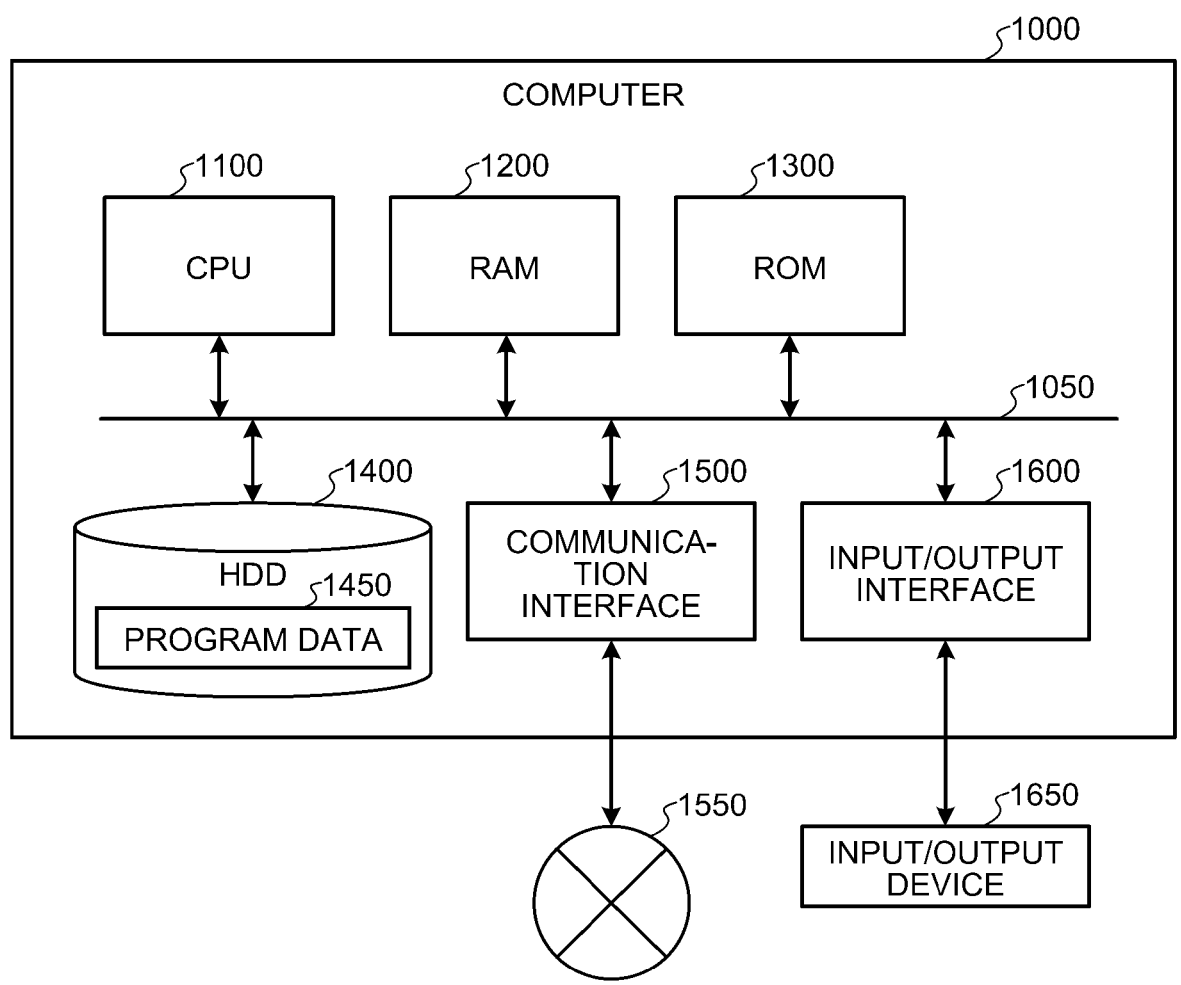
FIG. 21 is a hardware configuration diagram illustrating an example of a computer for implementing the functions of the control device.

The information devices such as the control unit 20 described above are implemented by, for example, a computer 1000 configured as illustrated in FIG. 21. FIG. 21 is a hardware configuration diagram illustrating an example of the computer 1000 for implementing information processing devices such as the control unit 20. The control unit 20 according to the embodiment is described below as an example. The computer 1000 includes a CPU 1100, a RAM 1200, a read only memory (ROM) 1300, a hard disk drive (HDD) 1400, a communication interface 1500, and an input/output interface 1600. The units in the computer 1000 are connected by a bus 1050.

The CPU 1100 operates based on computer programs stored in the ROM 1300 or the HDD 1400, and controls the units. For example, the CPU 1100 deploys computer programs stored in the ROM 1300 or the HDD 1400 onto the RAM 1200, and executes processing corresponding to various kinds of computer programs.

The ROM 1300 stores therein boot programs such as a basic input output system (BIOS) executed by the CPU 1100 at the time of start of the computer 1000 and computer programs depending on hardware of the computer 1000.

The HDD 1400 is a computer-readable recording medium for non-temporarily recording computer programs executed by the CPU 1100 and data used by the computer programs. Specifically, the HDD 1400 is a recording medium for recording an information processing program according to the present disclosure as an example of program data 1450.

The communication interface 1500 is an interface used for the computer 1000 to connect to an external network 1550 (for example, Internet). For example, the CPU 1100 receives data from other devices and transmits data generated by the CPU 1100 to other devices through the communication interface 1500.

The input/output interface 1600 is an interface for connecting the input/output device 1650 and the computer 1000. For example, the CPU 1100 receives data from an input device such as a keyboard and a mouse through the input/output interface 1600. The CPU 1100 transmits data to an output device such as a display, a speaker, and a printer through the input/output interface 1600. The input/output interface 1600 may function as a media interface for reading computer programs recorded in a predetermined recording medium (media). Examples of the media include optical recording media such as a digital versatile disc (DVD) and a phase change rewritable disk (PD), magnetooptical recording media such as a magneto-optical disk (MO), tape media, magnetic recording media, and semiconductor memories.

For example, when the computer 1000 functions as the control unit 20 according to the embodiment, the CPU 1100 in the computer 1000 executes an information processing program loaded on the RAM 1200 to implement the functions of the control unit 20. In the HDD 1400, the information processing program according to the present disclosure and data in the storage unit 60 are stored. The CPU 1100 reads and executes the program data 1450 from the HDD 1400, but in another example, may acquire the programs from another device through the external network 1550.

Effects

The medical observation system 1 includes: the arm portion 11 in which the links are coupled by the joint portion; the imaging unit 12 supported by the arm portion 11 and configured to take a first operative field image; and the control unit 20 configured to drive the joint portion 111 in the arm portion 11 to control the position and posture of the arm portion 11 based on the first operative field image. The control unit 20 generates a second operative field image based on a display target region in the first operative field image, and outputs the second operative field image to the outside. The control unit 20 determines the position and posture of the imaging unit based on a recognition result of operative field environments based on the first operative field image.

This configuration can provide a medical observation system in which the electronic degree of freedom in image processing and the mechanical degree of freedom of the arm portion 11 are combined. Consequently, the mechanism of the arm portion 11 can be simplified to suppress the increase in cost. The motion of the arm portion for achieving desired motion can be minimized to reduce interference with a medical tool or the like in the body of a patient. Hand-eye coordination can be appropriately adjusted to improve the operability for a doctor.

The imaging unit 12 may have a wide-angle optical system.

This configuration can provide a medical observation system in which the electronic degree of freedom in image processing and the mechanical degree of freedom of the arm portion 11 are combined. Consequently, the mechanism of the arm portion 11 can be simplified to suppress the increase in cost. The motion of the arm portion for achieving desired motion can be minimized to reduce interference with a medical tool or the like in the body of a patient. Hand-eye coordination can be appropriately adjusted to improve the operability for a doctor.

The control unit 20 may generate the second operative field image by clipping at least a part of the first operative field image.

With this configuration, the second operative field image, which is a region where a doctor wants to see, can be clipped and generated from the first operative field image taken with a wide angle. Consequently, the orientation and the length of the virtual link can be implemented without the need of a special mechanism.

The control unit 20 may generate the second operative field image by changing a clipping position in accordance with the position and posture of the arm portion 11.

With this configuration, when the position and posture of the arm portion 11 are changed, the clipping position can be set again. Consequently, even when the position and posture of the arm portion 11 are changed, the second operative field image on a screen can be prevented from changing.

The control unit 20 may generate the second operative field image by determining a clipping position from the first operative field image based on the recognition result.

With this configuration, the second operative field image based on the recognition result can be generated. As a result, the second operative field image desired by a doctor can be accurately generated.

The control unit 20 may determine a point of regard in the first operative field image based on the recognition result, and generate the second operative field image including the point of regard.

With this configuration, the second operative field image including the point of regard in the first operative field image can be generated. As a result, the second operative field image desired by a doctor can be more accurately generated.

The control unit 20 may drive the joint portion 111 in the arm portion 11 based on a learned model generated by using data on a surgery as learning data.

With this configuration, the arm portion 11 can be controlled based on learning data on a surgery. Consequently, the position and posture of the arm portion 11 can be autonomously controlled without any instruction from a doctor. The optimal control can be implemented based on a learned model generated based on learning data on the past surgeries.

The data on the surgery may include information on a medical tool used in the surgery.

With this configuration, the position and posture of the arm portion 11 can be controlled based on a medical tool used in a surgery. Consequently, the position and posture of the arm portion 11 can be autonomously controlled based on the medical tool without any instruction from a doctor.

The information on the medical tool may include an image of the medical tool and data on operation of the medical tool.

With this configuration, the position and posture of the arm portion 11 can be controlled based on an image of a medical tool used in a surgery and data on operation of the medical tool. As a result, the position and posture of the arm portion 11 can be more appropriately controlled.

The medical tool may be an endoscope.

With this configuration, the position and posture of the arm portion 11 can be controlled based on an image of an endoscope used in a surgery and data on operation of the endoscope.

The data on the surgery includes information on the arm portion 11.

With this configuration, the position and posture of the arm portion 11 can be controlled based on information on the arm portion 11. Consequently, the position and posture of the arm portion 11 can be autonomously controlled based on information on the arm portion 11 without any instruction from a doctor.

The information on the arm portion 11 includes information on a state of the joint portion 111 in the arm portion 11.

With this configuration, the position and posture of the arm portion 11 can be controlled based on information on the state of the joint portion 111 in the arm portion 11. As a result, the position and posture of the arm portion 11 can be more appropriately controlled.

The information on the joint portion 111 in the arm portion 11 includes information on motion of the joint portion 111 in the arm portion 11.

With this configuration, the position and posture of the arm portion 11 can be controlled based on information on the motion of the joint portion 111 in the arm portion 11. As a result, the position and posture of the arm portion 11 can be more appropriately controlled.

The information on the arm portion 11 includes information on a medical tool gripped by the arm portion 11.

With this configuration, the position and posture of the arm portion 11 can be controlled based on information on a medical tool gripped by the arm portion 11. Consequently, the position and posture of the arm portion 11 can be autonomously controlled based on information on the medical tool gripped by the arm portion 11 without any instruction from a doctor.

The information on the medical tool gripped by the arm portion 11 includes at least one of a type of the medical tool and position information and posture information on the medical tool.

With this configuration, the position and posture of the arm portion 11 can be controlled based on at least one of position information and posture information on the medical tool gripped by the arm portion 11. As a result, the position and posture of the arm portion 11 can be more appropriately controlled.

The learning data includes a measurement result of a stereo sensor, a depth sensor, and a motion sensor.

With this configuration, the joint portion 111 in the arm portion 11 can be driven by using learning data including a measurement result of at least one of a stereo sensor, a depth sensor, and a motion sensor. Consequently, the position and posture of the arm portion 11 can be more appropriately controlled based on measurement results by a stereo sensor, a depth sensor, and a motion sensor in a surgery.

The learning data includes information on operative field environments including at least one of a position, a posture, a type, and motion of a medical tool and an organ obtained from at least one of a stereo sensor, a depth sensor, and a motion sensor.

With this configuration, the joint portion 111 in the arm portion 11 can be driven based on information on the position, the posture, the type, and the motion of a medical tool and an organ obtained from at least one of a stereo sensor, a depth sensor, and a motion sensor. Consequently, the position and posture of the arm portion 11 can be more appropriately controlled based on measurement results by a stereo sensor, a depth sensor, and a motion sensor in a surgery.

The determination unit 24 determines the position and posture of the arm portion 11 based on at least one of posture information on the arm portion 11 and measurement results by a stereo sensor, a depth sensor, and a motion sensor.

With this configuration, the determination unit 24 determines the position and posture of the arm portion 11 based on measurement results of various kinds of sensors. As a result, the position and posture of the arm portion 11 can be more appropriately controlled.

The determination unit 24 determines the position and posture of the arm portion 11 based on at least one of an object and a treatment status included in the first operative field image.

With this configuration, the determination unit 24 can use an object included in the first operative field image and contents of treatment as data to be input to the learned model and executed.

The object is an organ and a medical tool included in the first operative field image.

With this configuration, the determination unit 24 can use a medical tool included in the first operative field image as data to be input to the learned model and executed.

The determination unit 24 determines the position and posture of the arm portion 11 based on at least one of a type and a shape of an organ and a position, a posture, and a shape of a medical tool.

With this configuration, the determination unit 24 can use at least one of the type and shape of the organ and the position, posture, and shape of the medical tool as data to be input to the learned model and executed.

The medical observation system 1 may include the processing unit 213 for performing image processing for image correction on the second operative field image.

With this configuration, various kinds of image processing can be executed on the second operative field image.

The control unit 20 may perform image processing on the first operative field image.

With this configuration, various kinds of image processing can be executed on the first operative field image.

The control unit 20 may perform image quality improving processing on the second operative field image.

With this configuration, the second operative field image visually recognized by a doctor can be provided with high quality. Specifically, the second operative field image can be provided with the same fine image quality as in conventional endoscopes.

The processing unit 213 may perform at least one of super-resolution processing, distortion correction, boosting, noise reduction (NR) processing, image stabilization, and luminance correction processing on the second operative field image.

With this configuration, various kinds of high image processing can be performed on the second operative field image.

The control unit 20 may change image processing performed on the second operative field image in accordance with a clipping position of the second operative field image.

With this configuration, optimal image processing corresponding to the clipping position of the second operative field image can be executed, and hence the image quality of the second operative field image can be improved.

The control unit 20 may change processing performed on the second operative field image based on information input to the control unit 20.

With this configuration, optimal image processing corresponding to information input to the control unit 20 can be executed, and hence the image quality of the second operative field image can be improved.

The processing unit 213 may change image processing performed on the second operative field image based on at least one of information on motion of the joint portion 111 in the arm portion 11, a recognition result of operative field environments based on the first operative field image, and an object and a treatment status included in the first operative field image.

With this configuration, at least one of information on motion of the joint portion 111 in the arm portion 11, a recognition result of operative field environments based on the first operative field image, and an object and a treatment status included in the first operative field image can be used as information input to the control unit 20.

The control unit 20 may generate a third operative field image obtained by performing image quality decreasing processing based on the first operative field image, and the determination unit 24 may recognize operative field environments based on the third operative field image, and determine the position and posture of the arm portion 11 based on the recognition result.

With this configuration, the target can be recognized based on an image with decreased resolution, and hence processing load can be reduced. As a result, power consumption can be reduced.

The control unit 20 may perform image quality decreasing processing on the second operative field image.

With this configuration, the second operative field image with reduced resolution can be generated, and hence processing load can be reduced. As a result, power consumption can be reduced.

The control unit 20 may determine a region of interest for a user as the display target region, and drive the joint portion 111 in the arm portion 11 so as to improve the image quality of the region of interest.

With this configuration, a region of interest for a doctor can be autonomously determined, and the position and posture of the arm portion 11 can be controlled based on the determination result. Consequently, the image quality of the region of interest can be improved.

The control unit 20 may drive the joint portion 111 in the arm portion 11 so as to avoid a medical tool that blocks the visual field of a user for the region of interest.

With this configuration, when it is determined that there is a medical tool in the region of interest, the arm portion 11 can be controlled so as to avoid the medical tool. Consequently, the visibility of the region of interest can be improved.

The control unit 20 may drive the joint portion 111 in the arm portion 11 such that the region of interest is shifted from the center of a screen.

With this configuration, when it is assumed that a medical tool is located at the center of the screen, the arm portion 11 can be controlled such that the region of interest appears at an end of the screen. Consequently, the visibility of the region of interest can be controlled.

The control unit 20 may drive the joint portion 111 in the arm portion 11 so as to avoid specular reflection from the region of interest.

With this configuration, the position and posture of the arm portion 11 can be changed so as to avoid reflection of light from the region of interest. Consequently, the reflection of light from the region of interest can be reduced, and hence the image quality of the region of interest can be improved.

The control unit 20 may change the position of the light source unit 13 and the position of the imaging unit 12 with respect to the region of interest.

With this configuration, by changing the position and posture of the arm portion 11 and changing the position of the light source unit 13 and the position of the imaging unit 12, the reflection of light from the region of interest can be reduced. Consequently, the image quality of the region of interest can be improved.

The control unit 20 may control a light amount of the light source unit 13 based on a positional relation of the imaging unit 12 with respect to the region of interest.

With this configuration, the light amount of the light source unit 13 can be adjusted in accordance with the position of the imaging unit 12 with respect to the region of interest. As a result, the optimal light amount can be achieved depending on the position of the imaging unit 12, and hence the reflection of light can be reduced to improve the visibility of the region of interest.

The control unit 20 may control the position and posture of the arm portion 11 so as to suppress distortion in the circumference of the region of interest.

With this configuration, distortion can be suppressed when the center of the region of interest is observed or treated. Consequently, the image quality of the region of interest can be improved.

The control unit 20 may drive the joint portion 111 in the arm portion 11 such that the region of interest is located at substantially the center of the first operative field image.

With this configuration, the region of interest visually recognized by a doctor is located at substantially the center of the first operative field image, and hence the treatment by a doctor can be easily checked in the first operative field image.

The control device includes the control unit configured to drive the joint portion 111 in the arm portion 11 based on a first operative field image to control the position and posture of the imaging unit. The control unit generates a second operative field image based on a display target region in the first operative field image, and outputs the second operative field image to the outside. The control unit determines the position and posture of the imaging unit based on a recognition result of operative field environments based on the first operative field image.

This configuration can provide a medical observation system in which the electronic degree of freedom in image processing and the mechanical degree of freedom of the arm portion 11 are combined. Consequently, the mechanism of the arm portion 11 can be simplified to suppress the increase in cost. The motion of the arm portion for achieving desired motion can be minimized to reduce interference with a medical tool or the like in the body of a patient. Hand-eye coordination can be appropriately adjusted to improve the operability for a doctor.

A control method for a medical observation system includes: generating a second operative field image based on a display target region in a first operative field image taken by the imaging unit 12 supported by the arm portion 11, and outputting the second operative field image to the outside; and determining a position and a posture of the imaging unit 12 based on a recognition result of operative field environments based on the first operative field image.

This method can provide a medical observation system in which the electronic degree of freedom in image processing and the mechanical degree of freedom of the arm portion 11 are combined. Consequently, the mechanism of the arm portion 11 can be simplified to suppress the increase in cost. The motion of the arm portion for achieving desired motion can be minimized to reduce interference with a medical tool or the like in the body of a patient. Hand-eye coordination can be appropriately adjusted to improve the operability for a doctor.

The effects described herein are merely illustrative and are not limited. Other effects may be obtained.

The present technology may have configurations as follows.

(1)
According to one embodiment, a method of processing medical images, including acquiring a first medical image using a medical imaging device; analyzing a state of the first medical image using image information of the first medical image which includes depth information; automatically determining, without user intervention, a second medical image, which corresponds to the first medical image and has a smaller angle of view than the first medical image, based on the analyzing including analyzing of the depth information; and displaying the second medical image.

(2)
According to the embodiment of (1), the determining includes determining a position at which the medical imaging device is to capture the second medical image, based on the analyzing; moving the medical imaging device to the position which has been determined; and capturing, prior to the displaying the second medical image, the second medical image when the medical imaging device is at the position which has been determined.

(3)
According to the embodiment (1), the determining includes determining clipping information for the first medical image, based on the analyzing; and clipping the first medical image to generate the second medical image using the clipping information.

(4)
According to the embodiment of (1), wherein the determining includes determining a position at which the medical imaging device is to capture the second medical image, based on the analyzing; moving the medical imaging device to the position which has been determined; determining clipping information of the second medical image; and creating the second medical image using the medical imaging device being located at the position which has been determined and the clipping information.

(5)
Further, according to the embodiment of (4), wherein the creating creates the second medical image by clipping a newly captured image which is different from the first medical image.

(6)
Further, according to the embodiment of (1), wherein the first medical image is acquired through a wide-angle lens.

(7)
Further, according to the embodiment of (1), the analyzing includes analyzing a state of the first medical image by analyzing an existence of at least one of a medical tool and an organ which are in the first medical image.

(8)
Further, according to the embodiment of (7), the analyzing comprises: analyzing a state of the first medical image by analyzing the existence of both of the medical tool and the organ which are in the first medical image.

(9)
Further, according to the embodiment of (1), the analyzing analyzes camera position information and surgical tool information to create a model, and the automatically determining utilizes the model to determine that the second image is to be displayed and to determine the second image.

(10)
Further, according to the embodiment of (9), the model is a neural network, and the analyzing creates the neural network.

(11)

Further, according to the embodiment of (1), an image processing is performed on the second medical image before the displaying.

(12)

Further, according to the embodiment of (11), the image processing includes at least one of super resolution processing, distortion correction, boosting, noise reduction (NR) processing, image stabilization, and luminance correction processing.

(13)

Further, according to the embodiment of (11), there further includes determining a type of image processing to be performed based on clipping information.

(14)

Further, according to the embodiment of (13), the clipping information includes a clipping position.

(15)

According to another embodiment, there is a medical system which includes a medical imaging device; circuitry configured to control the medical imaging device to acquire a first medical image; circuitry configured to perform analyzing of a state of the first medical image using image information of the first medical image which includes depth information; and circuitry configured to automatically determine without user intervention a second medical image, which corresponds to the first medical image and has a smaller angle of view than the first medical image, based on the analyzing including analyzing of the depth information, and cause a display to display the second medical image.

(16)

Further, according to the embodiment of (15), the circuitry configured to determine includes circuitry configured to determine a position at which the medical imaging device is to capture the second medical image, based on the analyzing; and circuitry configured to move the medical imaging device to the position which has been determined; circuitry configured to capture, using the medical imaging device, prior to the displaying the second medical image, the second medical image when the medical imaging device is at the position which has been determined.

(17)

Further, according to the embodiment of (15), the circuitry configured to determine includes circuitry configured to determine clipping information for the first medical image, based on the analyzing; and circuitry configured to clip the first medical image to generate the second medical image using the clipping information.

(18)

Further, according to the embodiment of (15), the circuitry configured to determine includes circuitry configured to determine a position at which the medical imaging device is to capture the second medical image, based on the analyzing; circuitry configured to move the medical imaging device to the position which has been determined; circuitry configured to determine clipping information of the second medical image; and circuitry configured to create the second medical image using the medical imaging device being located at the position which has been determined and the clipping information.

(19)

Further, according to the embodiment of (18), the circuitry configured to create creates the second medical image by clipping a newly captured image which is different from the first medical image.

(20)

Further, according to the embodiment of (15), the first medical image is acquired by the medical imaging device through a wide-angle lens.

(21)

Further, according to the embodiment of (15), the circuitry configured to analyze analyzes a state of the first medical image by analyzing an existence of at least one of a medical tool and an organ which are in the first medical image.

(22)

Further, according to the embodiment of (21), the circuitry configured to analyze analyzes a state of the first medical image by analyzing the existence of both of the medical tool and the organ which are in the first medical image.

(23)

Further, according to the embodiment of (15), the circuitry configured to perform analyzing analyzes camera position information and surgical tool information to create a model, and the circuitry configured to automatically determine utilizes the model to determine that the second image is to be displayed and to determine the second image.

(24)

Further, according to the embodiment of (23), the model is a neural network, and the circuitry configured to perform analyzing creates the neural network.

(25)

Further, according to the embodiment of (15), the embodiment further includes circuitry configured to perform an image processing on the second medical image prior to the displaying of the second medical image.

(26)

Further, according to the embodiment of (25), the image processing includes at least one of super resolution processing, distortion correction, boosting, noise reduction (NR) processing, image stabilization, and luminance correction processing.

(27)

Further, according to the embodiment of (25), the embodiment further includes circuitry configured to determine a type of image processing to be performed based on clipping information.

(28)

Further, according to the embodiment of (27), the clipping information includes a clipping position.

(29)

Further, according to another embodiment, there is a computer-implemented method of training a neural network, including collecting a set of training information which includes image quality information, camera position information, and surgical tool information; training the neural network based on the set of training information, the neural network used for changing a view based on current camera position information and current surgical tool information.

(30)

Further, according to the embodiment of (29), the surgical tool information of the training information includes a type of the surgical tool and a position of the surgical tool.

(31)

Further, according to the embodiment of (30), the position of the surgical tool is indicated by an X, a Y, and a Z coordinate.

(32)

Further, according to the embodiment of (31), the surgical tool information of the training information includes surgical tool information of at least two surgical tools.

(33)

Further, according to the embodiment of (29), the camera position information of the training information is indicated by an X, a Y, and a Z coordinate.

(34)

Further, according to the embodiment of (29), the image quality information is indicated by at least two level values corresponding to a quality of the image presented to a viewer.

(35)

Further, according to the embodiment of (29), the image quality information is a single number.

(36)

Further, according to the embodiment of (29), the camera position information is based on position information of an arm supporting the camera.

The present technology may alternatively have configurations as follows.

(1)

A medical observation system, including:
an arm portion in which a plurality of links are coupled by a joint portion;
an imaging unit supported by the arm portion and configured to take a first operative field image; and
a control unit configured to drive the joint portion in the arm portion to control a position and a posture of the imaging unit based on the first operative field image, wherein
the control unit
generates a second operative field image based on a display target region in the first operative field image, and output the second operative field image to the outside, and
determines the position and the posture of the imaging unit based on a recognition result of operative field environments based on the first operative field image.

(2)

The medical observation system according to (1), wherein the imaging unit includes a wide-angle optical system.

(3)

The medical observation system according to (1) or (2), wherein the control unit generates the second operative field image by clipping at least a part of the first operative field image.

(4)

The medical observation system according to any one of (1) to (3), wherein the control unit generates the second operative field image by changing a clipping position from the first operative field image in accordance with the position and the posture of the imaging unit.

(5)

The medical observation system according to (3), wherein the control unit generates the second operative field image by determining a clipping position from the first operative field image based on the recognition result.

(6)

The medical observation system according to (5), wherein the control unit determines a point of regard in the first operative field image based on the recognition result, and generates the second operative field image including the point of regard.

(7)

The medical observation system according to any one of (1) to (6), wherein the control unit drives the joint portion in the arm portion based on a learned model generated by using data on a surgery as learning data.

(8)

The medical observation system according to (7), wherein the data on the surgery includes information on a medical tool used in the surgery.

(9)

The medical observation system according to (8), wherein the information on the medical tool includes image data acquired by the medical tool and data on operation of the medical tool.

(10)

The medical observation system according to (9), wherein the medical tool is an endoscope.

(11)

The medical observation system according to any one of (7) to (10), wherein the data on the surgery includes information on the arm portion.

(12)

The medical observation system according to (11), wherein the information on the arm portion includes information on a state of the joint portion in the arm portion.

(13)

The medical observation system according to (12), wherein the information on the joint portion in the arm portion includes information on motion of the joint portion in the arm portion.

(14)

The medical observation system according to any one of (11) to (13), wherein the information on the arm portion includes information on a medical tool gripped by the arm portion.

(15)

The medical observation system according to (14), wherein the information on the medical tool gripped by the arm portion includes at least one of a type of the medical tool and position information and posture information on the medical tool.

(16)

The medical observation system according to any one of (7) to (15), in which the learning data includes a measurement result of at least one of a stereo sensor, a depth sensor, and a motion sensor.

(17)

The medical observation system according to (16), in which the learning data includes information on operative field environments including at least one of a position, a posture, a type, and motion of the medical tool and an organ obtained from at least one of the stereo sensor, the depth sensor, and the motion sensor.

(18)

The medical observation system according to any one of (1) to (17), wherein the control unit determines the position and the posture of the imaging unit based on a measurement result of at least one of posture information on the arm portion and a measurement result by at least one of a stereo sensor, a depth sensor, and a motion sensor.

(19)

The medical observation system according to any one of (1) to (18), wherein the control unit determines the position and the posture of the imaging unit based on at least one of an object and a treatment status included in the first operative field image.

(20)

The medical observation system according to (19), wherein the object is an organ and a medical tool included in the first operative field image.

(21)

The medical observation system according to (20), wherein the control unit determines the position and the posture of the imaging unit based on at least one of a type and a shape of the organ and a position, a posture, and a shape of the medical tool.

(22)

The medical observation system according to any one of (1) to (21), wherein the control unit further performs image processing for image correction on the second operative field image.

(23)

The medical observation system according to (22), in which the control unit performs the image processing on the first operative field image.

(24)

The medical observation system according to (22) or (23), wherein the control unit performs image quality improving processing on the second operative field image.

(25)

The medical observation system according to (24), wherein the control unit performs at least one of super-resolution processing, distortion correction, boosting, noise reduction (NR) processing, image stabilization, and luminance correction processing on the second operative field image.

(26)

The medical observation system according to any one of (22) to (25), wherein the control unit changes image processing performed on the second operative field image in accordance with a clipping position of the second operative field image.

(27)

The medical observation system according to any one of (22) to (26), wherein the control unit changes processing performed on the second operative field image based on information input to the control unit.

(28)

The medical observation system according to (27), in which the control unit changes image processing performed on the second operative field image based on at least one of information on motion of the joint portion in the arm portion, a recognition result of operative field environments based on the first operative field image, and an object and a treatment status included in the first operative field image.

(29)

The medical observation system according to any one of (1) to (28), wherein the control unit is configured to:
  generate a third operative field image obtained by performing image quality decreasing processing based on the first operative field image; and
  determine the position and the posture of the imaging unit based on the recognition result of the operative field environments based on the third operative field image.

(30)

The medical observation system according to any one of (1) to (29), in which the control unit performs image quality decreasing processing on the second operative field image.

(31)

The medical observation system according to any one of (1) to (30), wherein the control unit determines a region of interest for a user as the display target region, and drives the joint portion in the arm portion so as to improve image quality in the region of interest.

(32)

The medical observation system according to (31), wherein the control unit drives the joint portion in the arm portion so as to avoid a medical tool that blocks a visual field of the user for the region of interest.

(33)

The medical observation system according to (31) or (32), wherein the control unit drives the joint portion in the arm portion such that the region of interest is shifted from a center of a screen.

(34)

The medical observation system according to any one of (31) to (33), in which the control unit drives the joint portion in the arm portion so as to avoid specular reflection from the region of interest.

(35)

The medical observation system according to any one of (31) to (34), wherein the control unit changes a position of a light source unit and the position of the imaging unit with respect to the region of interest.

(36)

The medical observation system according to (35), wherein the control unit controls a light amount of the light source unit based on a positional relation of the imaging unit with respect to the region of interest.

(37)

The medical observation system according to any one of (31) to (36), wherein the control unit controls the position and the posture of the imaging unit so as to suppress distortion in a circumference of the region of interest.

(38)

The medical observation system according to any one of (31) to (37), wherein the control unit drives the joint portion in the arm portion such that the region of interest is located at substantially a center of the first operative field image.

(39)

A control device for a medical observation system, including a control unit configured to drive a joint portion in an arm portion to control a position and a posture of an imaging unit based on a first operative field image, wherein the control unit is configured to: generate a second operative field image based on a display target region in the first operative field image, and output the second operative field image to the outside; and determine the position and the posture of the imaging unit based on a recognition result of operative field environments based on the first operative field image.

(40)

A control method for a medical observation system, including: generating a second operative field image based on a display target region in a first operative field image taken by an imaging unit supported by an arm portion, and outputting the second operative field image to the outside; and determining a position and a posture of the imaging unit based on a recognition result of operative field environments based on the first operative field image.

REFERENCE SIGNS LIST

1 Medical observation system
10 Robot arm device
11 Arm portion
20 Control unit (control device)
21 Image processing unit
22 Imaging control unit
23 Arm control unit
24 Learning unit
25 Reception unit
26 Display control unit
30 Operation unit 40 First operative field image display unit
50 Second operative field image display unit
60 Storage unit
111 Imaging unit
112 Light source unit
113 Joint portion
211 Acquisition unit
212 Generation unit
213 Processing unit
214 Recognition unit
215 Evaluation unit

The invention claimed is:

1. A method of processing medical images, comprising:
acquiring a first medical image using a medical imaging device;
analyzing a state of the first medical image using image information of the first medical image which includes depth information;
automatically determining, without user intervention, a second medical image, which corresponds to a region of interest in the first medical image and has a smaller angle of view than the first medical image, based on the analyzing including analyzing of the depth information;
determining a position at which the medical imaging device is to capture the second medical image, based on the analyzing;
moving the medical imaging device to the position which has been determined;
capturing the second medical image when the medical imaging device is at the position which has been determined;
displaying the second medical image; and
determining whether the region of interest is obstructed at a center of the first medical image, wherein
in response to the region of interest being obstructed at the center of the first medical image, shifting the position at which the medical imaging device is to capture the second medical image is shifted from the center of the first medical image, and
in response to the region of interest not being obstructed at the center of the first medical image, maintaining the position at which the medical imaging device is to capture the second medical image.

2. The method according to claim 1, wherein the determining comprises:
determining clipping information for the first medical image, based on the analyzing; and
clipping the first medical image to generate the second medical image using the clipping information.

3. The method according to claim 1, wherein the determining comprises:
determining clipping information of the second medical image; and
creating the second medical image using the medical imaging device being located at the position which has been determined and the clipping information.

4. The method according to claim 3, wherein the creating creates the second medical image by clipping a newly captured image which is different from the first medical image.

5. The method according to claim 1, wherein the first medical image is acquired through a wide-angle lens.

6. The method according to claim 1, wherein the analyzing comprises:
analyzing a state of the first medical image by analyzing an existence of at least one of a medical tool and an organ which are in the first medical image.

7. The method according to claim 6, wherein the analyzing comprises:
analyzing a state of the first medical image by analyzing the existence of both of the medical tool and the organ which are in the first medical image.

8. The method according to claim 1, wherein:
analyzing analyzes camera position information and surgical tool information to create a model, and
automatically determining utilizes the model to determine that the second medical image is to be displayed and to determine the second medical image to be displayed.

9. The method according to claim 8, wherein:
the model is a neural network, and
the analyzing creates the neural network.

10. The method according to claim 1, further comprising:
image processing the second medical image before the displaying.

11. The method according to claim 10, wherein:
image processing includes at least one of super resolution processing, distortion correction, boosting, noise reduction (NR) processing, image stabilization, and luminance correction processing.

12. The method according to claim 10, further comprising:
determining a type of image processing to be performed based on clipping information.

13. The method according to claim 12, wherein:
the clipping information includes a clipping position.

14. A medical system, comprising:
a medical imaging device; and
circuitry configured to:
control the medical imaging device to acquire a first medical image;
analyze a state of the first medical image using image information of the first medical image which includes depth information; and
automatically determine, without user intervention, a second medical image, which corresponds to a region of interest in the first medical image and has a smaller angle of view than the first medical image, based on the analyzing including analyzing of the depth information;
determine a position at which the medical imaging device is to capture the second medical image, based on the state of the first medical image;
move the medical imaging device to the position which has been determined;
capture, using the medical imaging device, the second medical image when the medical imaging device is at the position which has been determined; and
cause a display to display the second medical image, wherein
on condition that the region of interest is obstructed at a center of the first medical image, shift the position at which the medical imaging device is to capture the second medical image from the center of the first medical image.

15. The system according to claim 14, wherein the circuitry is configured to:
determine clipping information for the first medical image, based on the analyzing; and clip the first medical image to generate the second medical image using the clipping information.

16. The system according to claim 14, wherein the circuitry configured to:
determine clipping information of the second medical image; and
create the second medical image using the medical imaging device being located at the position which has been determined and the clipping information.

17. The system according to claim 16, wherein, to create the second medical image, the circuitry is configured to create the second medical image by clipping a newly captured image which is different from the first medical image.

18. The system according to claim 14, wherein the first medical image is acquired by the medical imaging device through a wide-angle lens.

19. The system according to claim 14, wherein, to analyze the state, the circuitry is configured to analyze an existence of at least one of a medical tool and an organ which are in the first medical image.

20. The system according to claim 19, wherein the circuitry is configured to analyze the existence of both of the medical tool and the organ which are in the first medical image.

21. The system according to claim 14, wherein:
to analyze the state, the circuitry is configured to analyze camera position information and surgical tool information to create a model, and
to automatically determine the second medical image, the circuitry is configured to utilize the model to determine that the second medical image.

22. The system according to claim 21, wherein:
the model is a neural network, and
to analyze the state, the circuitry is configured to create the neural network.

23. The system according to claim 14, wherein the circuitry is configured to perform an image processing on the second medical image prior to causing the display of the second medical image.

24. The system according to claim 23, wherein:
the image processing includes at least one of super resolution processing, distortion correction, boosting, noise reduction (NR) processing, image stabilization, and luminance correction processing.

25. The system according to claim 23,
wherein the circuitry is configured to determine a type of image processing to be performed based on clipping information.

26. The system according to claim 25, wherein:
the clipping information includes a clipping position.

27. The system according to claim 14, further comprising:
a light source that provides illumination to the region of interest, wherein
the circuitry is configured to control a brightness of the light source based on a positional relation of the medical imaging device with respect to the region of interest.

28. The system according to claim 14, further comprising:
a light source that provides illumination to the region of interest, wherein
the circuitry is further configured to control the position and a posture of at which the medical imaging device is to capture the second medical image based on a positional relation of the imaging device and of the light source with respect to the region of interest.

29. The method according to claim 1, wherein the position at which the medical imaging device is to capture the second medical image is shifted from a center of the first medical image.

30. The method according to claim 1, further comprising:
controlling a brightness of a light source that provides illumination to the region of interest based on a positional relation of the medical imaging device with respect to the region of interest.

31. The method according to claim 1, further comprising:
controlling the position and a posture of at which the medical imaging device is to capture the second medical image based on a positional relation of the imaging device and of a light source that provides illumination to the region of interest with respect to the region of interest.

32. A non-transitory computer readable medium storing a program causing a controller of a medical imaging device to execute the method according to claim 1.

33. A medical control system, comprising:
circuitry configured to:
control a medical imaging device to acquire a first medical image;
analyze a state of the first medical image using image information of the first medical image which includes depth information; and
automatically determine, without user intervention, a second medical image, which corresponds to a region of interest in the first medical image and has a smaller angle of view than the first medical image, based on the analyzing including analyzing of the depth information;
determine a position at which the medical imaging device is to capture the second medical image, based on the state of the first medical image;
move the medical imaging device to the position which has been determined;
capture, using the medical imaging device, the second medical image when the medical imaging device is at the position which has been determined; and
cause a display to display the second medical image, wherein,
on condition that the region of interest is obstructed at a center of the first medical image, shift the position at which the medical imaging device is to capture the second medical image from the center of the first medical image.

34. The system of claim 33, wherein the circuitry is configured to:
determine clipping information of the second medical image; and
create the second medical image using the medical imaging device being located at the position which has been determined and the clipping information.

* * * * *